US006787541B1

(12) United States Patent
Gillespie et al.

(10) Patent No.: US 6,787,541 B1
(45) Date of Patent: Sep. 7, 2004

(54) THIENO-AND FUROPYRIMIDINE DERIVATIVES AS A2A-RECEPTOR ANTAGONISTS

(75) Inventors: Roger John Gillespie, Wokingham (GB); Joanne Lerpiniere, Wokingham (GB); Paul Richard Giles, Wokingham (GB); Claire Elizabeth Dawson, Wokingham (GB); David Bebbington, Wiltshire (GB)

(73) Assignee: Vernalis Research Limited, Winnersh (GB)

( * ) Notice: Subject to any disclaimer, the term of this patent is extended or adjusted under 35 U.S.C. 154(b) by 0 days.

(21) Appl. No.: 09/958,948

(22) PCT Filed: Jun. 30, 2000

(86) PCT No.: PCT/GB00/02517

§ 371 (c)(1),
(2), (4) Date: Mar. 13, 2002

(87) PCT Pub. No.: WO01/02409

PCT Pub. Date: Jan. 11, 2001

(30) Foreign Application Priority Data

Jul. 1, 1999 (GB) .............................................. 9915437

(51) Int. Cl.[7] .................... C07D 495/04; C07D 491/04; A61K 31/505; A61P 25/14
(52) U.S. Cl. .................... 514/234.2; 544/278; 544/117; 514/258.1; 514/252.16
(58) Field of Search ................................ 544/278, 117; 514/258.1, 234.2, 252.16

(56) References Cited

U.S. PATENT DOCUMENTS

| 6,197,788 B1 | 3/2001 | Fletcher et al. |
| 6,583,156 B1 | 6/2003 | Gillespie et al. |
| 6,608,085 B1 | 8/2003 | Gillespie et al. |

FOREIGN PATENT DOCUMENTS

| EP | 1 221 444 A1 | 7/2002 |
| EP | 1 300 147 A1 | 4/2003 |
| WO | WO-97/05139 | 2/1997 |
| WO | WO-99/40091 | 8/1999 |

OTHER PUBLICATIONS

Ongini Monopoli and Cacciari Baraldi "Selective adenosine A2A receptor antagonists" Farmaco 2001 56:87–90 (Abstract).*
Strappaghetti, Giovannella; "Adenosine receptors: synthesis, structure–activity relationships and biological activity of new 6–amino purine derivatives", Eur. J. Med. Chem. 33 (1998) 501–508, Elsevier, Paris.
Mally et al., "Potential of Adenosine $A_{2A}$ Receptor Antagonists in the Treatment of Movement Disorders," Leading Articles, vol. 10, No. 5, Ads International Limited, Nov. 1998, pp. 311–320.

Bastia et al., "Effects of $A_1$ and $A_{2A}$ Adenosine Receptor Ligands in Mouse Acute Models of Pain," Neuroscience Letters, Elsevier, 2002, pp. 241–244.
Yacoubi et al., "Adenosine $A_{2A}$ Receptor Antagonists are Potential Antidepressants Evidence Based on Pharmacology and $A_{2A}$ Receptor Knockout Mice," British Journal of Pharmacology, vol. 134, Nature Publishing Group, 2001, pp. 68–77.
Dall'lgna et al., "Neuroprotection by Caffeine and Adenosine $A_{2A}$ Receptor Blockade of β–amyloid Neurotoxicity," British Journal of Pharmacology, vol. 138, Nature Publishing Group, 2003, pp. 1207–1209.
Varani et al., :Adenosine $A_{2A}$ Antagonists and Huntington's Disease, Department of Clinical and Experimental Medicine; 8 Sheets.
Stone et al., "Neuroprotection by $A_{2A}$ Receptor Antagonists," Research Overview, vol. 52, Drug Development Research, Willey–Liss, Inc., 2001, pp. 323–330.
Behan et al., "Enhanced Neuronal Damage by Co–Administration of Quinolinic Acid and Free Radicals, and Protection by Adenosine $A_{2A}$ Receptor Antagonist," British Journal of Pharmacology, vol. 135, Nature Publishing Group, 2002, pp. 1435–1442.
Monopoli et al, "Blockade of Adenosine $A_{2A}$ Receptors by SCH 58261 Results in Neuroprotective Effects in Cerebral Ischaemia in Rats," Neuropharmacology, vol. 9, No. 17, Neuro Report, Lippincott Williams & Wilkins, 1998, pp. 3955–3959.
Bertorelli et al., "Effects of Selective Agonists and Antagonists for $A_1$ or $A_{2A}$ Adenosine Receptors on Sleep–Walking Patterns in Rats," Research Articles, vol. 37, Drug Development Research, Wiley–Liss, Inc., 1996, pp. 65–72.
Scammell et al., "An Adenosine $A_{2A}$ Agonists Increases Sleep and Induces Fos in Ventrolateral Preoptic Neurons," Neuroscience, vol. 107, No. 4, Pergamon, 2001, pp. 653–663.

(List continued on next page.)

*Primary Examiner*—Mukund J. Shah
*Assistant Examiner*—Hong Liu
(74) *Attorney, Agent, or Firm*—Foley & Lardner LLP

(57) ABSTRACT

Compounds of formula (I):

(I)

wherein X is S. Compounds can be used for treating a disorder in which the blocking of purine receptors is beneficial.

40 Claims, No Drawings

OTHER PUBLICATIONS

Satoh et al., "Involvement of Adenosine $A_{2A}$ Receptor in Sleep Promotion," European Journal of Pharmacology, vol. 351, Elsevier, 1998, pp. 155–162.

Ll et al., "Differing Roles of Adenosine Receptor Subtypes in Retinal Ischemia–Reperfusion Injury in the Rat," Exp. Eye Res., vol. 68, Academic Press, 1999, pp. 9–17.

Monopoli et al., "Cardiovascular Pharmacology of the $A_{2A}$ Adenosine Receptor Antagonists, SCH 58261 in the Rat," The Journal of Pharmacology and Experimental Therapeutics, vol. 255, No. 1, The American Society for Pharmacology and Experimental Therapeutics, 1998, pp. 9–15.

Hess, "Recent Advances in Adenosine Receptor Antagonist Research," Review, Monthly Focus: Central & Peripheral Nervous Systems, Ashley Publications Ltd. 2001, pp. 1533–1561.

Gonzalez–Benitez et al., Regulation of Glycogen Metabolism in Hepatocytes Through Adenosine Receptors Role of $Ca^{2+}$ and cAMP, European Journal of Pharmacology, vol. 437, Elsevier, 2002, pp. 105–111.

Asano et al., "Preparation of Fused Imidazole Compounds and Remedies for Diabetes Mellitus," SciFinder, May 20, 2003, pp. 1–2; Abstract.

Asano et al., "Preparation of Purine Derivatives as Adenosine A2 Receptor Antagonists for the Treatment of Diabetes," SciFinder, May 20, 2003, pp. 1–2; Abstract.

Bruns et al., "Characterization of the $A_2$ Adenosine Receptor Labeled by [$^3$H] NECA in Rat Striatal Membranes," Molecular Pharmacology, 29, The American Society for Pharmacology and Experimental Therapeutics, 1986, pp. 331–346.

Bara–Jimenez, W. et al., "Adenosine A2A receptor antagonist treatment of Parkinson's disease," Neurology, 61(3), 2003, pp. 293–296. (Abstract).

Hauser, Robert A. et al., "Randomized trial of the adenosine A2A receptor antagonist istradefylline in advanced PD," Neurology, 61(3), 2003, pp. 297–303. (Abstract).

Chase, T. N. et al., "Translating A2A antagonist KW6002 from animal modes to parkinsonian patients," Neurology, 61(11. Suppl. 6), 2003, pp. S107–S111. (Abstract).

Varani, Katia et al., "Aberrant A2A receptor function in peripheral blood cells in Huntington's disease," FASEB Journal, 17(14), 2003, pp. 2148–2150. (Abstract).

Kase, H., "New aspects of physiological and pathophysiological functions of adenosine A2A receptor in basal ganglia," Bioscience, Biotechnology, and Biochemistry, 65(7), 2001, pp. 1447–1457. (Abstract).

Ledent, C. et al., "Aggressiveness, hypoalgesia and high blood pressure in mice lacking the adenosine A2a receptor," Nature, 388(6643), Aug. 14, 1997, pp. 674–678. (Abstract).

Bailey, A. et al., "Changes in spinal $\delta$ and $\kappa$ opiod systems in mice deficient in the A2A receptor gene," Journal of Neuroscience, 22(21), 2002, pp. 9210–9220. (Abstract).

Urade, Yoshihiro et al., "Sleep regulation in Adenosine $A_{2A}$ receptor–deficient mice, " Neurology, 61(11Suppl.6), 2003, pp. S94–S96. (Abstract).

Kopf, S. et al., "Adenosine and memory storage: effect of $A_1$ and $A_2$ receptor antagonist," Pyschopharmacology, 146(2), Berlins, 1999, pp. 214–219.

Popoli, P. et al., "Blockade of striatal adenosine A2A receptor reduces, through a presynaptic mechanism, quinolinic acid–induced excitotoxicity: possible relevance to neuroprotective interventions in neurodegenerative diseases of the striatum," Journal of Neuroscience, 22(5), 2002, pp. 1967–1975.

Ikeda, K., et al. "Neuroprotection by adenosine A2A receptor blockade in experimental models of Parkinson's disease," Journal of Neurochemistry, 80(2), 2002, pp. 262–270.

Ongini, E. et al., "Dual actions of A2A adenosine receptor antagonists on motor dysfunction and neurodegenerative processes," Drug Development Research, 52(1/2), 2001, pp. 379–386.

* cited by examiner

THIENO-AND FUROPYRIMIDINE DERIVATIVES AS A2A-RECEPTOR ANTAGONISTS

The present invention relates to novel thieno[3,2-d] pyrimidine and furo[3,2-d]pyrimidine derivatives and their use in therapy. In particular, the present invention relates to the treatment of disorders in which the reduction of purinergic neurotransmission could be beneficial. The invention relates in particular to adenosine receptors and particularly adenosine $A_{2A}$ receptors, and to the treatment of movement disorders such as Parkinson's disease.

Movement disorders constitute a serious health problem, especially amongst the elderly sector of the population. These movement disorders are often the result of brain lesions. Disorders involving the basal ganglia which result in movement disorders include Parkinson's disease, Alzheimer's disease, Huntington's chorea and Wilson's disease. Furthermore, dyskinesias often arise as sequelae of cerebral ischaemia and other neurological disorders.

There are four classic symptoms of Parkinson's disease: tremor, rigidity, akinesia and postural changes. The disease is also commonly associated with depression, dementia and overall cognitive decline. Parkinson's disease has a prevalence of 1 per 1,000 of the total population. The incidence increases to 1 per 100 for those aged over 60 years. Degeneration of dopaminergic neurones in the substantia nigra and the subsequent reductions in interstitial concentrations of dopamine in the striatum are critical to the development of Parkinson's disease. Some 80% of cells from the substantia nigra need to be destroyed before the clinical symptoms of Parkinson's disease are manifested.

Current strategies for the treatment of Parkinson's disease are based on transmitter replacement therapy (L-dihydroxyphenylacetic acid (L-DOPA)), inhibition of monoamine oxidase (e.g. Deprenyl®), dopamine receptor agonists (e.g. bromocriptine and apomorphine) and anticholinergics (e.g. benztrophine, orphenadrine). Transmitter replacement therapy in particular does not provide consistent clinical benefit, especially after prolonged treatment when "on-off" symptoms develop, and this treatment has also been associated with involuntary movements of athetosis and chores, nausea and vomiting. Additionally current therapies do not treat the underlying neurodegenerative disorder resulting in a continuing cognitive decline in patients. Despite new drug approvals, there is still a medical need in terms of improved therapies for movement disorders, especially Parkinson's disease. In particular, effective treatments requiring less frequent dosing, effective treatments which are associated with less severe side-effects, and effective treatments which control or reverse the underlying neurodegenerative disorder, are required.

Blockade of $A_2$ adenosine receptors has recently been implicated in the treatment of movement disorders such as Parkinson's disease (Richardson, P. J. et al., *Trends Pharmacol. Sci.* 1997, 18, 338–344) and in the treatment of cerebral ischaemia (Gao, Y. and Phillis, J. W., *Life Sci.* 1994, 55, 61–65). The potential utility of adenosine $A_{2A}$ receptor antagonists in the treatment of movement disorders such as Parkinson's Disease has recently been reviewed (Mally, J. and Stone, T. W., *CNS Drugs*, 1998, 10, 311–320).

Adenosine is a naturally occurring purine nucleoside which has a wide variety of well-documented regulatory functions and physiological effects. The central nervous system (CNS) effects of this endogenous nucleoside have attracted particular attention in drug discovery, owing to the therapeutic potential of purinergic agents in CNS disorders (Jacobson, K. A. et al., *J. Med. Chem.* 1992, 35, 407–422). This therapeutic potential has resulted in considerable recent research endeavour within the field of adenosine receptor agonists and antagonists (Bhagwhat, S. S.; Williams, M. *Exp. Opin. Ther. Patents* 1995, 5,547–558).

Adenosine receptors represent a subclass ($P_1$) of the group of purine nucleotide and nucleoside receptors known as purinoreceptors. The main pharmacologically distinct adenosine receptor subtypes are known as $A_1$, $A_{2A}$, $A_{2B}$ (of high and low affinity) and $A_3$ (Fredholm, B. B., et al., *Pharmacol. Rev.* 1994, 46, 143–156). The adenosine receptors are present in the CNS (Fredholm, B. B., *News Physiol. Sci.*, 1995, 10, 122–128).

The design of $P_1$ receptor-mediated agents has been reviewed (Jacobson, K. A., Suzuki, F., *Drug Dev. Res.*, 1997, 39, 289–300; Baraldi, P. G. et al., *Curr. Med. Chem.* 1995, 2, 707–722), and such compounds are claimed to be useful in the treatment of cerebral ischemia or neurodegenerative disorders, such as Parkinson's disease (Williams, M. and Burnstock, G. *Purinergic Approaches Exp. Ther.* (1997), 3–26. Editor: Jacobson, Kenneth A.; Jarvis, Michael F. Publisher: Wiley-Liss, New York, N.Y.)

The pharmacology of adenosine $A_{2A}$ receptors has been reviewed (Ongini, E.; Fredholm, B. B. *Trends Pharmacol. Sci.* 1996, 17(10), 364–372). One potential underlying mechanism in the aforementioned treatment of movement disorders by the blockade of $A_2$ adenosine receptors is the evidence of a functional link between adenosine $A_{2A}$ receptors to dopamine $D_2$ receptors in the CNS. Some of the early studies (e.g. Ferre, S. et al., Stimulation of high-affinity adenosine $A_2$ receptors decreases the affinity of dopamine $D_2$ receptors in rat striatal membranes. *Proc. Nal. Acad. Sci. U.S.A.* 1991, 88, 7238–41) have been summarised in two more recent articles (Fuxe, K. et al., *Adenosine Adenine Nucleotides Mol. Biol. Integr. Physiol.*, [Proc. Int. Symp.], 5th (1995), 499–507. Editors: Belardinelli, Luiz; Pelleg, Amir. Publisher: Kluwer, Boston, Mass.; Ferre, S. et al., *Trends Neurosci.* 1997, 20, 482–487).

As a result of these investigations into the functional role of adenosine $A_{2A}$ receptors in the CNS, especially in vivo studies linking $A_2$ receptors with catalepsy (Ferre et al., *Neurosci. Lett.* 1991, 130, 162–4; Mandhane, S. N. et al., *Eur. J. Pharmacol.* 1997, 328, 135–141) investigations have been made into agents which selectively bind to adenosine $A_{2A}$ receptors as potentially effective treatments for Parkinson's disease.

While many of the potential drugs for treatment of Parkinson's disease have shown benefit in the treatment of movement disorders, an advantage of adenosine $A_{2A}$ antagonist therapy is that the underlying neurodegenerative disorder may also be treated. The neuroprotective effect of adenosine $A_{2A}$ antagonists has been reviewed (Ongini, E.; Adami, M.; Ferri, C.; Bertorelli, R., *Ann. N. Y. Acad. Sci.* 1997, 825(Neuroprotective Agents), 30–48).

Xanthine derivatives have been disclosed as adenosine $A_2$ receptor antagonists as useful for treating various diseases caused by hyperfunctioning of adenosine $A_2$ receptors, such as Parkinson's disease (see, for example, EP-A-565377).

One prominent xanthine-derived adenosine $A_{2A}$ selective antagonist is CSC [8-(3-chlorostyryl)caffeine] (Jacobson et al., *FEBS Lett.*, 1993, 323, 141–144).

Theophylline (1,3-dimethylxanthine), a bronchodilator drug which is a mixed antagonist at adenosine $A_1$ and $A_{2A}$ receptors, has been studied clinically. To determine whether a formulation of this adenosine receptor antagonist would be of value in Parkinson's disease an open trial was conducted on 15 Parkinsonian patients, treated for up to 12 weeks with a slow release oral theophylline preparation (150 mg/day), yielding serum theophylline levels of 4.44 mg/L after one week. The patients exhibited significant improvements in mean objective disability scores and 11 reported moderate or marked subjective improvement (Mally, J., Stone, T. W. *J. Pharm. Pharmacol.* 1994, 46, 515–517).

KF 17837 [(E)-8-(3,4-dimethoxystyryl)-1,3-dipropyl-7-methylxanthine] is a selective adenosine $A_{2A}$ receptor antagonist which on oral administration significantly ameliorated the cataleptic responses induced by intracerebroventricular administration of an adenosine $A_{2A}$ receptor agonist, CGS 21680. KF 17837 also reduced the catalepsy induced by haloperidol and reserpine. Moreover, KF 17837 potentiated the anticataleptic effects of a subthreshold dose of L-DOPA plus benserazide, suggesting that KF 17837 is a centrally active adenosine $A_{2A}$ receptor antagonist and that the dopaminergic function of the nigrostriatal pathway is potentiated by adenosine $A_{2A}$ receptor antagonists (Kanda, T. et al., *Eur. J. Pharmacol.* 1994, 256, 263–268). The structure activity relationship (SAR) of KF 17837 has been published (Shimada, J. et al., *Bioorg. Med. Chem. Lett.* 1997, 7, 2349–2352). Recent data has also been provided on the $A_{2A}$ receptor antagonist KW-6002 (Kuwana, Y et al., *Soc. Neurosci. Absir.* 1997, 23, 119.14; and Kanda, T. et al., *Ann. Neurol.* 1998, 43(4), 507–513).

New non-xanthine structures sharing these pharmacological properties include SCH 58261 and its derivatives (Baraldi, P. G. et al., Pyrazolo[4,3-e]-1,2,4-triazolo[1,5-c]pyrimidine Derivatives: Potent and Selective $A_{2A}$ Adenosine Antagonists. *J. Med. Chem.* 1996, 39, 1164–71). SCH 58261 (7-(2-phenylethyl)-5-amino-2-(2-furyl)-pyrazolo-[4,3-e]-1,2,4-triazolo[1,5-c]pyrimidine) is reported as effective in the treatment of movement disorders (Ongini, E. *Drug Dev. Res.* 1997, 42(2), 63–70) and has been followed up by a later series of compounds (Baraldi, P. G. et al., *J. Med. Chem.* 1998, 41(12), 2126–2133).

The foregoing discussion indicates that a potentially effective treatment for movement disorders in humans would comprise agents which act as antagonists at adenosine $A_{2A}$ receptors.

It has now been found that novel thieno[3,2-d]pyrimidine and furo[3,2-d]pyrimidine derivatives, which are structurally unrelated to known adenosine receptor antagonists, exhibit unexpected antagonist binding affinity at adenosine ($P_1$) receptors, and in particular at the adenosine $A_{2A}$ receptor. Such compounds may therefore be useful for the treatment of disorders in which the blocking of purine receptors, particularly adenosine receptors and more particularly adenosine $A_{2A}$ receptors, may be beneficial. In particular such compounds may be suitable for the treatment of movement disorders, such as disorders of the basal ganglia which result in dyskinesias. These may include Parkinson's disease, Alzheimer's disease, spasticity, Huntington's chorea and Wilson's disease.

According to the present invention there is provided a compound of formula (I):

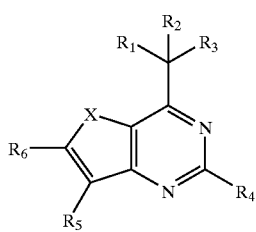

I wherein:

X is O or S;

$R_1$ and $R_2$ are independently selected from hydrogen, alkyl, aryl, hydroxy, alkoxy, aryloxy, cyano, nitro, $CO_2R_7$, $COR_7$, $OCOR_7$, $CONR_7R_8$, $CONR_7NR_8R_9$, $OCONR_7R_8$, $NR_7R_9$, $NR_7COR_8$, $NR_7CONR_8R_9$, $NR_7CO_2R_8$, $NR_7SO_2R_8$, $NR_7CONR_8NR_9R_{10}$, $NR_7NR_8CO_2R_9$, $NR_7NR_8CONR_9R_{10}$, $NR_7SO_2NR_8R_9$, $SO_2R_7$, $SOR_7$, $SR_7$ and $SO_2NR_7R_8$, or $R_1$ and $R_2$ together form a carbonyl group (C=O), an oxime group (C=NOR$_{11}$), an imine group (C=NR$_{11}$) or a hydrazone group (C=NNR$_{11}R_{12}$), or $R_1$ and $R_2$ together form a 5, 6 or 7 membered carbocyclic or heterocyclic ring;

$R_3$ is alkyl or aryl;

$R_4$, $R_5$ and $R_6$ are independently selected from hydrogen, alkyl, aryl, halogen, hydroxy, nitro, cyano, alkoxy, aryloxy, $COR_7$, $OCOR_7$, $CO_2R_7$, $SR_7$, $SOR_7$, $SO_2R_7$, $SO_2NR_7R_8$, $CONR_7R_8$, $CONR_7NR_8R_9$, $OCONR_7R_8$, $NR_7R_8$, $NR_7COR_8$, $NR_7CONR_8R_9$, $NR_7CO_2R_8$, $NR_7SO_2R_8$, $CR_7=NOR_8$, $NR_7CONR_8NR_9R_{10}$, $NR_7NR_8CO_2R_9$, $NR_7NR_8CONR_9R_{10}$, $SO_2NR_7NR_8R_9$, $NR_7SO_2NR_8R_9$, $NR_7NR_8SO_2R_9$, $NR_7NR_8COR_9$, $NR_7NR_8R_9$ and $NR_7CSNR_8R_9$, or $R_5$ and $R_6$ together form a 5, 6 or 7 membered carbocyclic or heterocyclic ring; and $R_7$, $R_8$, $R_9$, $R_{10}$, $R_{11}$ and $R_{12}$ are independently selected from hydrogen, alkyl and aryl, or a pharmaceutically acceptable salt thereof or prodrug thereof.

As used herein, the term "alkyl" means a branched or unbranched, cyclic or acyclic, saturated or unsaturated (e.g. alkenyl or alkynyl) hydrocarbyl radical which may be substituted or unsubstituted. Where cyclic, the alkyl group is preferably $C_3$ to $C_{12}$, more preferably $C_5$ to $C_{10}$, more preferably $C_5$, $C_6$ or $C_7$. Where acyclic, the alkyl group is preferably $C_1$ to $C_{10}$, more preferably $C_1$ to $C_6$, more preferably methyl, ethyl, propyl (n-propyl or isopropyl), butyl (n-butyl, isobutyl or tertiary-butyl) or pentyl (including n-pentyl and iso-pentyl), more preferably methyl. It will be appreciated therefore that the term "alkyl" as used herein includes alkyl (branched or unbranched), alkenyl (branched or unbranched), alkynyl (branched or unbranched), cycloalkyl, cycloalkenyl and cycloalkynyl.

As used herein, the term "lower alkyl" means methyl, ethyl, propyl (n-propyl or isopropyl) or butyl (n-butyl, isobutyl or tertiary-butyl).

As used herein, the term "aryl" means an aromatic group, such as phenyl or naphthyl, or a heteroaromatic group containing one or more heteroatom, such as pyridyl, pyrrolyl, quinolinyl, furanyl, thienyl, oxadiazolyl, thiadiazolyl, thiazolyl, oxazolyl isoxazolyl, pyrazolyl, triazolyl, imidazolyl or pyrimidinyl.

As used herein, the term "alkoxy" means alkyl-O—. As used herein, the term "aryloxy" means aryl-O—.

As used herein, the term "halogen" means a fluorine, chlorine, bromine or iodine radical.

As used herein the term "$R_1$ and $R_2$ together form a carbonyl group, an oxime group, an imine group or a hydrazone group" means that $R_1$ and $R_2$ in combination with the carbon atom to which they are bound together form a carbonyl group, an oxime group, an imine group or a hydrazone group, i.e. the carbon atom to which $R_1$ and $R_2$ are bound in formula (I) is attached via a double bond to an oxygen atom (for compounds wherein $R_1$ and $R_2$ together form a carbonyl group) or to a nitrogen atom (for compounds wherein $R_1$ and $R_2$ together form an oxime, imine or hydrazone group).

As used herein the term "oxime group" means a group of formula C=N—OR$_{11}$ where $R_{11}$ is selected from hydrogen, alkyl and aryl.

As used herein the term "imine group" means a group of formula C=N—R$_{11}$ where $R_{11}$ is selected from hydrogen, alkyl and amyl.

As used herein the term "hydrazone group" means a group of formula C=N—NR$_{11}R_{12}$ where $R_{11}$ and $R_{12}$ arm independently selected from hydrogen, alkyl and aryl.

As used herein, the term "prodrug" means any pharmaceutically acceptable prodrug of a compound of the present invention.

According to the first embodiment of the invention, alkyl and aryl groups may be substituted or unsubstituted. Where substituted, there will generally be 1 to 3 substituents present, preferably 1 substituent. According to the first embodiment of the invention, substituents may include:

carbon-containing groups such as
  alkyl
  aryl, (e.g. substituted and unsubstituted phenyl),
  arylalkyl; (e.g. substituted and unsubstituted benzyl);
halogen atoms and halogen containing groups such as
  haloalkyl (e.g. trifluoromethyl),
  haloaryl (e.g. chlorophenyl);
oxygen containing groups such as
  alcohols (e.g. hydroxy, hydroxyalkyl, hydroxyaryl, (aryl)hydroxy)alkyl),
  ethers (e.g. alkoxy, aryloxy, alkoxyalkyl, aryloxyalkyl, alkoxyaryl aryloxyaryl),
  aldehydes (e.g. carboxaldehyde),
  ketones (e.g. alkylcarbonyl, arylcarbonyl, alkylcarbonylalkyl, alkylcarbonylaryl, arylcarbonylalkyl, arylcarbonylaryl, arylalkylcarbonyl, arylalkylcarbonylalkyl, arylalkylcarbonylaryl)
  acids (e.g. carboxy, carboxyalkyl, carboxyaryl),
  acid derivatives such as esters
    (e.g. alkoxycarbonyl, aryloxycarbonyl, alkoxycarbonylalkyl, aryloxycarbonylalkyl, alkoxycarbonylaryl, aryloxycarbonylaryl, alkylcarbonyloxy, alkylcartonyloxyalkyl), amides
    (e.g. aminocarbonyl, mono- or di-alkylaminocarbonyl, aminocarbonylalkyl, mono- or di-alkylaminocarbonylalkyl, arylaminocarbonyl or arylalkylaminocarbonyl, alkylcarbonylamino, arylcarbonylamino or arylalkylcarbonylamino), carbamates
    (eg. alkoxycarbonylamino, aryloxycarbonylamino, arylalkyloxycarbonylamino, aminocarbonyloxy, mono- or di-alkylaminocarbonyloxy, arylaminocarbonyloxy or arylalkylaminocarbonyloxy) and ureas (eg. mono- or di-alkylaminocarbonylamino, arylaminocarbonylamino or arylalkylaminocarbonylamino);
nitrogen containing groups such as
  amines (e.g. amino, mono- or dialkylamino, arylamino, aminoalkyl, mono- or dialkylaminoalkyl),
  azides,
  nitriles (e.g. cyano, cyanoalkyl),
  nitro;
sulfur containing groups such as
  thiols, thioethers, sulfoxides, and sulfones (e.g. alkylthio, alkylsulfinyl, alkylsulfonyl, alkylthioalkyl, alkylsulfinylalkyl, alkylsulfonylalkyl, arylthio, arylsulfinyl, arylsulfonyl, arylthioalkyl, arylsulfinylalkyl, arylsulfonylalkyl)
and heterocyclic groups containing one or more, preferably one, heteroatom, (e.g. thienyl, furanyl, pyrrolyl, imidazolyl, pyrazolyl, thiazolyl, isothiazolyl, oxazolyl, oxadiazolyl, thiadiazolyl, aziridinyl, azetidinyl, pyrrolidinyl, pyrrolinyl, imidazolidinyl, imidazolinyl, pyrazolidinyl, tetrahydrofuranyl, pyranyl, pyronyl, pyridyl, pyrazinyl, pyridazinyl, piperidyl, hexahydroazepinyl, piperazinyl, morpholinyl, thianaphthyl, benzofuranyl, isobenzofuranyl, indolyl, oxyindolyl, isoindolyl, indazolyl, indolinyl, 7-azaindolyl, benzopyranyl, coumarinyl, isocoumarinyl, quinolinyl, isoquinolinyl, naphthridinyl, cinnolinyl, quinazolinyl, pyridopyridyl, benzoxazinyl, quinoxalinyl, chromenyl, chromanyl, isochromanyl, phthalazinyl and carbolinyl).

According to the second embodiment of the invention, alkyl and aryl groups may be substituted or unsubstituted. Where substituted, there will generally be 1 to 3 substituents present, preferably 1 substituent. According to the second embodiment of the invention, the substituent groups are selected from:

carbon containing groups such as
  alkyl,
  aryl,
  arylalkyl (e.g. substituted and unsubstituted phenyl, substituted and unsubstituted benzyl);
halogen atoms and halogen containing groups such as
  haloalkyl (e.g. trifluoromethyl);
oxygen containing groups such as
  alcohols (e.g. hydroxy, hydroxyalkyl, aryl(hydroxy)alkyl),
  ethers (e.g. alkoxy, alkoxyalkyl, aryloxyalkyl),
  aldehydes (e.g. carboxaldehyde),
  ketones (e.g. alkylcarbonyl, alkylcarbonylalkyl, arylcarbonyl, arylalkylcarbonyl, arylcarbonylalkyl)
  acids (e.g. carboxy, carboxyalkyl),
  acid derivatives such as esters (e.g. alkoxycarbonyl, alkoxycarbonylalkyl, alkylcarbonyloxy, alkylcarbonyloxyalkyl)
  and amides (e.g. aminocarbonyl, mono- or dialkylaminocarbonyl, aminocarbonylalkyl, mono- or dialkylaminocarbonylalkyl, arylaminocarbonyl);
nitrogen containing groups such as
  amines (e.g. amino, mono- or dialkylamino, aminoalkyl, mono- or dialkylaminoalkyl),
  azides,
  nitriles (e.g. cyano, cyanoalkyl),
  nitro;
sulfur containing groups such as
  thiols, thioethers, sulfoxides, and sulfones (e.g. alkylthio, alkylsulfinyl, alkylsulfonyl, alkylthioalkyl, alkylsulfinylalkyl, alkylsulfonylalkyl, arylthio, arylsulfinyl, arylsulfonyl, arylthioalkyl, arylsulfinylalkyl, arylsulfonylalkyl);
and heterocyclic groups containing one or more, preferably one, heteroatom (e.g. thienyl, furanyl, pyrrolyl, imidazolyl, pyrazolyl, thiazolyl, isothiazolyl, oxazolyl, pyrrolidinyl, pyrrolinyl, imidazolidinyl, imidazolinyl, pyrazolidinyl, tetrahydrofuranyl, pyranyl, pyronyl, pyridyl, pyrazinyl, pyridazinyl, piperidyl, piperazinyl, morpholinyl, thianaphthyl, benzofuranyl, isobenzofuranyl, indolyl, oxyindolyl, isoindolyl, indazolyl, indolinyl, 7-azaindolyl, benzopyranyl, coumarinyl, isocoumarinyl, quinolinyl, isoquinolinyl, naphthridinyl, cinnolinyl, quinazolinyl, pyridopyridyl, benzoxazinyl, quinoxalinyl, chromenyl, chromanyl, isochromanyl, phthalazinyl and carbolinyl).

According to the third embodiment of the invention, where any of $R_1$ to $R_{12}$ is selected from alkyl and alkoxy, in accordance with formula (I) as defined above, then that alkyl group, or the alkyl group of the alkoxy group, may be substituted or unsubstituted. Where any of $R_1$ to $R_{12}$ are selected from aryl and aryloxy, in accordance with formula (I) as defined above, then said aryl group, or the aryl group of the aryloxy group, may be substituted or unsubstituted.

Where $R_1$ and $R_2$ together form a carbocyclic or heterocyclic ring, or $R_5$ and $R_6$ together form a carbocyclic or heterocyclic ring, in accordance with formula (I) as defined above, then that carbocyclic or heterocyclic ring may be substituted or unsubstituted. Where substituted, there will generally be 1 to 3 substituents present, preferably 1 substituent. In the third embodiment of the invention, the substituents are those defined in respect of the second embodiment of the invention described above.

According to the fourth embodiment of the invention, where any of $R_1$ to $R_{12}$ is selected from alkyl and alkoxy, in accordance with formula (I) as defined above, then that alkyl group, or the alkyl group of the alkoxy group, may be substituted or unsubstituted. Where any of $R_1$ to $R_{12}$ are selected from aryl and aryloxy, in accordance with formula (I) as defined above, then said aryl group, or the aryl group of the aryloxy group, may be substituted or unsubstituted. Where $R_1$ and $R_2$ together form a carbocyclic or heterocyclic ring, or $R_5$ and $R_6$ together form a carbocyclic or heterocyclic ring, in accordance with formula (I) as defined above, then that carbocyclic or heterocyclic ring may be substituted or unsubstituted. Where substituted, there will generally be 1 to 3 substituents present, preferably 1 substituent. In the fourth embodiment of the invention, the substituents may include those defined in respect of the first embodiment of the invention described above.

According to the fifth embodiment of the invention, the compounds are selected from compounds of formula (Ia):

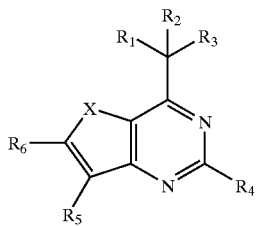

(Ia)

wherein X, $R_1$ to $R_3$ and $R_5$ to $R_{12}$ are as defined for formula (I) above;

$R_4$ is selected from hydrogen, alkyl, aryl, halogen, hydroxy, nitro, cyano, alkoxy, aryloxy, $COR_7$, $OCOR_7$, $CO_2R_7$, $SR_7$, $SOR_7$, $SO_2R_7$, $SO_2NR_7R_8$, $CONR_7R_8$, $CONR_7NR_8R_9$, $CONR_7YNR_8R_9$, $OCONR_7R_8$, $NR_7R_8$, $NR_7YR_8$, $NR_7COR_8$, $NR_7CONR_8R_9$, $NR_7ZCONR_8R_9$, $NR_7CO_2R_8$, $NR_7ZCO_2R_8$, $N(COR_8)COR_9$, $NR_7SO_2R_8$, $CR_7{=}NOR_8$, $NR_7CONR_8N_9R_{10}$, $NR_7CONR_8YNR_9R_{10}$, $NR_7NR_8COR_9$, $NR_7YNR_8C_2R_9$, $NR_7NR_8CONR_9R_{10}$, $NR_7YNR_8CONR_9R_{10}$, $SO_2NR_7NR_8R_9$, $SO_2NR_7YNR_8R_9$, $NR_7SO_2NR_8SR_9$, $NR_7NR_8O_2R_9$, $NR_7YNR_8SO_2R_9$, $NR_7NR_8COR_9$, $NR_7YNR_8COR_9$, $NR_7NR_8R_9$, $NR_7YNR_8R_9$, $NR_7CSNR_8R_9$, $NR_7YNR_8CSNR_9R_{10}$ and $NR_7YNR_8CONR_9YNR_{10}R_{11}$);

Y is a divalent $C_2$ to $C_4$ carbon chain; and

Z is a divalent $C_1$ to $C_4$ carbon chain, or a pharmaceutically acceptable salt thereof or prodrug thereof.

In the fifth embodiment of the invention, where any of $R_1$ to $R_{12}$ is selected from alkyl and alkoxy, in accordance with formula (Ia) as defined above, then that alkyl group, or the alkyl group of the alkoxy group, may be substituted or unsubstituted. Where any of $R_1$ to $R_{12}$ are selected from aryl and aryloxy, in accordance with formula (Ia) as defined above, then said aryl group, or the aryl group of the aryloxy group, may be substituted or unsubstituted. Where $R_1$ and $R_2$ together form a carbocyclic or heterocyclic ring, or $R_5$ and $R_6$ together form a carbocyclic or heterocyclic ring, in accordance with formula (Ia) as defined above, then that carbocyclic or heterocyclic ring may be substituted or unsubstituted. Where substituted, there will generally be 1 to 3 substituents present, preferably 1 substituent. In the fifth embodiment of the invention, the substituents may include those defined in respect of the first embodiment of the invention described above.

As used herein, the term "divalent $C_1$ to $C_4$ carbon chain" means a chain comprising 1, 2, 3 or carbon atoms, branched or unbranched, and saturated or unsaturated.

As used herein, the term "divalent $C_2$ to $C_4$ carbon chain" means a chain comprising 2, 3 or 4 carbon atoms, branched or unbranched, and saturated or unsaturated.

In the compounds of the present invention, preferably X is S.

In a preferred embodiment of the invention, $R_1$ and $R_2$ are independently selected from hydrogen; hydroxy; cyano; alkyl, preferably hydroxy-substituted alkyl; and $CO_2R_7$, wherein preferably $R_7$ is alkyl. In this embodiment, it is preferred that $R_1$ and $R_2$ are selected from hydrogen and cyano. In this embodiment, it is preferred that one of $R_1$ and $R_2$ is hydrogen.

In a further embodiment, where $R_1$ is hydroxy, $R_2$ is not selected from hydroxy, alkoxy and aryloxy. Similarly, where $R_2$ is hydroxy, it is preferred that $R_1$ is not selected from hydroxy, alkoxy and aryloxy.

In an alternative further embodiment, where $R_1$ is selected from hydroxy and SH, $R_2$ is not selected from hydroxy, alkoxy, aryloxy and $SR_7$. Similarly, where $R_2$ is selected from hydroxy and SH, it is preferred that $R_1$ is not selected from hydroxy, alkoxy, aryloxy and $SR_7$.

In a preferred embodiment, $R_1$ and $R_2$ together form a carbonyl group or an oxime group, preferably a carbonyl group. Where $R_1$ and $R_2$ together form an oxime group $C{=}N{-}OR_{11}$, it is preferred that $R_{11}$ is hydrogen In a particularly preferred embodiment of the invention, $R_1$ and $R_2$ together form a carbonyl group.

In the compounds of the present invention, it is preferred that $R_3$ is aryl, preferably comprising a five or six membered ring which may be substituted or unsubstituted and which may be carbocyclic or heterocyclic. It is preferred that $R_3$ is monocyclic.

Where $R_3$ is a five-membered ring, it is preferred that $R_3$ is an N, O or S-containing heterocyclic ring, preferably a thienyl, furyl pyrrolyl or thiazolyl group, more preferably a thienyl group. Where $R_3$ is a six-membered ring it is preferred that $R_3$ is phenyl or an N-containing heterocyclic ring, preferably pyridyl.

Where $R_3$ is substituted, it is preferred that $R_3$ is substituted by substituent group(s) selected from halogen, preferably fluoro, chloro and bromo, more preferably chloro; lower alkyl, preferably methyl; lower alkoxy, preferably methoxy; nitro; and amino, preferably dialkylamino, more preferably dimethylamino.

In a particularly preferred embodiment, $R_3$ is selected from thienyl, furyl, pyridyl (preferably 2-pyridyl) and phenyl, preferably 2-thienyl. Where $R_3$ is selected from 2-thienyl, the 2-thienyl group is preferably unsubstituted or substituted by lower alkyl (preferably methyl) or halogen (preferably chloro or bromo, preferably chloro) or lower alkoxy preferably methoxy), and more preferably is unsubstituted or substituted by lower alkyl (preferably methyl), and is more preferably unsubstituted. Where $R_3$ is selected from furyl, the furyl group is preferably a 2-furyl group and is preferably unsubstituted or substituted by lower alkyl (preferably methyl).

In the compounds of the present invention, preferably $R_5$ is selected from hydrogen, alkyl, halogen, hydroxy, nitro, cyano, alkoxy, aryloxy, $COR_7$, $OCOR_7$, $CO_2R_7$, $SR_7$, $SOR_7$, $SO_2R_7$, $SO_2NR_7R_9$, $CONR_7R_9$, $CONR_7NR_8R_9$, $OCONR_7R_8$, $NR_7R_8$, $NR_7COR_8$, $NR_7CONR_8R_9$, $NR_7CO_2R_8$, $NR_7SO_2R_8$, $CR_7=NOR_8$, $NR_7CONR_8NR_9R_{10}$, $NR_7NR_8CO_2R_9$, $NR_7NR_8CONR_9R_{10}$, $SO_2NR_7NR_8R_9$, $NR_7SO_2NR_9R_9$, $NR_7NR_8SO_2R_9$, $NR_7NR_8COR_9$, $NR_7NR_8R_9$, $NR_7CSNR_8R_9$, or together with $P_6$ forms a 5, 6 or 7 membered carbocyclic or heterocyclic ring.

In one embodiment of the present invention, $R_5$ is selected from hydrogen, halogen, alkyl and aryl.

Where $R_5$ is selected from aryl, it is preferred that $R_5$ is an aryl group other than phenyl or an N-containing heteroaromatic group, particularly pyridyl, pyrazinyl pyrimidinyl and pyridazinyl. Where $R_5$ is an aryl group, it is preferred that $R_5$ is an aryl group selected from an O— or S-containing heterocyclic ring, preferably an O-containing ring, and preferably a 5-membered heterocyclic ring, preferably furanyl or thienyl, and more preferably furanyl.

In the compounds of the present invention, preferably $R_5$ is selected from hydrogen, halogen and alkyl, and preferably $R_5$ is hydrogen.

In the compounds of the present invention, it is preferred that $R_6$ is selected from hydrogen, alkyl, aryl and halogen, and preferably $R_6$ is hydrogen.

It is preferred that at least one, and preferably both of $R_5$ and $R_6$ are hydrogen. Where $R_5$ and/or $R_6$ are selected from alkyl, it is preferred that $R_5$ and/or $R_6$ are methyl.

Where any of $R_1$, $R_2$, or $R_4$ to $R_6$ are independently selected from $NR_7CO_2R_8$, it is preferred that $R_9$ is selected from alkyl and aryl.

Where any of $R_1$, $R_2$ or $R_4$ to $R_6$ are independently selected from $NR_7NR_8CO_2R_9$, it is preferred that $R_9$ is selected from alkyl and aryl.

Where $R_4$ is selected from $NR_7YNR_8CO_2R_9$, it is preferred that $R_9$ is selected from alkyl and aryl.

In the compounds of the present invention where $R_4$ is an $NR_7R_8$ group, the $R_7$ and $R_8$ groups may together form a ring to produce a cyclic amino group. The cyclic amino group is a saturated or partially unsaturated cyclic group (i.e. it is non-aromatic), and is preferably a saturated cyclic amino group. The cyclic amino group is preferably a 5-, 6- or 7-membered and is preferably a 5- or 6-membered cyclic amino group. Where partially unsaturated, it is preferred that only 1 double bond is present. The cyclic amino group may contain one or more additional heteroatoms, preferably one or two heteroatoms, wherein the heteroatoms are preferably selected from N, O and S and preferably from N and O. The cyclic amino groups may be substituted or unsubstituted, preferably substituted. Where substituted, there will generally be 1 to 3 substituents present, preferably 1 substituent. Substituents may include any of those set out above in respect of the first and second embodiments. Preferably the cyclic amino groups are selected from pyrrolidinyl pyrrolidinonyl, piperidinyl, piperazinyl and morpholinyl groups, more preferably from pyrrolidinyl, piperidinyl, piperazinyl and morpholinyl groups, and particularly from pyrrolidinyl groups (preferably substituted and preferably substituted by hydroxy, lower alkyl or hydroxy(lower alkyl)).

In one embodiment of the present invention, $R_4$ is preferably selected from alkyl (including trifluoromethyl); halogen (preferably chloro); alkoxy (preferably methoxy or ethoxy); $SR_7$ (preferably alkylthio, preferably methylthio); dialkylamino (preferably dimethylamino); and monoalkylamino, wherein said alkyl groups are substituted or unsubstituted. In this embodiment, preferably $R_4$ is unsubstituted alkyl, trifluoromethyl or monoalkylamino (wherein the alkyl groups are substituted or unsubstituted), and more preferably monoalkylamino (preferably $NR_7R_8$ wherein $R_7$ is hydrogen, and $R_8$ is substituted or unsubstituted). In this embodiment, where $R_4$ is monoalkylamino or dialkylamino, the alkyl group(s) may be substituted as described above, for instance, by hydroxy, alkoxy, amino or dialkylamino.

Where $R_4$ is alkyl, it is preferred that $R_4$ is unsubstituted alkyl (preferably saturated alkyl, preferably lower alkyl) or halo-substituted alkyl (preferably trifluoromethyl).

In a particularly preferred embodiment of the invention, $R_4$ is $NR_7R_8$. Where $R_4$ is $NR_7R_8$, it is preferred that $R_7$ is lower alkyl or hydrogen, and preferably hydrogen. Preferably, $R_8$ is lower alkyl (substituted or unsubstituted and, where substituted, is preferably substituted by hydroxy, alkoxy, a saturated heterocyclic group or aryl (particularly heteroaryl)), cyclic alkyl or aryl.

In a further preferred emdbodment, $R_4$ is $NH_2$.

Where $R_4$ is $NR_7NR_8R_9$, it is preferred that $R_7$ is hydrogen. Preferably $R_5$ and $R_9$ are also hydrogen.

In the compounds of formula (I), preferably $R_4$ is selected from aklyl (including trifluoromethyl); halogen (preferably chloro); alkoxy (preferably methoxy or ethoxy, $SR_7$ (preferably methylthio); and a substituted amino group (preferably $NR_7R_8$, $NR_7N_8COR_9$, $NR_7NR_8CO_2R_9$, $NR_7CO_2R_8$, $NR_7NR_8CONR_9R_{10}$, $NR_7NR_8SO_2R_9$, $NR_7N_8CSNR_9R_{10}$, $NR_7NR_8R_9$ and $NR_7COR_8$, and more preferably $NR_7R_8$). Preferably $R_4$ is a substituted amino group or alkyl. Most preferably $R_4$ is a substituted amino group, preferably $NR_7R_8$ wherein $R_7$ is hydrogen:

In the compounds of formula (Ia), preferably $R_4$ is selected from alkyl (including trifluoromethyl); halogen (preferably chloro); alkoxy (preferably methoxy or ethoxy, $SR_7$ (preferably methylthio); and a substituted amino group (preferably $NR_7R_8$, $NR_7YR_8$, $NR_7YNR_8COR_9$, $NR_7YNR_8CO_2R_9$, $NR_7ZCO_2R_8$, $NR_7YNR_8CONR_9R_{10}$, $NR_7YNR_8SO_2R_9$, $NR_7YNR_8CSNR_9R_{10}$, $NR_7NR_8R_9$ and $N(COR_8)COR_9$, and more preferably $NR_7R_8$). Preferably $R_4$ is a substituted amino group or alkyl. Most preferably $R_4$ is a substituted amino group, as detailed below.

In the compounds of formulae (I) or (Ia), in a preferred embodiment where $R_4$ is selected from $NR_7R_8$, it is preferred that $R_7$ is hydrogen or alkyl, and preferably hydrogen, and $R_8$ is selected from alkyl (preferably saturated alkyl), preferably lower alkyl (preferably saturated lower alkyl), substituted or unsubstituted and preferably substituted, wherein the preferred substituent groups on $R_8$ are selected from aryl (preferably thienyl, furyl, pyridyl and phenyl); oxygen-containing groups, particularly alcohols (preferably hydroxy), ethers (preferably alkoxy); acids (preferably carboxy); acid derivatives (particularly (esters preferably alkoxycarbonyl), amides (preferably alkylcarbonylamino and arylcarbonylamino), carbamates (preferably alkoxycarbonylamino and arylalkoxycarbonylamino) and ureas (preferably alkylaminocarbonylamino, arylaminocarbonylamino and arylalkylaminocarbonylamino); nitrogen-containing groups, particularly amines and thioureas; and saturated heterocyclic groups, particularly N- and O-containing groups (preferably tetrahydrofuranyl, pyrrolidinyl, pyrrolidinonyl, piperidinyl, piperazinyl and morpholinyl groups).

In the compounds of formulae (I) or (Ia), in an alternative preferred embodiment where $R_4$ is selected from $NR_7R_8$, it is preferred that $R_7$ is hydrogen or alkyl and preferably hydrogen, and $R_8$ is selected from alkyl (preferably saturated alkyl), preferably lower alkyl (preferably saturated lower alkyl), substituted or unsubstituted and preferably substituted, wherein the preferred substituent groups on $R_8$ are selected from aryl (preferably phenyl); oxygen-containing groups, alcohols (preferably hydroxy), ethers (preferably alkoxy) and acid derivatives, particularly esters (preferably alkoxycarbonyl) and carbamates (preferably alkoxycarbonylamino); nitrogen containing groups, particularly amines; and heterocyclic groups, particularly saturated N-containing heterocyclic groups (preferably pyrrolidinyl, pyrrolidinonyl, piperidinyl, piperazinyl and morpholinyl groups).

In the compounds of formula (Ia) where $R_4$ is $NR_7YNR_8COR_9$, it is preferred that $R_7$ is hydrogen. Preferably $R_8$ is also hydrogen. Preferably $R_9$ is selected from lower alkyl, cyclic alkyl and aryl (preferably substituted or unsubstituted phenyl or thienyl).

In the compounds of formula (Ia) where $R_4$ is $NR_7YNR_8CO_2R_9$ or $NR_7YNR_8SO_2R_9$, it is preferred that $R_7$ is hydrogen. Preferably $R_8$ is also hydrogen. It is preferred that $R_9$ is selected from lower alkyl (substituted or unsubstituted and, where substituted, preferably substituted by halogen (preferably chloro) or aryl).

In the compounds of formula (Ia) where $R_4$ is $NR_7YNR_8CONR_9R_{10}$ or $NR_7YNR_8CSNR_9R_{10}$, it is preferred that $R_7$ is hydrogen. Preferably $R_8$ and $R_9$ are also hydrogen. It is preferred that $R_{10}$ is lower alkyl (substituted or unsubstituted), cyclic alkyl or aryl.

In the compounds of formula (Ia) where $R_4$ is $NR_7ZCO_2R_8$, preferably $R_7$ is hydrogen and $R_8$ is selected from hydrogen and lower alkyl, and preferably from lower alkyl.

In the compounds of formula (Ia) where $R_4$ is $NR_7YR_8$, it is preferred that $R_7$ is hydrogen. $R_8$ is aryl, preferably substituted by lower alkyl, lower alkoxy and nitro.

In the compounds of formula Ia) where $R_4$ is $N(COR_8)COR_9$, it is preferred that $R_8$ and $R_9$ are independently selected from lower alkyl.

In the compounds of formula (Ia), preferably Y is a saturated (alkylene) $C_2$ to $C_4$ carbon chain and is preferably unbranched. Preferably, Y is a $C_2$ or $C_3$ carbon chain, preferably a $C_2$ carbon chain. Preferably, Y is a divalent $CH_2CH_2$ radical.

In the compounds of formula (Ia), preferably Z is a saturated (alkylene) $C_1$ to $C_4$ carbon chain and is preferably unbranched. Preferably, Z is a $C_1$, $C_2$ or $C_3$ carbon chain, preferably a $C_2$ carbon chair Preferably, Z is a divalent $CH_2CH_2$ radical.

In a particularly preferred embodiment of the invention, the compounds of the present invention are selected from:
(2R)-2-(1-Hydroxy-2-propylamino)thieno[3,2-d]pyrimidin-4-yl 2-thienylmethanone,
2-(3-(1H-Imidazol-1-yl)propylamino)thieno[3,2-d]pyrimidin-4-yl 2-thienylmethanone,
(2RS)-2-(1-Hydroxy-2-propylamino)thieno[3,2-d]pyrimidin-4-yl 2-thienylmethanone,
2-(3-Hydroxypropylamino)thieno[3,2-d]pyrimidin-4-yl 2-thienylmethanone,
3-Methyl-N-(2-(4-(2-thienylcarbonyl)thieno[3,2-d]pyrimidin-2-yl)aminoethyl)butanamide,
Methyl (2-(4-(2-thienylcarbonyl)thieno[3,2-d]pyrimidin-2-yl)aminoethyl)carbamate,
2-(2-(1H-Imidazol-4-yl)ethylamino)thieno[3,2-d]pyrimidin-4-yl 2-thienylmethanone,
(2RS)-2-(2,3-Dihydroxypropylamino)thieno[3,2-d]pyrimidin-4-yl 2-thienylmethanone,
(2R)-2-(2-Hydroxypropylamino)thieno[3,2-d]pyrimidin-4-yl 2-thienylmethanone,
2-(2-Hydroxyethylamino)thieno[3,2-d]pyrimidin-4-yl 3-methyl-2-thienylmethanone,
2-Chloroethyl (2-(4-(2-thienylcarbonyl)thieno[3,2d]pyrimidin-2-yl)aminoethyl)carbamate,
(2S)-2-(1-Hydroxy-2-propylamino)thieno[3,2-d]pyrimidin-4-yl 2-thienylmethanone,
2-(3-(1H-Imidazol-1-yl)propylamino)thieno[3,2-d]pyrimidin-4-yl 3-methyl-2-thienylmethanone,
N-(2-(4-(2-Thienylcarbonyl)thieno[3,2-d]pyrimidin-2-yl)aminoethyl)cyclohexylcarboxamide,
Ethyl 4-(4-(2-thienylcarbonyl)thieno[3,2-d]pyrimidin-2-ylamino)butanoate,
2-(2-Pyridylmethylamino)thieno[3,2-d]pyrimidin-4-yl 2-thienylmethanone,
(2S)-2-(2-Hydroxypropylamino)thieno[3,2-d]pyrimidin-4-yl 2-thienylmethanone,
N-Allyl-N'-(2-(4-(2-thienylcarbonyl)thieno[3,2-d]pyrimidin-2-yl)aminoethyl)urea,
N-(2-(4-(2-Thienylcarbonyl)thieno[3,2-d]pyrimidin-2-yl)aminoethyl)acetamide,
2-(Tetrahydrofuran-2-ylmethylamino)thieno[3,2-d]pyrimidin-4-yl 2-thienylmethanone,
N-Benzyl-N'-2-(4-(2-thienylcarbonyl)thieno[3,2-d]pyrimidin-2-yl)aminoethyl)urea,
2-(2-Hydroxyethylamino)thieno[3,2-d]pyrimidin-4-yl 2-thienylmethanone,
Benzyl (2-(4-(2-thienylcarbonyl)thieno[3,2-d]pyrimidin-2-yl)aminoethyl)carbamate, and
2-Aminothieno[3,2-d]pyrimidin-4-yl 2-thienylmethanone.

In an alternative embodiment, the compounds of the present invention are selected from:
2-thienyl 2-trifluoromethylthieno[3,2-d]pyrimidin-4-ylmethanone,
2-(2-hydroxyethyl)aminothieno[3,2-d]pyrimidin-4-yl 2-thienylmethanone,
2-ethylaminothieno[3,2-d]pyrimidin-4-yl 2-thienylmethanone,
2-ethylthieno[3,2-d]pyrimidin-4-yl 2-thienylmethanone,
2-methylaminothieno[3,2-d]pyrimidin-4-yl 2-thienylmethanone, and
2-(2-methoxyethylamino)thieno[3,2-d]pyrimidin-4-yl 2-thienylmethanone.

Where chiral the compounds of the present invention may be in the form of a racemic mixture of pairs of enantiomers or in enantiomerically pure form.

According to a further aspect of the invention, there is provided for use in therapy a compound of the present invention, or a pharmaceutically acceptable salt or prodrug thereof.

The present invention may be employed in respect of a human or animal subject, more preferably a mammal, more preferably a human subject The disorders of particular interest are those in which the blocking of purine receptors, partiucularly adenosine receptors and more particularly adenosine $A_{2A}$ receptors, may be beneficial. These may include movement disorders such as Parkinson's disease, drug-induced Parkinsonism, post-encephalitic Parkinsonism, Parkinsonism induced by poisoning (for example MPTP, manganese, carbon monoxide) and post-traumatic Parkinson's disease (punch-drunk syndrome).

Other movement disorders in which the blocking of purine receptors, may be of benefit include progressive supernuclear palsy, Huntingtons disease, multiple system atrophy, corticobasal degeneration, Wilsons disease, Hallerrorden-Spatz disease, progressive pallidal atrophy, Dopa-responsive dystonia-Parkinsonism, spasticity or other disorders of the basal ganglia which result in abnormal movement or posture. The present invention may also be effective in treating Parkinson's with on-off phenomena; Parkinson's with freezing (end of dose deterioration); and Parkinson's with prominent dyskinesias.

The compounds of the present invention may be used or administered in combination with one or more additional drugs useful in the treatment of movement disorders, such as L-DOPA, the components being in the same formulation or in separate formulations for administration simultaneously or sequentially.

Other disorders in which the blocking of purine receptors, particularly adenosine receptors and more particularly adenosine $A_{2A}$ receptors may be beneficial include acute and chronic pain; for example neuropathic pain, cancer pain, trigeminal neuralgia, migraine and other conditions associated with cephalic pain, primary and secondary hyperalgesia, inflammatory pain, nociceptive pain, tabes dorsalis, phantom limb pain, spinal cord injury pain, central pain, post-herpetic pain and HIV pain; affective disorders including mood disorders such as bipolar disorder, seasonal affective disorder, depression, manic depression, atypical depression and monodepressive disease; central and peripheral nervous system degenerative disorders including corticobasal degeneration, demyelinating disease (multiple sclerosis, disseminated sclerosis), Freidrich's ataxia, motoneurone disease (amyotrophic lateral sclerosis, progressive bulbar atrophy), multiple system atrophy, myelopathy, radiculopathy, peripheral neuropathy (diabetic neuropathy, tabes dorsalis, drug-induced neuropathy, vitamin deficiency), systemic lupus erythamatosis, granulomatous disease, olivo-ponto-cerebellar atrophy, progressive pallidal atrophy, progressive supranuclear palsy, spasticity; cognitive disorders including dementia, Alzheimers Disease, Frontotemporal dementia, multi-infarct dementia, AIDS dementia, dementia associated with Huntingtons Disease, Lewy body dementia, senile dementia, age-related memory impairment, cognitive impairment associated with dementia, Korsakoff syndrome, dementia pugilans; central nervous system injury including traumatic brain injury, neurosurgery (surgical trauma), neuroprotection for head injury, raised intracranial pressure, cerebral oedema, hydrocephalus, spinal cord injury; cerebral ischaemia including transient ischaemic attack, stroke (thrombotic stroke, ischaemic stroke, embolic stroke, haemorrhagic stroke, lacunar stroke) subarachnoid haemorrhage, cerebral vasospasm, neuroprotection for stroke, peri-natal asphyxia, drowning, cardiac arrest, subdural haematoma; myocardial ischaemia; muscle ischaemia; sleep disorders such as hypersomnia; eye disorders such as retinal ischaemia-reperfusion injury and diabetic neuropathy; cardiovascular disorders such as claudication; and diabetes and it's complications.

According to a ether aspect of the present invention, there is provided the use of a compound of the present invention or a pharmaceutically acceptably salt or prodrug thereof in the manufacture of a medicament for the treatment or prevention of a disorder in which the blocking of purine receptors, particularly adenosine receptors and more particularly $A_{2A}$ receptors, may be beneficial.

According to a further aspect of the present invention there is provided a method of treating or preventing a disorder in which the blocking of purine receptors, particularly adenosine receptors and more particularly adenosine $A_{2A}$ receptors, may be beneficial, the method comprising administration to a subject in need of such treatment an effective dose of a compound of the present invention or a pharmaceutically acceptable salt or prodrug thereof.

The disorder may be caused by the hyperfunctioning of the purine receptors.

According to a further aspect of the present invention there is provided use of a compound of the present invention or a pharmaceutically acceptable salt or prodrug thereof in the manufacture of a medicament for the treatment or prevention of movement disorders in a subject.

According to a further aspect of the invention there is provided a method of treating or preventing movement disorders comprising administration to a subject in need of such treatment an effective dose of a compound of the present invention or a pharmaceutically acceptable salt or prodrug thereof.

According to a further aspect of the invention there is provided use of a compound of the present invention or a pharmaceutically acceptable salt or prodrug thereof in the manufacture of a medicament for neuroprotection in a subject.

According to a further aspect of the invention there is provided a method of neuroprotection comprising administration to a subject in need of such treatment an effective dose of a compound of the present invention or a pharmaceutically acceptable salt or prodrug thereof.

The medicament for or method of neuroprotection may be of use in the treatment of subjects who are suffering from or at risk from a neurodegenerative disorder, such as a movement disorder.

According to a further aspect of the invention, there is provided a method of preparing the novel compounds of the present invention. Compounds of the present invention (according to formula (I) or formula (Ia)) may be prepared according to conventional synthetic methods, such as set out in Reaction Scheme 1.

Reaction Scheme 1

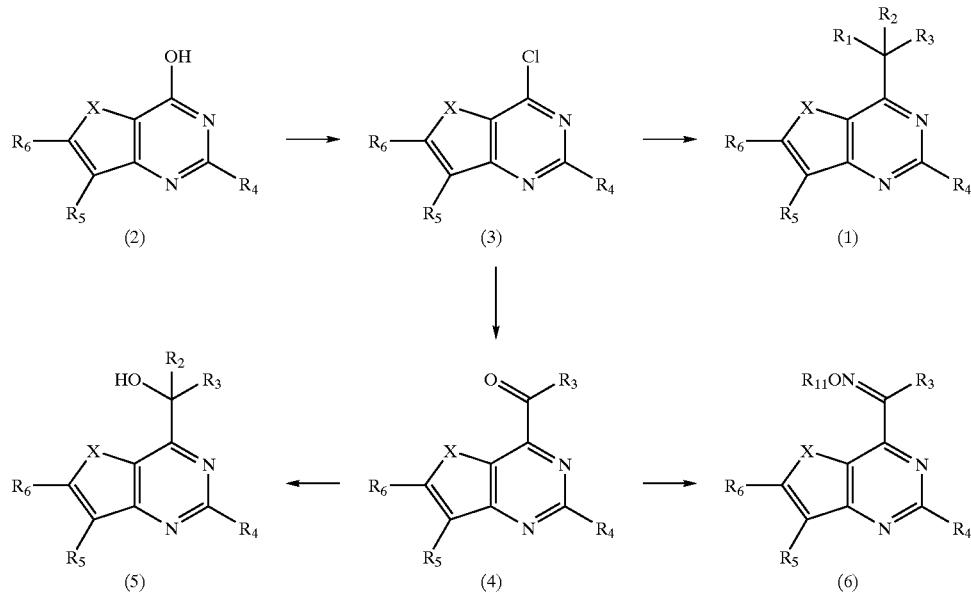

Alcohols (5) are prepared from ketones (4) either by reduction using standard methods such as NaBH$_4$ (where R$_2$ is H) or by addition of, for example, Grignard reagents (where R$_2$ is alkyl or aryl). Ketones (4) are prepared from chloro compounds (3) by known methods such as the addition of the appropriate aldehyde R$_3$CHO and a base such as NaH in the presence of a catalyst such as N,N-dimethylimidazolium iodide (Miyashita A. et al., *Heterocycles*, 1997, 45, 2159–2173). Chloro compounds (3) are either known or are prepared from alcohols (2) by standard methods such as treatment with POCl$_3$. Alcohols (2) are either known compounds or may be prepared by standard literature methods. Compounds of formula (3) where R$_4$ is a chloro group are either known or are prepared from compounds of formula (2) where R$_4$ is a hydroxy group by standard methods such as treatment with POCl$_3$. Compounds of formula (2) where R$_4$ is a hydroxy group are either known or are prepared by standard literature methods.

Oximes (6) are prepared from ketones (4) by standard methods such as treatment with the appropriate hydroxylamine in the presence of a base such as pyridine.

Compounds of formula (1) where R$_1$ is a nitrile, alkoxycarbonyl, nitro, sulphonyl or amide group are prepared from chloro compounds (3) by standard methods such as the addition of a compound of formula HCR$_1$R$_2$R$_3$, where R$_1$ is a nitrile, alkoxycarbonyl, nitro, sulphonyl or amide group, in the presence of a base such as NaH.

Compounds of formula (1) where R$_1$ is a hydroxymethyl group are prepared from compounds of formula (1) where R$_1$ is an alkoxycarbonyl group by standard methods such as reduction with, for example, DIBAL.

Compounds of formula (1) where R$_4$ is an alkoxy, aryloxy, hydroxy, alkylthio, arylthio, amino, mono or dialkylamino, cyano, carboxamido or substituted or unsubstituted hydrazino group may be prepared from compounds of formula (1) where R$_4$ is a halogen by standard methods such as reaction with the appropriate nucleophile. Appropriate nucleophiles would include for example alkoxides, aryloxides, hydroxide, alkylthiolates, arylthiolates, ammonia, mono or dialkylamines, cyanide, carboxamide salts, hydrazine and substituted hydrazines. Alternatively compounds of formula (1) where R$_4$ is an amino group may be prepared from compounds of formula (1) where R$_4$ is a halogen by standard methods such as reaction with an appropriately protected amino compound to form a compound of formula (1) where R$_4$ is a protected amine, followed by removal of the protecting group by standard methods. Appropriate protecting groups may include, for example, benzyl, dimethoxybenzyl, trialkylsilyl or trifluoroacetyl groups.

Compounds of formula (1) where R$_4$ is an acyloxy, carbamate, acylamino, semicarbazide, thiosemicarbazide, sulphonamide, urea, thiourea, sulphamide, acylhydrazine or sulphonylhydrazine group may be prepared by derivatisation of the corresponding compound of formula (1) where R$_4$ is a hydroxy, mercapto, amino, monoalkylamino or hydrazino group using standard literature methods.

Compounds of formula (1) where R$_4$ is a sulphonyl or sulphinyl group may be prepared from compounds of formula (1) where R$_4$ is an alkylthio or arylthio group by standard methods such as oxidation with an appropriate reagent.

Compounds of formula (1) where R$_4$ is a group containing an amino substituent, for example an aminoalkyl group or an aminoalkylamino group such as an ethylenediamine group, may be further derivatised using standard methods as described above. For example the amino group may be converted into an alkylamine, amide, carbamate, urea, thiourea, sulphonamide or sulphamide by using standard literature methods such as alkylation, reductive alkylation, acylation, sulphonylation or reaction with an appropriate isocyanate.

Compounds of formula (1) where R$_4$ is an ester, amide or hydrazide may be prepared from compounds of formula (1) where R$_4$ is a halogen by standard methods such as carbonylation reactions. Alternatively compounds of formula (I) where R$_4$ is an ester group may be prepared from compounds of formula (2) where R$_4$ is an ester group by the methods described above. Compounds of formula (2) where R$_4$ is an ester group are known in the literature. Further modification of a compound of formula (1) where $R_4$ is an ester or amide can lead, by using standard literature methods, to compounds of formula (1) where $R_4$ is for example an aldehyde, carboxylic acid, oxime, amidine, hydroxyalkyl, or aminoalkyl group. Further modification of a compound of formula (1) where $R_4$ is an ester, amide, hydrazide, amidine, aldehyde or carboxylic acid can lead, by the use of standard literature methods, to compounds of formula (1) where $R_4$ is, for example a 5- or 6-membered heterocyclic group such as oxadiazole, thiadiazole, thiazole, oxazole, isoxazole, pyrazole, triazole, imidazole or pyrimidine.

Compounds of formula (1) where $R_1$ is an alkoxy, acyloxy or carbamate group may be prepared from compounds of formula (1) where $R_1$ is a hydroxy group by standard methods such as alkylation, acylation or by reaction with an appropriate isocyanate.

Compounds of formula (1) where $R_1$ is an amino, alkylamino, acylamino, sulphonylamino, urea or sulphamide may be prepared from compounds of formula (1) where $R_1$ is an amino group by standard methods such as alkylation, acylation, sulphonylation or by reaction with an appropriate isocyanate.

Compounds of formula (1) where $R_1$ is an amino group may be prepared from a compound of formula (1) where $R_1$ is a nitro group by standard methods such as reduction. Alternatively compounds of formula (1) where $R_1$ is an amino group may be prepared from a compound of formula (1) where $R_1$ and $R_2$ together form a carbonyl group by standard methods such a reductive amination.

Compounds of formula (1) where $R_1$ is a hydrazino group may be prepared from compounds of formula (1) where $R_1$ is a hydroxy group by standard methods such as conversion of the hydroxy group into a suitable leaving group, for example a mesylate or tosylate group, followed by displacement with hydrazine or an appropriately substituted hydrazine. Further derivatisation of the hydrazine group, if required, may be achieved by standard methods such as for example acylation or sulphonylation.

Compounds of formula (1) where $R_1$ and $R_2$ together form an imine group (C=N—$R_{11}$) or a hydrazone group (C=NN$R_{11}R_{12}$) may be prepared from compounds of formula (4) by standard methods such as treatment with the appropriate amine or hydrazine.

Compounds of formula (1) where $R_5$ is an aryl (including heteroaryl) group may be prepared from compounds of formula (1) where $R_5$ is a halogen by standard methods such as a palladium catalysed aryl coupling reaction such as a Suzuki coupling or a Stille coupling reaction. Compounds of formula (1) where $R_5$ is a halogen are prepared from compounds of formula (3) where $R_5$ is a halogen according to Reaction Scheme 1. Compounds of formula (3) where $R_5$ is a halogen are known in the literature.

Compounds of formula (1) where $R_5$ is an amino group may be prepared from compounds of formula (1) where $R_5$ is a nitro group by standard methods such as reduction. Further modification of compounds of formula (1) where $R_5$ is an amino group can lead, by the use of standard methods, to compounds of formula (1) where $R_5$ is an alkylamino, acylamino, carbamate, urea, thiourea, sulphonamide or sulphamide group as described above. Compounds of formula (1) where $R_5$ is a nitro group may be prepared from compounds of formula (3) where $R_5$ is a nitro group according to Reaction Scheme 1. Compounds of formula (3) where $R_5$ is a nitro group are known in the literature.

According to a further aspect of the invention, there is provided a pharmaceutical composition comprising a compound of the present invention in combination with a pharmaceutically acceptable carrier or excipient and a method of making such a composition comprising combining a compound of the present invention with a pharmaceutically acceptable carrier or excipient.

The pharmaceutical compositions employed in the present invention comprise a compound of the present invention, or pharmaceutically acceptable salts or prodrugs thereof, and may also contain a pharmaceutically acceptable carrier and optionally other therapeutic ingredients known to those skilled in the art. The term, "pharmaceutically acceptable salts", refers to salts prepared from pharmaceutically acceptable non-toxic acids including inorganic acids and organic acids.

Where the compounds of the present invention are basic, salts may be prepared from pharmaceutically acceptable non-toxic acids including inorganic and organic acids. Such acids include acetic, benzenesulfonic, benzoic, camphorsulfonic, citric, ethenesulfonic, fumaric, gluconic, glutamic, hippuric, hydrobromic, hydrochloric, isethionic, lactic, maleic, malic, mandelic, methanesulfonic, mucic, nitric, pamoic, pantothenic, phosphoric, succinic, sulfuric, tartaric, oxalic, p-toluenesulfonic and the like. Particularly preferred are hydrochloric, hydrobromic, phosphoric, and sulfuric acids, and most particularly preferred is the hydrochloride salt.

Any suitable route of administration may be employed for providing the patient with an effective dosage of a compound of the present invention. For example, oral, rectal, parenteral (intravenous, intramuscular), transdermal, subcutaneous, and the like may be employed. Dosage forms include tablets, troches, dispersions, suspensions, solutions, capsules, patches, and the like. The most suitable route in any given case will depend on the severity of the condition being treated. The most preferred route of administration of the present invention is the oral route. The compositions may be conveniently presented in unit dosage form and prepared by any of the methods well known in the art of pharmacy.

In practical use, the compounds of the present invention can be combined as the active ingredient in intimate admixture with a pharmaceutical carrier according to conventional pharmaceutical compounding techniques. The carrier may take a wide variety of forms depending on the form of preparation desired for administration, e.g. oral or parenteral (e.g. intravenous). In preparing the compositions for oral dosage form, any of the usual pharmaceutical media may be employed as carriers, such as, for example, water, glycols, oils, alcohols, flavouring agents, preservatives, colouring agents, and the like in the case of oral liquid preparations (such as suspensions, solutions and elixirs) or aerosols; or carriers such as starches, sugars, micro-crystalline cellulose, diluents, granulating agents, lubricants, binders, disintegrating agents, and the like may be used in the case of oral solid preparations such as, for example, powders, capsules, and tablets, with the solid oral preparations being preferred over the liquid preparations. The most preferred solid oral preparation is tablets.

Because of their ease of administration, tablets and capsules represent the most advantageous oral dosage unit form in which case solid pharmaceutical carriers are employed. If desired, tablets may be coated by standard aqueous or non-aqueous techniques.

In addition to the common dosage forms set out above, the compounds of the present invention may also be administered by controlled release means and/or delivery devices such as those described in U.S. Pat. Nos.: 3,845,770; 3,916, 899; 3,536,809; 3,598,123; 3,630,200; 4,008,719; 4,687,660; and 4,769,027, the disclosures of which are hereby incorporated by reference.

Pharmaceutical compositions employed in the present invention suitable for oral administration may be presented as discrete units such as capsules, cachets, or tablets, or aerosol sprays each containing a predetermined amount of the active ingredient as a powder or granules, a solution or a suspension in an aqueous liquid, an oil-in-water emulsion, or a water-in-oil liquid emulsion. Such compositions may be prepared by any of the methods of pharmacy, but all methods include the step of bringing the active ingredient into association with the carrier which constitutes one or more necessary ingredients. In general, the compositions are prepared by uniformly and intimately admixing the active ingredient with liquid carriers or finely divided solid carriers or both, and then, if necessary, shaping the product into the desired presentation.

For example, a tablet may be prepared by compression or moulding, optionally with one or more accessory ingredients. Compressed tablets may be prepared by compressing in a suitable machine the active ingredient in a free-flowing form such as powder or granules, optionally mixed with a binder, a lubricant, an inert diluent, and/or a surface active or dispersing agent. Moulded tablets may be made by moulding in a suitable machine a mixture of the powdered compound moistened with an inert liquid diluent.

The invention is further defined by reference to the following examples. It will be apparent to those skilled in the art that many modifications, both to materials and methods, may be practised without departing from the purpose and interest of this invention.

EXAMPLES

Synthetic Examples

The invention is illustrated with reference to Examples 1 to 170, as set out in Table 1. The syntheses of Examples 1 to 170 is described in Table 2 with reference to the general Synthetic Methods set out hereinafter. The analytical data for Examples 1 to 170 is given in Table 2.

TABLE 1

| Example | Structure | Compound Name |
| --- | --- | --- |
| 1 | 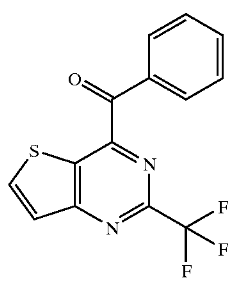 | Phenyl 2-trifluoromethylthieno[3,2-d]pyrimidin-4-ylmethanone |
| 2 | 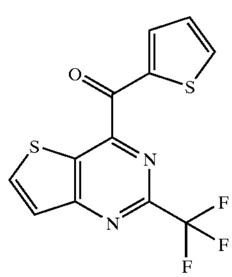 | 2-Thienyl 2-trifluoromethylthieno[3,2-d]pyrimidin-4-ylmethanone |
| 3 | 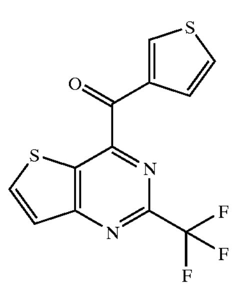 | 3-Thienyl 2-trifluoromethylthieno[3,2-d]pyrimidin-4-ylmethanone |

TABLE 1-continued
| Example | Structure | Compound Name |
| --- | --- | --- |
| 4 | 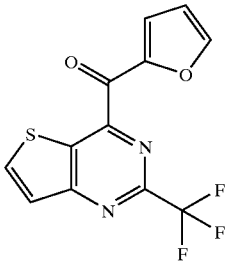 | 2-Furyl 2-trifluoromethylthieno[3,2-d]pyrimidin-4-ylmethanone |
| 5 | 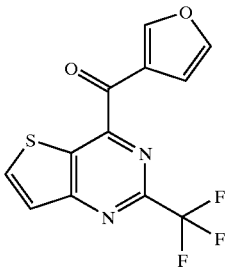 | 3-Furyl 2-trifluoromethylthieno[3,2-d]pyrimidin-4-ylmethanone |
| 6 | 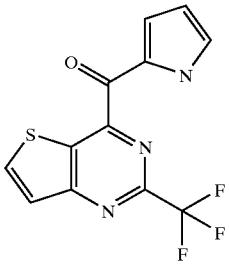 | 2-Pyrrolyl 2-trifluoromethylthieno[3,2-d]pyrimidin-4-ylmethanone |
| 7 | 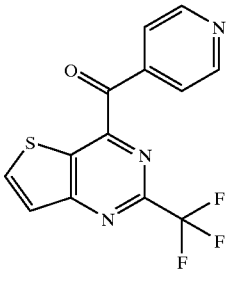 | 4-Pyridyl 2-trifluoromethylthieno[3,2-d]pyrimidin-4-ylmethanone |
| 8 | 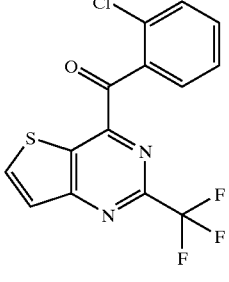 | 2-Chlorophenyl 2-trifluoromethylthieno[3,2-d]pyrimidin-4-ylmethanone |

TABLE 1-continued

| Example | Structure | Compound Name |
| --- | --- | --- |
| 9 | 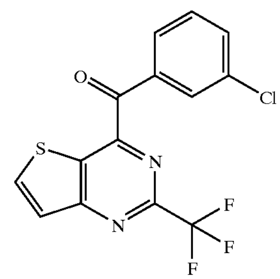 | 3-Chlorophenyl 2-trifluoromethylthieno[3,2-d]pyrimidin-4-ylmethanone |
| 10 | 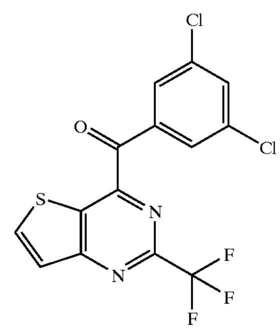 | 3,5-Dichlorophenyl 2-trifluoromethylthieno[3,2-d]pyrimidin-4-ylmethanone |
| 11 | 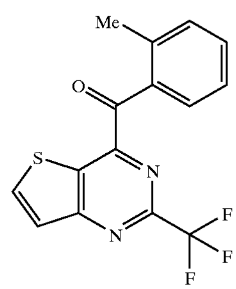 | 2-Methylphenyl 2-trifluoromethylthieno[3,2-d]pyrimidin-4-ylmethanone |
| 12 | 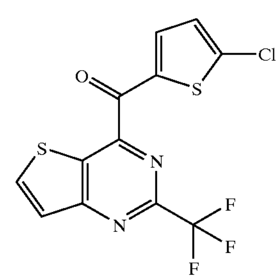 | 5-Chloro-2-thienyl 2-trifluoromethylthieno[3,2-d]pyrimidin-4-ylmethanone |
| 13 | 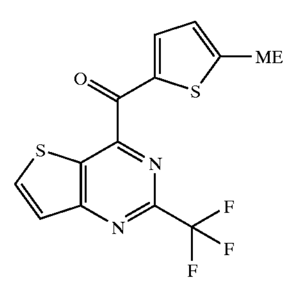 | 5-Methyl-2-thienyl 2-trifluoromethylthieno[3,2-d]pyrimidin-4-ylmethanone |

TABLE 1-continued

| Example | Structure | Compound Name |
| --- | --- | --- |
| 14 | 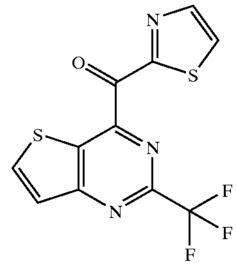 | 2-Thiazolyl 2-trifluoromethylthieno[3,2-d]pyrimidin-4-ylmethanone |
| 15 | 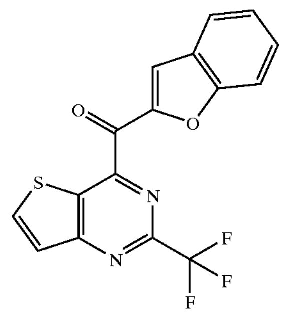 | 2-Benzofuranyl 2-trifluoromethylthieno[3,2-d]pyrimidin-4-ylmethanone |
| 16 | 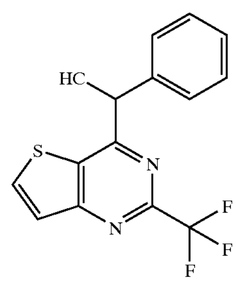 | α-Phenyl-2-trifluoromethylthieno[3,2-d]pyrimidine-4-acetonitrile |
| 17 | 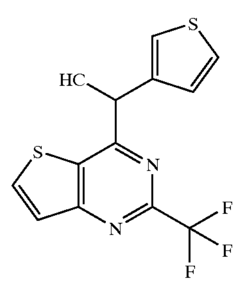 | α-(3-Thienyl-2-trifluoromethylthieno[3,2-d]pyrimidine-4-acetonitrile |
| 18 | 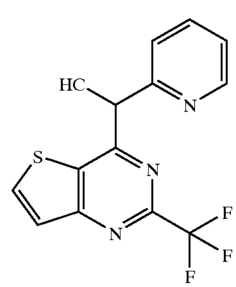 | α-(2-Pyridyl-2-trifluoromethylthieno[3,2-d]pyrimidine-4-acetonitrile |

TABLE 1-continued

| Example | Structure | Compound Name |
|---|---|---|
| 19 | 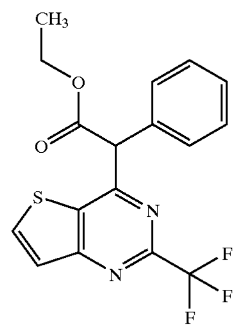 | Ethyl α-phenyl-2-trifluoromethylthieno[3,2-d]pyrimidine-4-acetate |
| 20 | 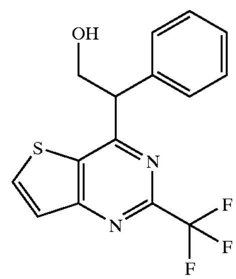 | β-Phenyl-2-trifluoromethylthieno[3,2-d]pyrimidine-4-ethanol |
| 21 | 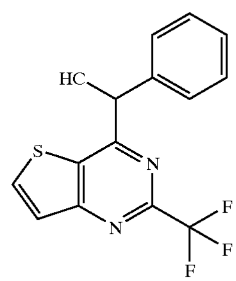 | α-Phenyl-2-trifluoromethylthieno[3,2-d]pyrimidine-4-methanol |
| 22 | 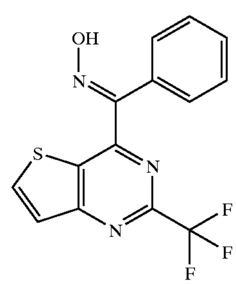 | Phenyl 2-trifluoromethylthieno[3,2-d]pyrimidin-4-ylmethanone oxime |
| 23 | 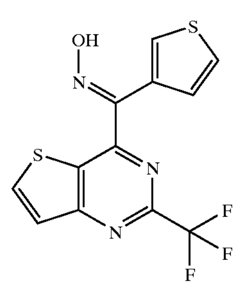 | 3-Thienyl 2-trifluoromethylthieno[3,2-d]pyrimidin-4-ylmethanone oxime |

TABLE 1-continued

| Example | Structure | Compound Name |
|---|---|---|
| 24 | 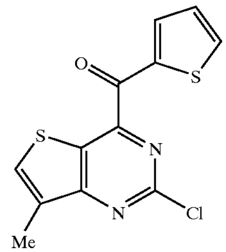 | 2-Chloro-7-methylthieno[3,2-d]pyrimidin-4-yl 2-thienylmethanone |
| 25 | 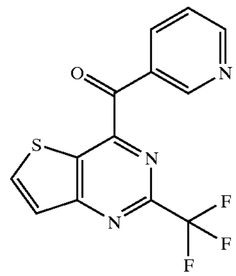 | 3-Pyridyl 2-trifluoromethylthieno[3,2-d]pyrimidin-4-ylmethanone |
| 26 | 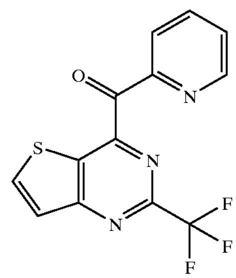 | 2-Pyridyl 2-trifluoromethylthieno[3,2-d]pyrimidin-4-ylmethanone |
| 27 | 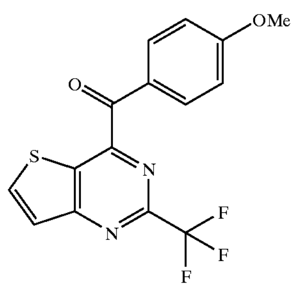 | 4-Methoxyphenyl 2-trifluoromethylthieno[3,2-d]pyrimidin-4-ylmethanone |
| 28 | 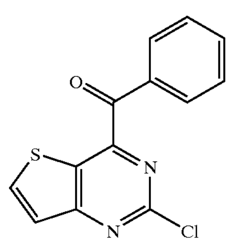 | 2-Chlorothieno[3,2-d]pyrimidin-4-yl phenylmethanone |

TABLE 1-continued

| Example | Structure | Compound Name |
| --- | --- | --- |
| 29 | 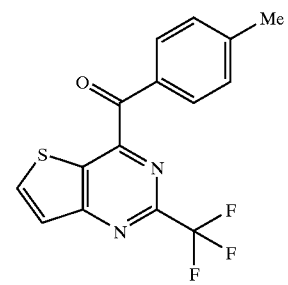 | 4-Methylphenyl 2-trifluoromethylthieno[3,2-d]pyrimidin-4-ylmethanone |
| 30 | 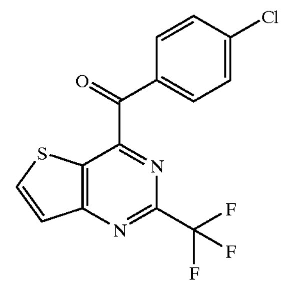 | 4-Chlorophenyl 2-trifluoromethylthieno[3,2-d]pyrimidin-4-ylmethanone |
| 31 | 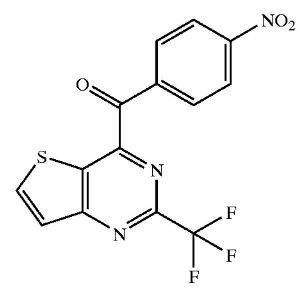 | 4-Nitrophenyl 2-trifluoromethylthieno[3,2-d]pyrimidin-4-ylmethanone |
| 32 | 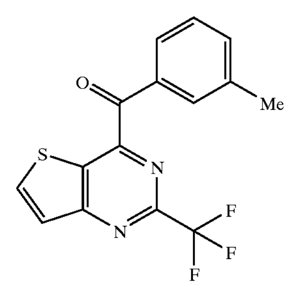 | 3-Methylphenyl 2-trifluoromethylthieno[3,2-d]pyrimidin-4-ylmethanone |
| 33 | 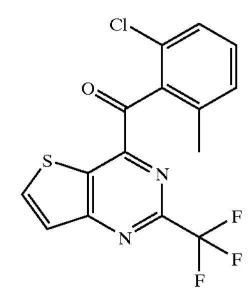 | 2-Chloro-6-fluorophenyl 2-trifluoromethylthieno[3,2-d]pyrimidin-4-ylmethanone |

TABLE 1-continued

| Example | Structure | Compound Name |
|---|---|---|
| 34 | 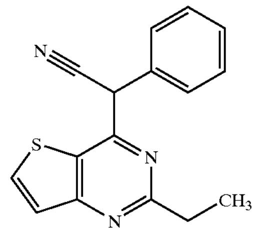 | 2-Ethyl-α-(2-pyridyl)thieno[3,2-d]pyrimidine-4-acetonitrile |
| 35 | 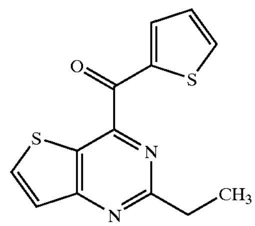 | 2-Ethylthieno[3,2-d]pyrimidin-4-yl 2-thienylmethanone |
| 36 | 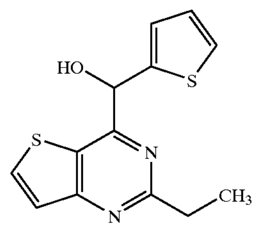 | 2-Ethyl-α-(2-thienyl)thieno[3,2-d]pyrimidine-4-methanol |
| 37 | 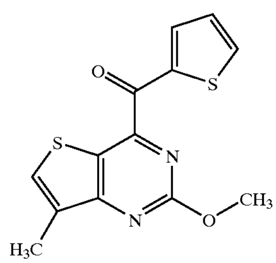 | 2-Methoxy-7-methylthieno[3,2-d]pyrimidin-4-yl 2-thienylmethanone |
| 38 | 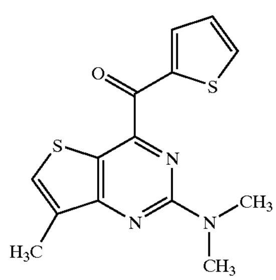 | 2-Dimethylamino-7-methylthieno[3,2-d]pyrimidin-4-yl 2-thienylmethanone |
| 39 | 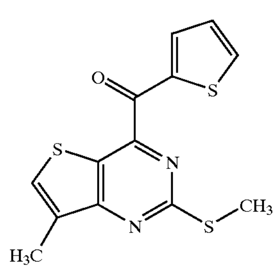 | 7-Methyl-2-methylthiothieno[3,2-d]pyrimidin-4-yl 2-thienylmethanone |

TABLE 1-continued

| Example | Structure | Compound Name |
| --- | --- | --- |
| 40 | 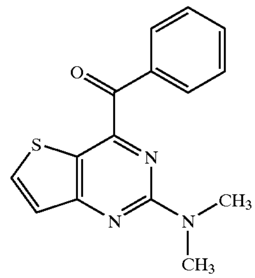 | 2-Dimethylaminothieno[3,2-d]pyrimidin-4-yl phenylmethanone |
| 41 | 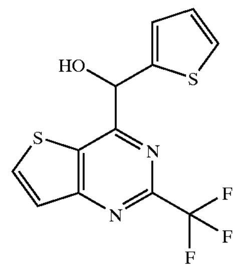 | α-(2-Thienyl)-2-trifluoromethylthieno[3,2-d]pyrimidine-4-methanol |
| 42 | 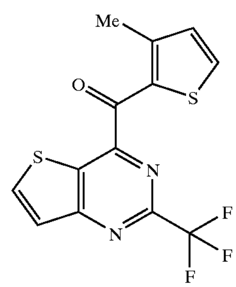 | 3-Methyl-2-thienyl 2-trifluoromethylthieno[3,2-d]pyrimidin-4-ylmethanone |
| 43 | 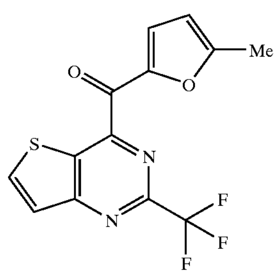 | 5-Methyl-2-furyl 2-trifluoromethylthieno[3,2-d]pyrimidin-4-ylmethanone |
| 44 | 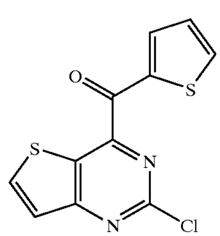 | 2-Chlorothieno[3,2-d]pyrimidin-4-yl 2-thienylmethanone |

TABLE 1-continued

| Example | Structure | Compound Name |
| --- | --- | --- |
| 45 | 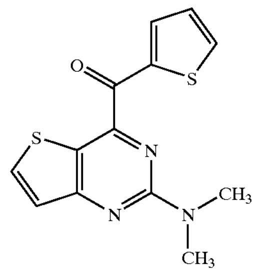 | 2-Dimethylaminothieno[3,2-d]pyrimidin-4-yl 2-thienylmethanone |
| 46 | 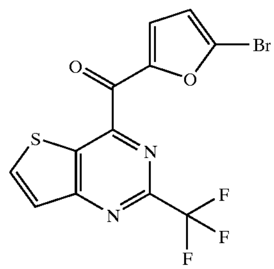 | 5-Bromo-2-thienyl 2-trifluoromethylthieno[3,2-d]pyrimidin-4-ylmethanone |
| 47 | 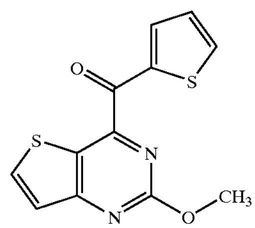 | 2-Methoxythieno[3,2-d]pyrimidin-4-yl 2-thienylmethanone |
| 48 | 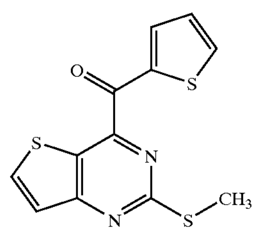 | 2-Methylthiothieno[3,2-d]pyrimidin-4-yl 2-thienylmethanone |
| 49 | 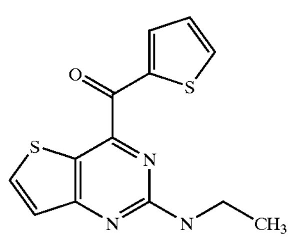 | 2-Ethylaminothieno[3,2-d]pyrimidin-4-yl 2-thienylmethanone |
| 50 | 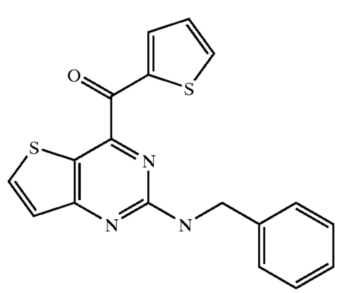 | 2-Benzylaminothieno[3,2-d]pyrimidin-4-yl 2-thienylmethanone |

TABLE 1-continued

| Example | Structure | Compound Name |
|---|---|---|
| 51 | 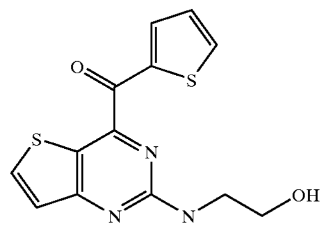 | 2-(2-Hydroxyethylamino)thieno[3,2-d]pyrimidin-4-yl 2-thienylmethanone |
| 52 | 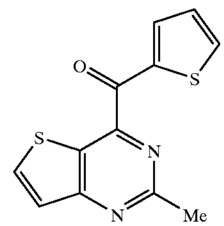 | 2-Methylthieno[3,2-d]pyrimidin-4-yl 2-thienylmethanone |
| 53 | 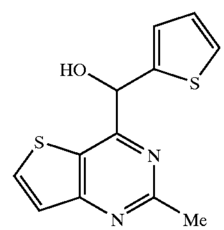 | 2-Methyl-α-(2-thienyl)thieno[3,2-d]pyrimidine-4-methanol |
| 54 | 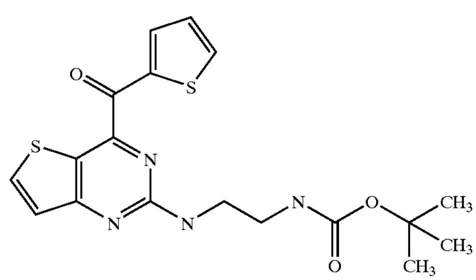 | Tert-butyl (2-(4-(2-thienylcarbonyl)thieno[3,2-d]pyrimidin-2-yl)aminoethyl)carbamate |
| 55 | 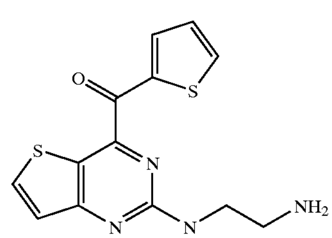 | 2-(2-Aminoethylamino)thieno[3,2-d]pyrimidin-4-yl 2-thienylmethanone dihydrochloride |
| 56 | 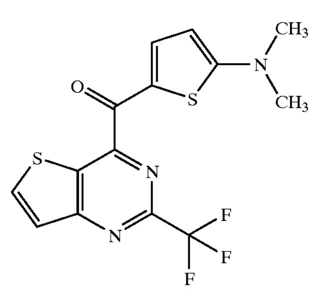 | 5-Dimethylamino-2-thienyl 2-trifluoromethylthieno[3,2-d]pyrimidin-4-ylmethanone |

TABLE 1-continued

| Example | Structure | Compound Name |
|---|---|---|
| 57 | 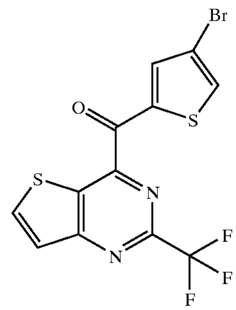 | 4-Bromo-2-thienyl 2-trifluoromethylthieno[3,2-d]pyrimidin-4-ylmethanone |
| 58 | 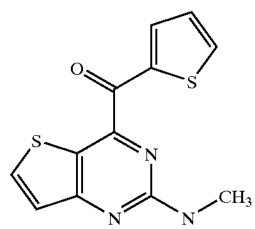 | 2-Methylaminothieno[3,2-d]pyrimidin-4-yl thienylmethanone |
| 59 | 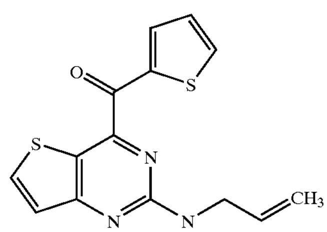 | 2-Allylaminothieno[3,2-d]pyrimidin-4-yl 2-thienylmethanone |
| 60 | 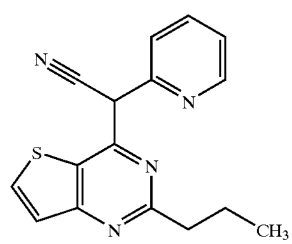 | 2-n-Propyl-α-(2-pyridyl)thieno[3,2-d]pyrmidine-4-acetonitrile |
| 61 | 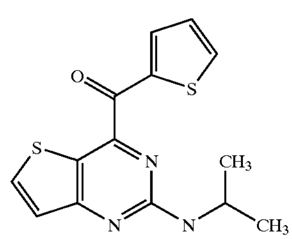 | 2-Isopropylaminothieno[3,2-d]pyrimidin-4-yl 2-thienylmethanone |
| 62 | 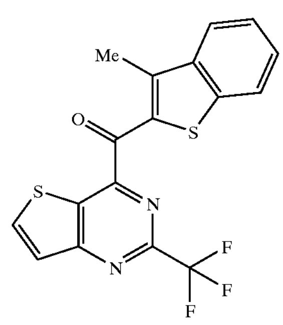 | 3-Methylbenzothiophene-2-yl 2-trifluoromethylthieno[3,2-d]pyrimidin-4-ylmethanone |

TABLE 1-continued

| Example | Structure | Compound Name |
| --- | --- | --- |
| 63 | 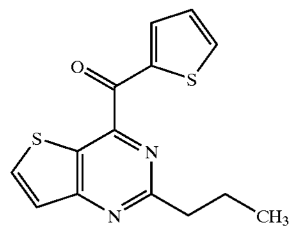 | 2-n-Propylthieno[3,2-d]pyrimidin-4-yl 2-thienylmethanone |
| 64 | 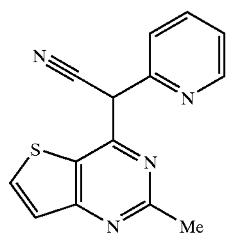 | 2-Methyl-α-(2-pyridyl)thieno[3,2-d]pyrimidine-4-acetonitrile |
| 65 | 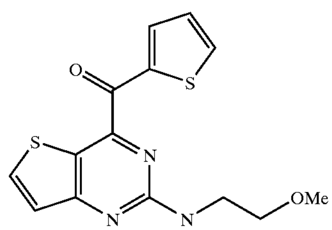 | 2-(2-Methoxyethylamino)thieno[3,2-d]pyrimidin-4-yl 2-thienylmethanone |
| 66 | 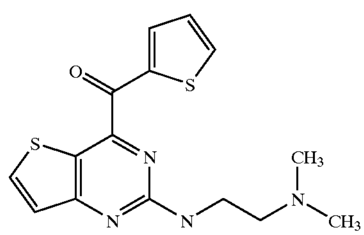 | 2-(2-Dimethylaminoethylamino)thieno[3,2-d]pyrimidin-4-yl 2-thienylmethanone dihydrochloride |
| 67 | 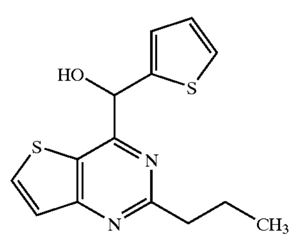 | 2-n-Propyl-α-(2-thienyl)thieno[3,2-d]pyrimidine-4-methanol |
| 68 | 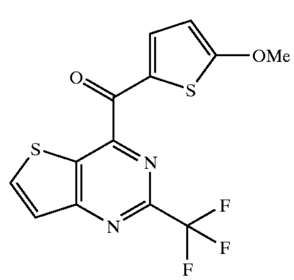 | 5-Methoxy-2-thienyl 2-trifluoromethylthieno[3,2-d]pyrimidin-4-ylmethanone |

TABLE 1-continued
| Example | Structure | Compound Name |
| --- | --- | --- |
| 69 | 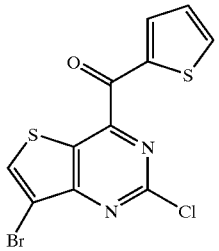 | 7-Bromo-2-chlorothieno[3,2-d]pyrimidin-4-yl 2-thienylmethanone |
| 70 | 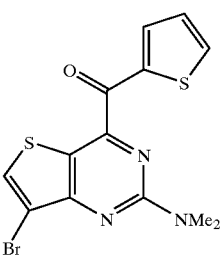 | 7-Bromo-2-dimethylaminothieno[3,2-d]pyrimidin-4-yl 2-thienylmethanone |
| 71 | 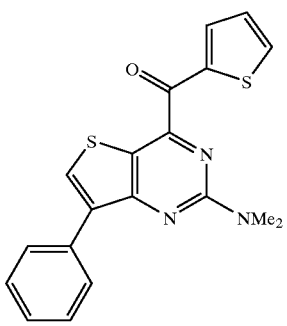 | 2-Dimethylamino-7-phenylthieno[3,2-d]pyrimidin-4-yl 2-thienylmethanone |
| 72 | 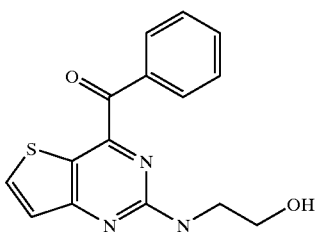 | 2-(2-Hydroxyethylamino)thieno[3,2-d]pyrimidin-4-yl phenylmethanone |
| 73 | 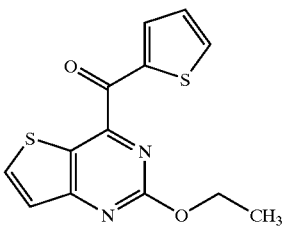 | 2-Ethoxythieno[3,2-d]pyrimidin-4-yl 2-thienylmethanone |

TABLE 1-continued

| Example | Structure | Compound Name |
| --- | --- | --- |
| 74 | 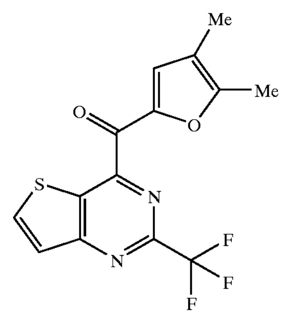 | 4,5-Dimethyl-2-furyl 2-trifluoromethylthieno[3,2-d]pyrimidin-4-ylmethanone |
| 75 | 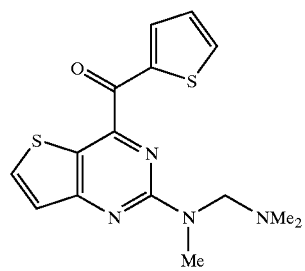 | 2-(N-(2-Dimethylaminoethyl)-N-methylamino)thieno[3,2-d]pyrimidin-4-yl thienylmethanone dihydrochloride |
| 76 | 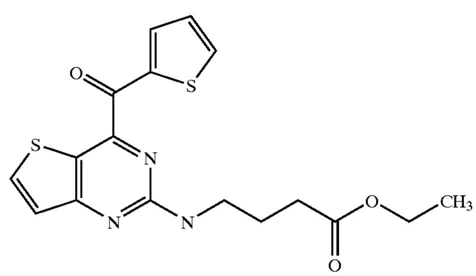 | Ethyl 4-(4-(2-thienylcarbonyl)thieno[3,2-d]pyrimidin-2-ylamino)butanoate |
| 77 | 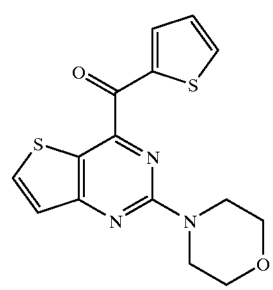 | 2-(4-Morpholinyl)thieno[3,2-d]pyrimidin-4-yl 2-thienylmethanone |
| 78 | 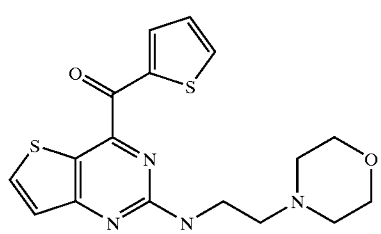 | 2-(2-(4-Morpholinyl)ethylamino)thieno[3,2-d]pyrimidin-4-yl 2-thienylmethanone |

TABLE 1-continued

| Example | Structure | Compound Name |
|---|---|---|
| 79 | 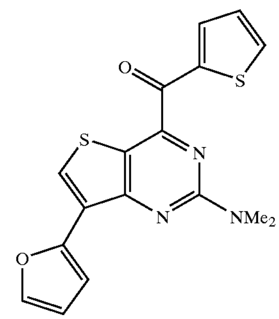 | 2-Dimethylamino-7-(2-furyl)thieno[3,2-d]pyrimidin-4-yl 2-thienylmethanone |
| 80 | 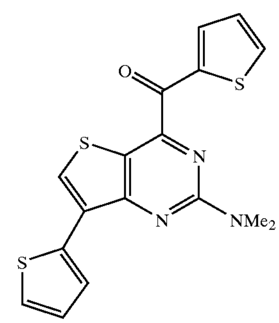 | 2-Dimethylamino-7-(2-thienyl)thieno[3,2-d]pyrimidin-4-yl 2-thienylmethanone |
| 81 | 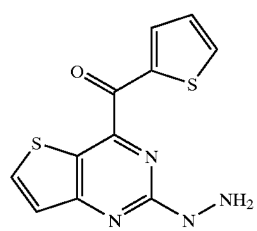 | 2-Hydrazinothieno[3,2-d]pyrimidin-4-yl 2-thienylmethanone |
| 82 | 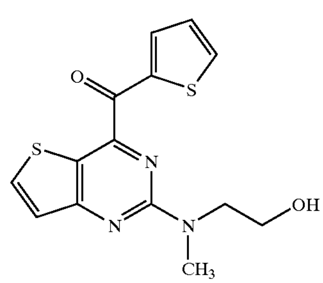 | 2-(N-(2-Hydroxyethyl)-N-methylamino)thieno[3,2-d]pyrimidin-4-yl 2-thienylmethanone |
| 83 | 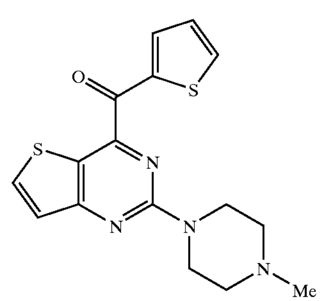 | 2-(4-Methylpiperazinyl)thieno[3,2-d]pyrimidin-4-yl 2-thienylmethanone |

TABLE 1-continued

| Example | Structure | Compound Name |
|---|---|---|
| 84 | 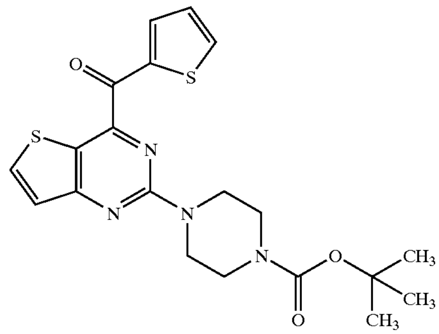 | Tert-butyl 4-(4-(2-thienylcarbonyl)thieno[3,2-d]pyrimidin-2-yl)piperazinecarboxylate |
| 85 | 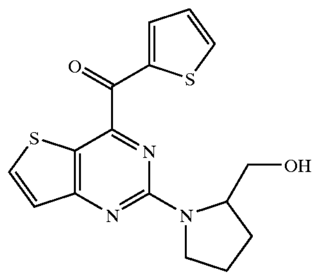 | (2R)-2-(2-Hydroxymethylpyrrolidin-1-yl)thieno[3,2-d]pyrimidin-4-yl 2-thienylmethanone |
| 86 | 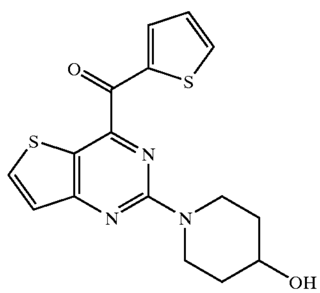 | 2-(4-Hydroxypiperidin-1-yl)thieno[3,2-d]pyrimidin-4-yl 2-thienylmethanone |
| 87 | 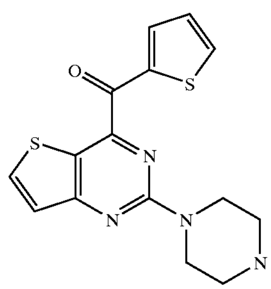 | 2-(1-Piperazinyl)thieno[3,2-d]pyrimidin-4-yl 2-thienylmethanone |
| 88 | 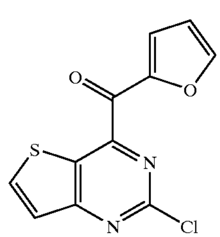 | 2-Chlorothieno[3,2-d]pyrimidin-4-yl 2-furylmethanone |

TABLE 1-continued

| Example | Structure | Compound Name |
| --- | --- | --- |
| 89 | 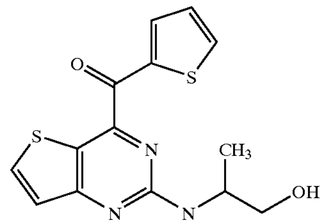 | (2RS)-2-(1-Hydroxy-2-propylamino)thieno[3,2-d]pyrimidin-4-yl 2-thienylmethanone |
| 90 | 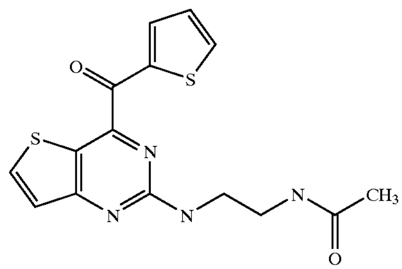 | N-(2-(4-(2-Thienylcarbonyl)thieno[3,2-d]pyrimidin-2-yl)aminoethyl)acetamide |
| 91 | 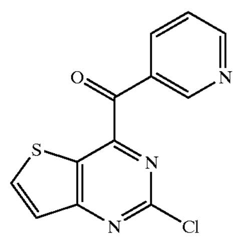 | 2-Chlorothieno[3,2-d]pyrimidin-4-yl 3-pyridylmethanone |
| 92 | 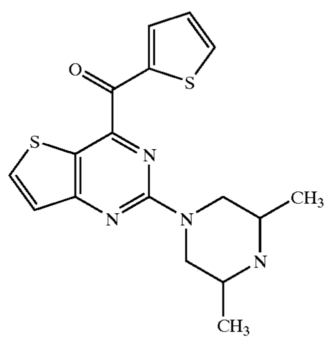 | Cis-2-(3,5-dimethyl-1-piperazinyl)thieno[3,2-d]pyrimidin-4-yl 2-thienylmethanone |
| 93 | 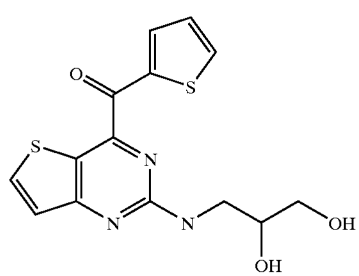 | (2RS)-2-(2,3-Dihydroxypropylamino)thieno[3,2-d]pyrimidin-4-yl 2-thienylmethanone |

TABLE 1-continued

| Example | Structure | Compound Name |
|---------|-----------|---------------|
| 94 | 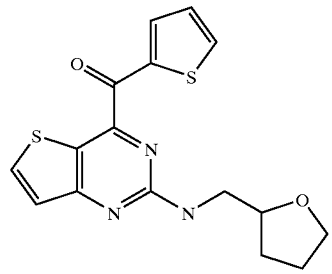 | 2-(Tetrahydrofuran-2-ylmethylamino)thieno[3,2-d]pyrimidin-4-yl 2-thienylmethanone |
| 95 | 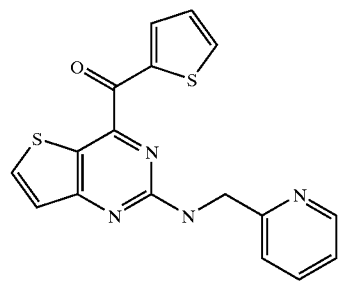 | 2-(2-Pyridylmethylamino)thieno[3,2-d]pyrimidin-4-yl 2-thienylmethanone |
| 96 | 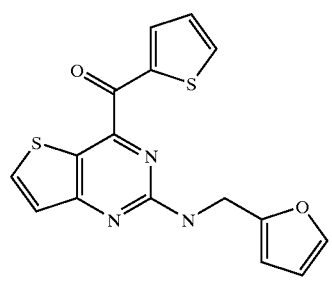 | 2-(2-Furylmethylamino)thieno[3,2-d]primidin-4-yl 2-thienylmethanone |
| 97 | 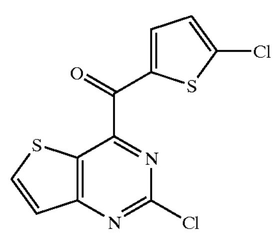 | 2-Chlorothieno[3,2-d]primidin-4-yl 5-chloro-2-thienylmethanone |
| 98 | 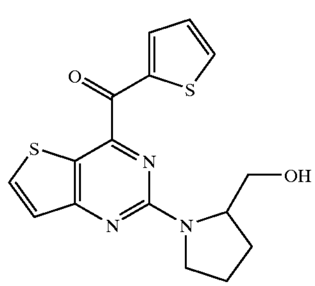 | (2S)-2-(2-Hydroxymethylpyrrolidin-1-yl)thieno[3,2-d]pyrimidin-4-yl 2-thienylmethanone |

TABLE 1-continued

| Example | Structure | Compound Name |
| --- | --- | --- |
| 99 | 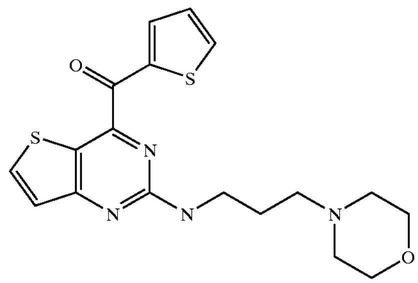 | 2-(3-(Morpholin-4-yl)propylamino)thieno[3,2-d]pyrimidin-4-yl 2-thienylmethanone |
| 100 | 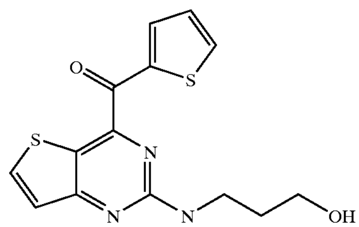 | 2-(3-Hydroxypropylamino)thieno[3,2-d]pyrimidin-4-yl 2-thienylmethanone |
| 101 | 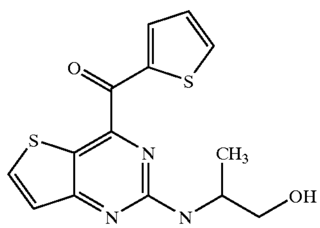 | (2S)-2-(1-Hydroxy-2-propylamino)thieno[3,2-d]pyrimidin-4-yl 2-thienylmethanone |
| 102 | 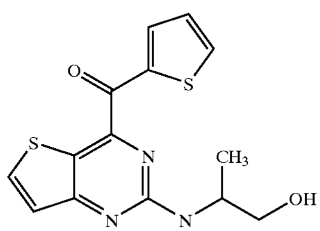 | (2R)-2-(1-Hydroxy-2-propylamino)thieno[3,2-d]pyrimidin-4-yl 2-thienylmethanone |
| 103 | 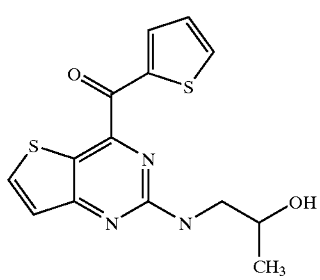 | (2R)-2-(2-Hydroxypropylamino)thieno[3,2-d]pyrimidin-4-yl 2-thienylmethanone |
| 104 | 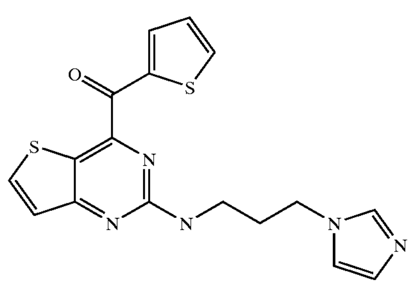 | 2-(3-(1H-Imidazol-1-yl)propylamino)thieno[3,2-d]pyrimidin-4-yl 2-thienylmethanone |

TABLE 1-continued

| Example | Structure | Compound Name |
| --- | --- | --- |
| 105 | 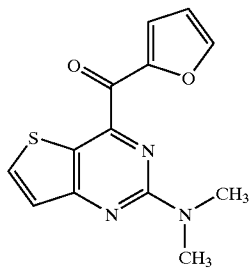 | 2-Dimethylaminothieno[3,2-d]pyrimidin-4-yl 2-furylmethanone |
| 106 | 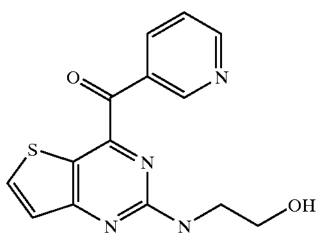 | 2-(2-Hydroxyethylamino)thieno[3,2-d]pyrimidin-4-yl 3-pyridylmethanone |
| 107 | 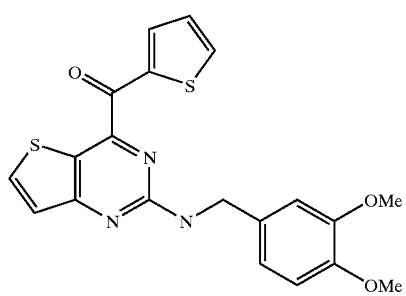 | 2-(3,4-Dimethoxybenzylamino)thieno[3,2-d]pyrimidin-4-yl 2-thienylmethanone |
| 108 | 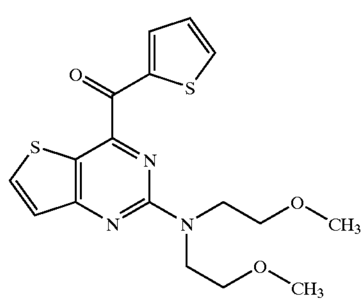 | 2-(N,N-Bis(2-methoxyethyl)amino)thieno[3,2-d]pyrimidin-4-yl 2-thienylmethanone |
| 109 | 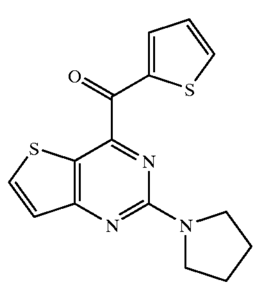 | 2-(Pyrrolidin-1-yl)thieno[3,2-d]pyrimidin-4-yl 2-thienylmethanone |

TABLE 1-continued

| Example | Structure | Compound Name |
| --- | --- | --- |
| 110 | 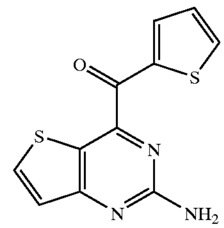 | 2-Aminothieno[3,2-d]pyrimidin-4-yl 2-thienylmethanone |
| 112 | 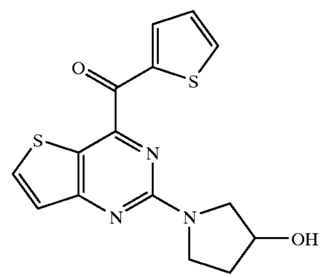 | (3RS)-2-(3-Hydroxypyrrolidin-1-yl)thieno[3,2-d]pyrimidin-4-yl 2-thienylmethanone |
| 113 | 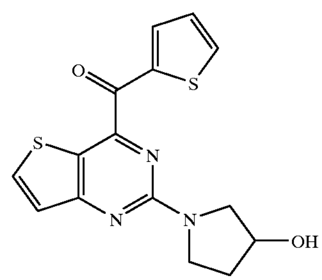 | (3R)-2-(3-Hydroxypyrrolidin-1-yl)thieno[3,2-d]pyrimidin-4-yl 2-thienylmethanone |
| 114 | 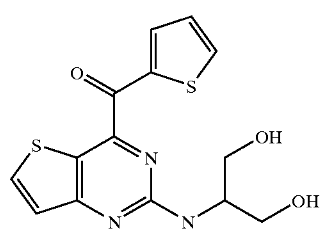 | 2-(1,3-Dihydroxy-2-propylamino)thieno[3,2-d]pyrimidin-4-yl 2-thienylmethanone |
| 115 | 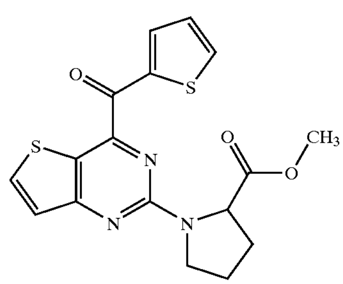 | (2S)-N-(4-(2-Thienylcarbonyl)thieno[3,2-d]pyrimidin-2-yl)proline methyl ester |
| 116 | 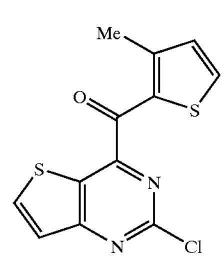 | 2-Chlorothieno[3,2-d]pyrimidin-4-yl 3-methyl-2-thienylmethanone |

TABLE 1-continued

| Example | Structure | Compound Name |
| --- | --- | --- |
| 117 | 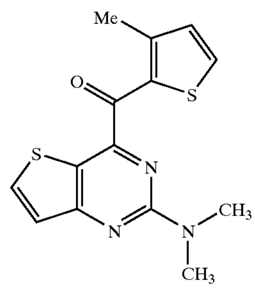 | 2-Dimethylaminothieno[3,2-d]pyrimidin-4-yl 3-methyl-2-thienylmethanone |
| 118 | 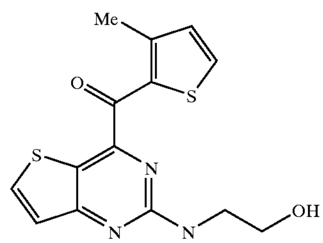 | 2-(2-Hydroxyethylamino)thieno[3,2-d]pyrimidin-4-yl 3-methyl-2-thienylmethanone |
| 119 | 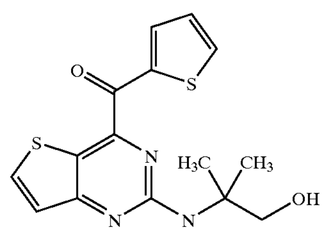 | 2-(1-Hydroxy-2-methyl-2-propylamino)thieno[3,2-d]pyrimidin-4-yl 2-thienylmethanone |
| 120 | 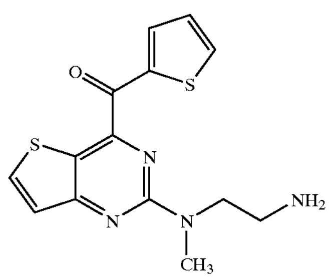 | 2-(N-(2-Aminoethyl)-N-methylamino)thieno[3,2-d]pyrimidin-4-yl 2-thienylmethanone |
| 121 | 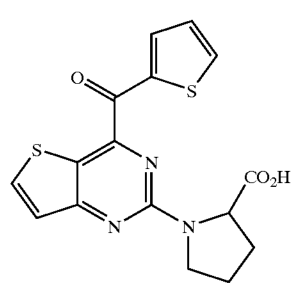 | (2R)-N-(4-(2-Thienylcarbonyl)thieno[3,2-d]pyrimidin-2-yl)proline |

TABLE 1-continued

| Example | Structure | Compound Name |
| --- | --- | --- |
| 122 | 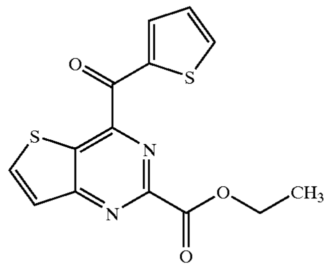 | Ethyl 4-(2-thienylcarbonyl)thieno[3,2-d]pyrimidin-2-carboxylate |
| 123 | 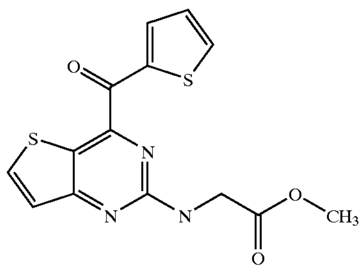 | Methyl (4-(2-thienylcarbonyl)thieno[3,2-d]pyrimidin-2-ylamino)acetate |
| 124 | 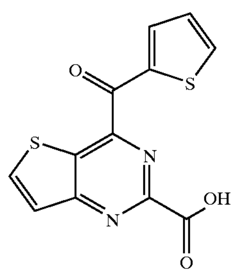 | 4-(2-Thienylcarbonyl)thieno[3,2-d]pyrimidin-2-carboxylic acid |
| 125 | 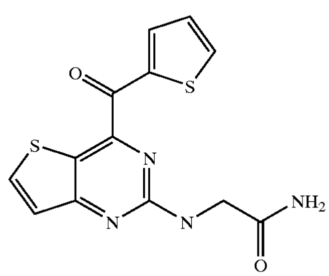 | (4-(2-Thienylcarbonyl)thieno[3,2-d]pyrimidin-2-ylamino)acetamide |
| 126 | 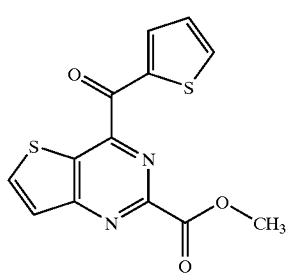 | Methyl 4-(2-thienylcarbonyl)thieno[3,2-d]pyrimidin-2-carboxylate |

TABLE 1-continued

| Example | Structure | Compound Name |
|---|---|---|
| 127 | 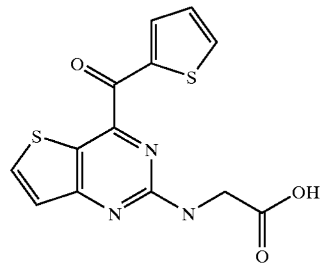 | (4-(2-Thienylcarbonyl)thieno[3,2-d]pyrimidin-2-ylamino)acetic acid |
| 128 | 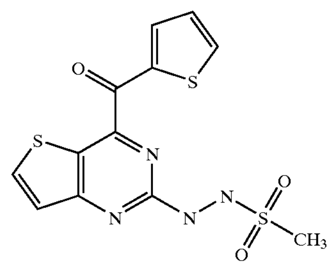 | Methanesulphonic acid 2-(4-(2-thienylcarbonyl)thieno[3,2-d]pyrimidin-2-yl)hydrazide |
| 129 | 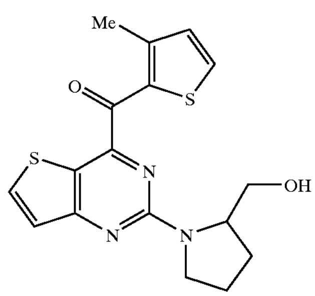 | (2R)-2-(2-Hydroxymethylpyrrolidin-1-yl)thieno[3,2-d]pyrimidin-4-yl 3-methyl-2-thienylmethanone |
| 130 | 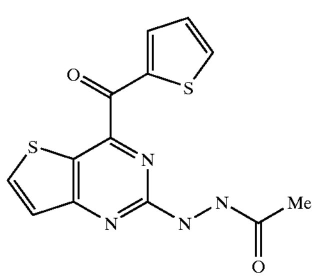 | Acetic acid 2-(4-(2-thienylcarbonyl)thieno[3,2-d]pyrimidin-2-yl)hydrazide |
| 131 | 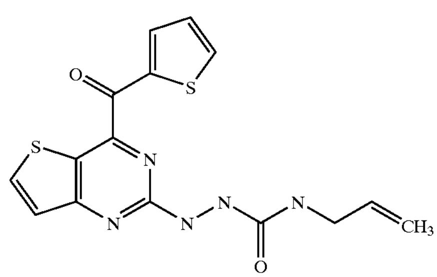 | N-Allyl-2-(4-(2-thienylcarbonyl)thieno[3,2-d]pyrimidin-2-yl)hydrazinecarboxamide |

TABLE 1-continued

| Example | Structure | Compound Name |
|---------|-----------|---------------|
| 132 | 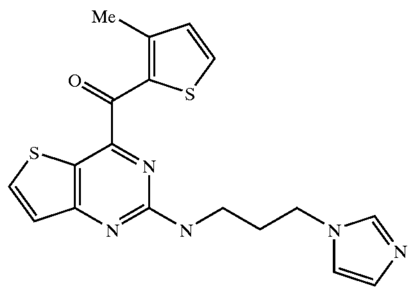 | 2-(3-(1H-imidazol-1-yl)propylamino)thieno[3,2-d]pyrimidin-4-yl 3-methyl-2-thienylmethanone |
| 133 | 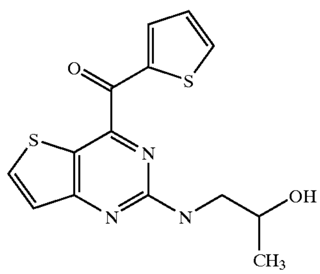 | (2S)-2-(2-Hydroxypropylamino)thieno[3,2-d]pyrimidin-4-yl 2-thienylmethanone |
| 134 | 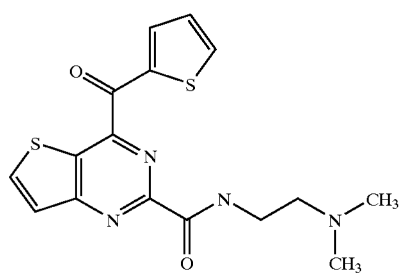 | N-(2-Dimethylaminoethyl)-4-(2-thienylcarbonyl)thieno[3,2-d]pyrimidin-2-carboxamide |
| 135 | 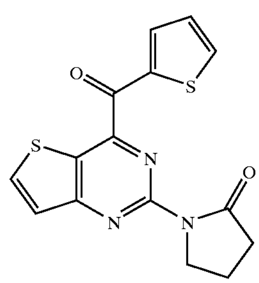 | 1-(4-(2-Thienylcarbonyl)thieno[3,2-d]pyrimidin-2-yl)-2-pyrrolidinone |
| 136 | 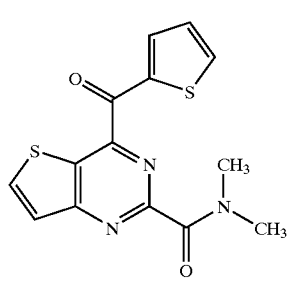 | N,N-Dimethyl-4-(2-thienylcarbonyl)thieno[3,2-d]pyrimidin-2-carboxamide |

TABLE 1-continued

| Example | Structure | Compound Name |
| --- | --- | --- |
| 137 | 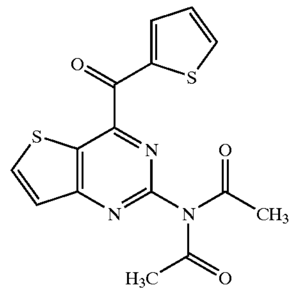 | N-Acetyl-N-(4-(2-thienylcarbonyl)thieno[3,2-d]pyrimidin-2-yl)acetamide |
| 138 | 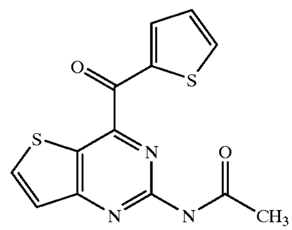 | N-(4-(2-Thienylcarbonyl)thieno[3,2-d]pyrimidin-2-yl)acetamide |
| 139 | 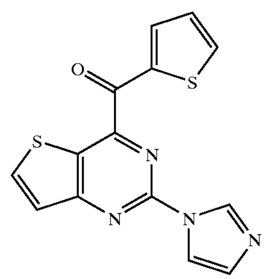 | 2-(1H-Imidazol-1-yl)thieno[3,2-d]pyrimidin-4-yl 2-thienylmethanone |
| 140 | 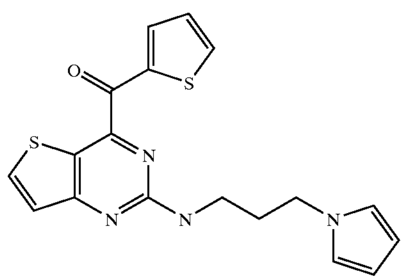 | 2-(3-(1H-Pyrrol-1-yl)propylamino)thieno[3,2-d]pyrimidin-4-yl 2-thienylmethanone |
| 141 | 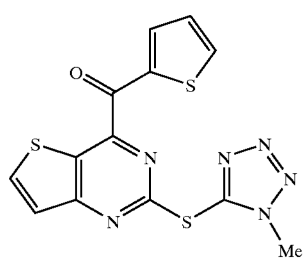 | 2-(1-Methyl-1H-tetrazol-5-ylthio)thieno[3,2-d]pyrimidin-4-yl 2-thienylmethanone |

TABLE 1-continued

| Example | Structure | Compound Name |
| --- | --- | --- |
| 142 | 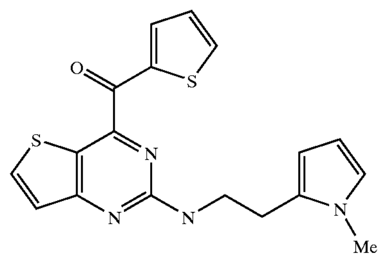 | 2-(2-(1-Methyl-1H-pyrrol-2-yl)ethylamino)thieno[3,2-d]pyrimidin-4-yl 2-thienylmethanone |
| 143 | 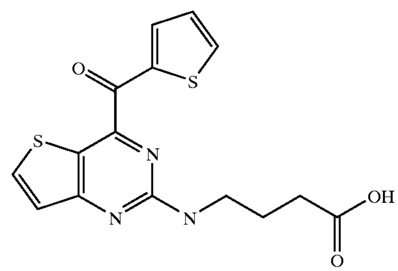 | 4-(4-(2-Thienylcarbonyl)thieno[3,2-d]pyrimidin-2-ylamino)butanoic acid |
| 144 | 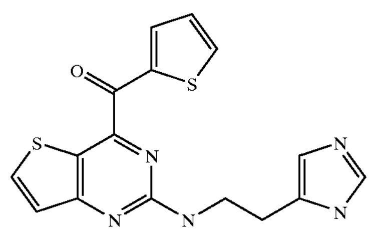 | 2-(2-(1H-Imidazol-4-yl)ethylamino)thieno[3,2-d]pyrimdin-4-yl 2-thienylmethanone |
| 145 | 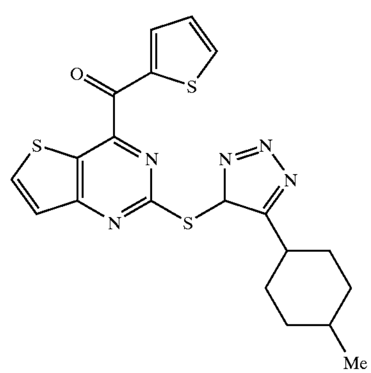 | 2-(1-(4-Hydroxyphenyl)-1H-tetrazol-5-ylthio)thieno[3,2-d]pyrimidin-4-yl 2-thienylmethanone |
| 146 | 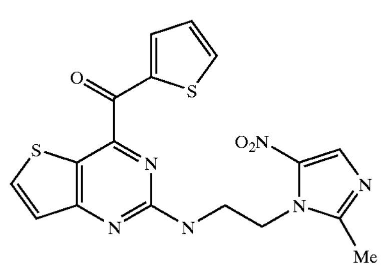 | 2-(2-(2-Methyl-5-nitro-1H-imidazol-1-yl)ethylamino)thieno[3,2-d]pyrimidin-4-yl 2-thienylmethanone |

TABLE 1-continued

| Example | Structure | Compound Name |
|---|---|---|
| 147 | 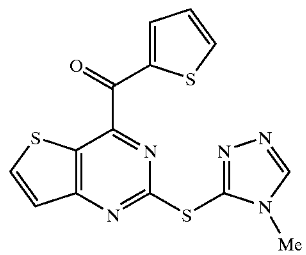 | 2-(4-Methyl-4H-[1,3,4]triazol-3-ylthio)thieno[3,2-d]pyrimidin-4-yl 2-thienylmethanone |
| 148 | 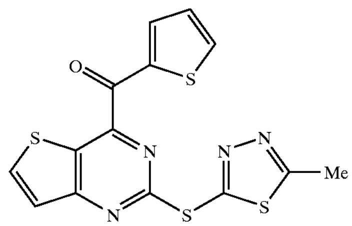 | 2-(5-Methyl-[1,3,4]-thiadiazol-2-ylthio)thieno[3,2-d]pyrimidin-4-yl 2-thienylmethanone |
| 149 | 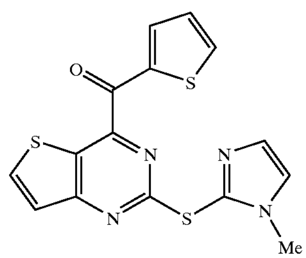 | 2-(1-Methyl-1H-imidazol-2-ylthio)thieno[3,2-d]pyrimidin-4-yl 2-thienylmethanone |
| 150 | 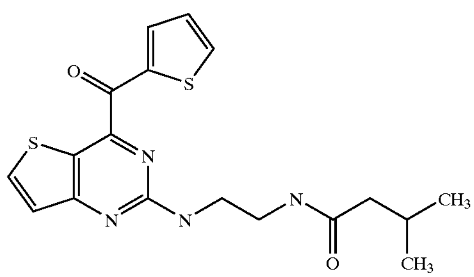 | 3-Methyl-N-(2-(4-(2-thienylcarbonyl)thieno[3,2-d]pyrimidin-2-yl)aminoethyl)butanamide |
| 151 | 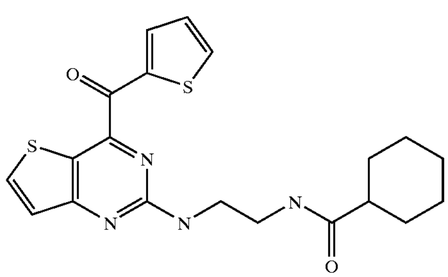 | N-(2-(4-(2-Thienylcarbonyl)thieno[3,2-d]pyrimidin-2-yl)aminoethyl)cyclohexylcarboxamide |
| 152 | 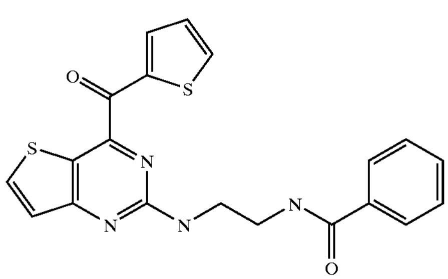 | N-(2-(4-(2-Thienylcarbonyl)thieno[3,2-d]pyrimidin-2-yl)aminoethyl)benzamide |

TABLE 1-continued

| Example | Structure | Compound Name |
|---|---|---|
| 153 | 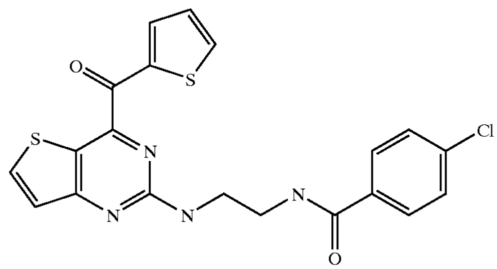 | 4-Chloro-N-(2-(4-(2-thienylcarbonyl)thieno[3,2-d]pyrimidin-2-yl)aminoethyl)benzamide |
| 154 | 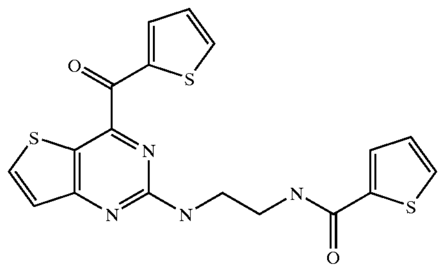 | N-(2-(4-(2-Thienylcarbonyl)thieno[3,2-d]pyrimidin-2-yl)aminoethyl)-2-thiophenecarboxamide |
| 155 | 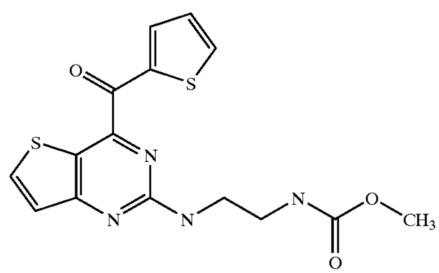 | Methyl (2-(4-(2-thienylcarbonyl)thieno[3,2-d]pyrimidin-2-yl)aminoethyl)carbamate |
| 156 | 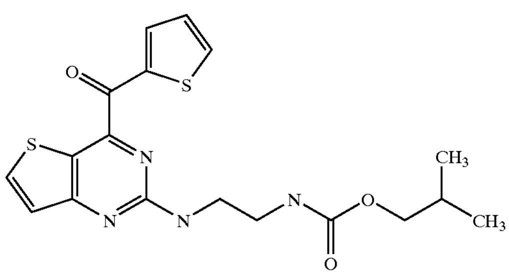 | 2-Methylpropyl (2-(4-(2-thienylcarbonyl)thieno[3,2-d]pyrimidin-2-yl)aminoethyl)carbamate |
| 157 | 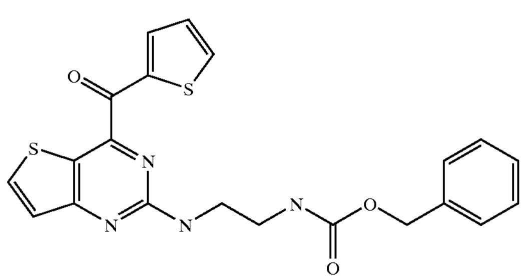 | Benzyl (2-(4-(2-thienylcarbonyl)thieno[3,2-d]pyrimidin-2-yl)aminoethyl)carbamate |

TABLE 1-continued

| Example | Structure | Compound Name |
| --- | --- | --- |
| 158 | 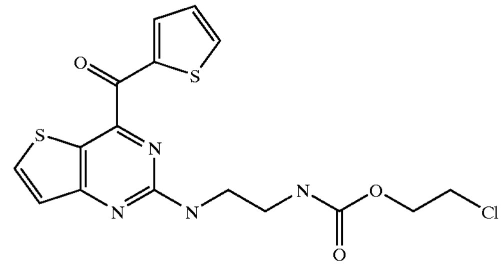 | 2-Chloroethyl (2-(4-(2-thienylcarbonyl)thieno[3,2-d]pyrimidin-2-yl)aminoethyl)carbamate |
| 159 | 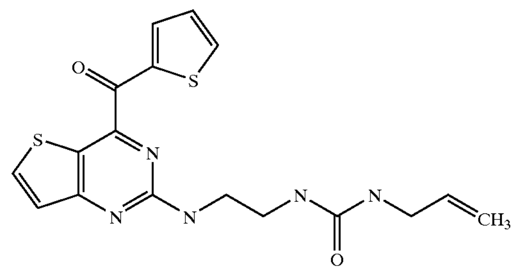 | N-Allyl-N'-(2-(4-(2-thienylcarbonyl)thieno[3,2-d]pyrimidin-2-yl)aminoethyl)urea |
| 160 | 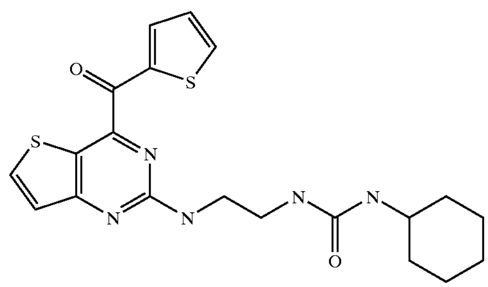 | N-Cyclohexyl-N'-(2-(4-(2-thienylcarbonyl)thieno[3,2-d]pyrimidin-2-yl)aminoethyl)urea |
| 161 | 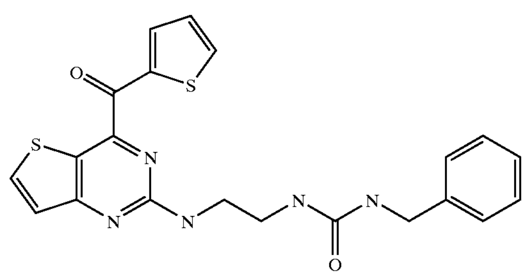 | N-Benzyl-N'-(2-(4-(2-thienylcarbonyl)thieno[3,2-d]pyrimidin-2-yl)aminoethyl)urea |
| 162 | 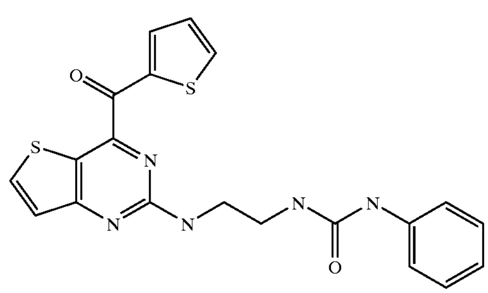 | N-Phenyl-N'-(2-(4-(2-thienylcarbonyl)thieno[3,2-d]pyrimidin-2-yl)aminoethyl)urea |

TABLE 1-continued

| Example | Structure | Compound Name |
|---|---|---|
| 163 | 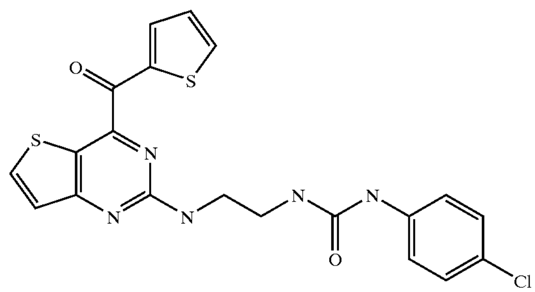 | N-(4-Chlorophenyl)-N'-(2-(4-(2-thienylcarbonyl)thieno[3,2-d]pyrimidin-2-yl)aminoethyl)urea |
| 164 | 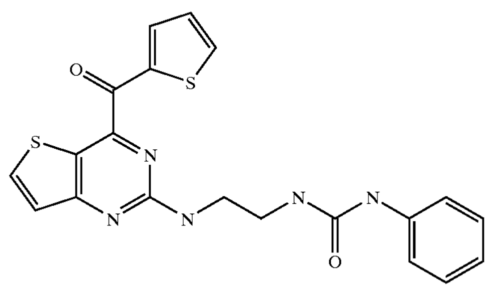 | N-Phenyl-N'-(2-(4-(2-thienylcarbonyl)thieno[3,2-d]pyrimidin-2-yl)aminoethyl)thiourea |
| 165 | 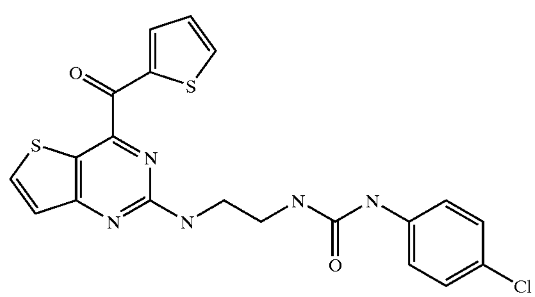 | N-(4-Chlorophenyl)-N'-(2-(4-(2-thienylcarbonyl)thieno[3,2-d]pyrimidin-2-yl)aminoethyl)thiourea |
| 166 | 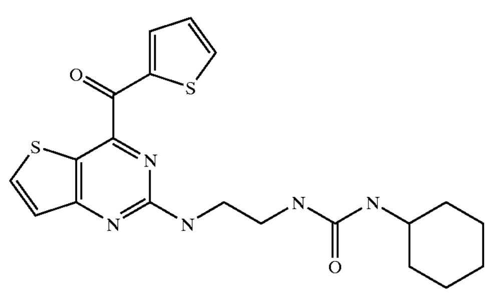 | N-Cyclohexyl-N'-(2-(4-(2-thienylcarbonyl)thieno[3,2-d]pyrimidin-2-yl)aminoethyl)thiourea |
| 167 | 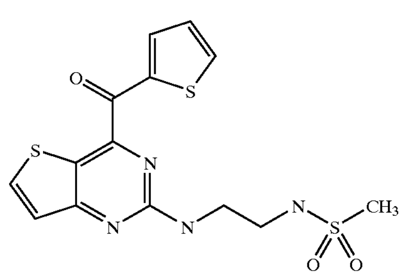 | N-(2-(4-(2-Thienylcarbonyl)thieno[3,2-d]pyrimidin-2-yl)aminoethyl)methanesulphonamide |

TABLE 1-continued

| Example | Structure | Compound Name |
|---|---|---|
| 168 | 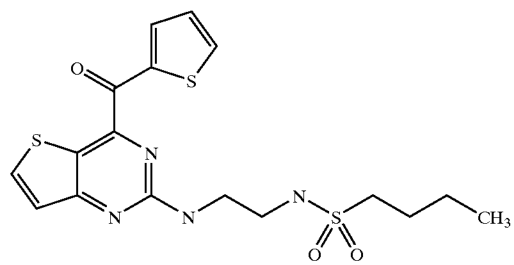 | N-(2-(4-(2-Thienylcarbonyl)thieno[3,2-d]pyrimidin-2-yl)aminoethyl)butanesulphonamide |
| 169 | 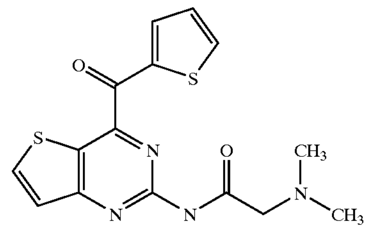 | 2-Dimethylamino-N-(4-(2-thienylcarbonyl)thieno[3,2-d]pyrimidin-2-yl)acetamide hydrochloride |
| 170 | 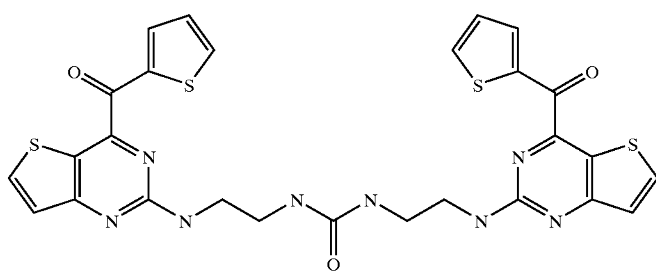 | N,N'-Bis(2-(4-(2-thienylcarbonyl)thieno[3,2-d]pyrimidin-2-yl)aminoethyl)urea |

Synthetic Methods

Method A

Phenyl 2-trifluoromethylthieno[3,2-d]pyrimidin-4-ylmethanone (Example 1)

A suspension of 4-chloro-2-trifluoromethylthieno[3,2-d]pyrimidine (0.3 g, 1.26 mmol), benzaldehyde (0.28 g, 2.64 mmol) and N,N-dimethylimidazolium iodide (0.2 g, 0.89 mmol) in THF (8 mL) was treated with NaH (60% dispersion in oil, 0.112 g, 2.8 mmol), refluxed for 15 min, cooled to room temperature, treated with water (4 mL) and the organic phase separated. The aqueous phase was extracted with $CH_2Cl_2$ (2×20 mL), the combined organic phase washed with brine (10 mL), dried ($MgSO_4$), concentrated in vacuo and the resulting brown oil purified by chromatography [$SiO_2$; heptane-EtOAc (3:1)] then recrystallised from heptane to give the title compound (280 mg, 43%) as yellow needles.

Method B

α-Phenyl-2-trifluoromethylthieno[3,2-d]pyrimidine-4-acetonitrile (Example 16)

A suspension of NaH (60% dispersion in oil, 60 mg, 1.5 mmol) in DMF (5 mL) and toluene (15 mL) at room temperature was treated with phenylacetonitrile (0.16 g, 1.37 mmol), stirred for 10 min, treated with a solution of 4-chloro-2-trifluoromethylthieno[3,2-d]pyrimidine (0.3 g, 126 mmol) in DMF (2 mL), stirred for 15 min, treated with water (5 mL) and the phases separated. The aqueous phase was extracted with EtOAc (2×50 mL), the combined organic phase washed with water (3×10 mL), brine (10 mL), dried ($MgSO_4$), concentrated in vacuo and the resulting orange oily solid crystallised from heptane to give the title compound (0.1 g, 25%) as a gold solid.

Method C

P-Phenyl-2-trifluoromethylthieno[3,2-d]pyrimidine-4-ethanol (Example 20)

A solution of ethyl α-phenyl-2-trifluoromethylthieno[3,2-d]pyrimidine-4-acetate (0.21 g, 0.57 mmol) in $Et_2O$ (5 mL) at −78° C. was treated dropwise with 1-M DIBAL in toluene (1.6 mL, 1.6 mmol), stirred at −78° C. for 15 min, warmed to room temperature, treated with water (2 mL) and extracted with $Et_2O$ (5 mL). The extract was washed with brine (10 mL), dried ($MgSO_4$), concentrated in vacuo, and purified by chromatography [$SiO_2$; heptane-EtOAc (3:1)] to give the title compound (67 mg, 36%) as a brown oil.

Method D

2-Ethyl-α-(2-thienyl)thieno[3,2-d]pyrimidine-4-methanol (Example 36)

A solution of 2-ethylthieno[3,2-d]pyrimidin-4-yl 2-thienylmethanone (170 mg, 0.6 mmol) in MeOH (10 mL) at room temperature was treated with NaBH (26 mg, 0.7 mmol), stirred for 1.5 h, concentrated in vacuo, treated with water (10 mL), extracted with EtOAc (2×10 mL) and purified by chromatography [$SiO_2$; EtOAc] to give the title compound (109 mg, 64 %) as a pale yellow solid.

Method E

Phenyl 2-trifluoromethylthieno[3,2-d]pyrimidin-4-ylmethanone oxime (Example 22)

A solution of phenyl 2-trifluoromethylthieno[3,2-d]pyrimidin-4-ylmethanone (60 mg, 0.19 mmol) and hydroxylamine hydrochloride (0.04 g, 0.58 mmol) in pyridine (2 mL) was refluxed for 1 h, concentrated in vacuo, treated with toluene (2 mL), concentrated in vacuo and the resulting solid dissolved in EtOAc (5 mL), washed with water (3 mL) and concentrated in vacuo to give the title compound (62 mg, 98%), a mixture of geometrical isomers, as an oily solid.

Method F
2-Ethylaminothieno[3,2-d]pyrimidin-4-yl 2-thienylmethanone (Example 49)

A suspension of 2-chlorothieno[3,2-d]pyrimidin-4-yl 2-thienylmethanone (0.196 g, 0.7 mmol) in EtOH (5 mL) was treated with 12.4-M ethylamine in water (0.06 mL, 0.7 mmol), refluxed for 16 h, cooled, treated with water (5 mL) and the resulting solid filtered and recrystallised [EtOAc-heptane] to give the title compound (0.138 g, 68%) as a yellow solid.

Method G
2-(2-Aminoethylamino)thieno[3,2-d]pyrimidin-4-yl 2-thienylmethanone dihydrochloride (Example 55)

A solution of 2-(2-butoxycarbonylaminoethylamino) thieno[3,2-d]pyrimidin-4-yl 2-thienylmethanone (58 mg, 0.14 mmol) in MeOH (5 mL) was treated with 4-M HCl in dioxane (0.5 mL), stirred at room temperature for 16 h and the resulting solid filtered and washed with ether to give the title compound (41 mg, 77%) as a white crystalline solid.

Method H
5-Dimethylamino-2-thienyl 2-trifluoromethylthieno[3,2-d]pyrimidin-4-ylmethanone (Example 56)

A suspension of 5-bromo-2-thienyl 2-trifluoromethylthieno[3,2-d]pyrimidin-4-ylmethanone (0.3 g, 0.76 mmol) in EtOH (20 mL) was treated with 40% aqueous dimethylamine (5 mL), refluxed for 1 h, cooled, treated with water (25 mL), concentrated in vacuo and the aqueous mixture extracted with EtOAc (2×25 mL), the combined extracts washed with brine (25 mL), dried ($MgSO_4$) and concentrated in vacuo. The resulting red oil was purified by chromatography [$SiO_2$; heptane-EtOAc (1:1)] to give the title compound (0.115 g, 42%) as a red solid.

Method I
5-Methoxy-2-thienyl 2-trifluoromethylthieno[3,2-d]pyrimidin-4-ylmethanone (Example 68)

A suspension of 5-bromo-2-thienyl 2-trifluoromethylthieno[3,2-d]pyrimidin-4-ylmethanone (0.2 g, 0.51 mmol) in MeOH (15 mL) was treated with sodium methoxide (0.11 g, 2.04 mmol), refluxed for 1 h, treated with dioxane (0.1 mL) to aid dissolution, refluxed for 18 h, cooled, treated with water (15 mL) and concentrated in vacuo. The resulting aqueous mixture was extracted with EtOAc (2×25 mL), the combined extracts washed with brine (25 mL), dried ($MgSO_4$), concentrated in vacuo and the resulting red oil dissolved in heptane-EtOAc (50:50), filtered through a pad of $SiO_2$, concentrated in vacuo and the resulting solid recrystallised [heptane-EtOAc (19:1)] to give the title compound (0.124 g, 71%) as a yellow solid.

Method J
2-Dimethylamino-7-phenylthieno[3,2-d]pyrimidin-4-yl 2-thienylmethanone (Example 71)

A solution of palladium(II) acetate (2.1 mg, 9.5 μmol) and triphenylphosphine (10.0 mg, 38 μmol) in DMF (1 mL) was stirred under an atmosphere of argon at room temperature for 5 min, treated with a solution of 7-bromo-2-dimethylaminothieno[3,2-d]pyrimidin-4-yl 2-thienylmethanone (0.07 g, 0.2 mmol) in DMF (4 mL), stirred for a further 5 min, treated with phenylboronic acid (0.46 g, 0.4 mmol) in EtOH (0.7 mL) followed by saturated $NaHCO_3$ (0.7 mL) and stirred at 80° C. for 2 h. The reaction mixture was cooled to room temperature, extracted with $Et_2O$ (2×5 mL), the combined organic phase washed with water (5 mL), dried ($MgSO_4$), concentrated in vacuo and the resulting residue purified by chromatography [$SiO_2$; heptane-EtOAc (95:5)] to give the title compound (61 mg, 87%) as an orange solid.

Method K
2-Dimethylamino-7-(2-furyl)thieno[3,2-d]pyrimidin-4-yl 2-thienylmethanone (Example 79)

A mixture of palladium(II) acetate (4.1 mg, 18.3 μmol) and triphenylarsine (22.4 mg, 73 μmol) in DMF (0.8 mL) was stirred under an atmosphere of argon at room temperature for 10 min, treated with a solution of 7-bromo-2-dimethylaminothieno[3,2-d]pyrimidin-4-yl 2-thienylmethanone (0.067 g, 0.18 mmol) in DMF (1.1 mL), stirred for 10 min then treated dropwise with 2-tri-n-butylstannylfuran (104 μL, 0.33 mmol). The reaction mixture was stirred at 100° C. for 117 h, cooled, poured into saturated $NH_4Cl$ (5 mL), extracted with EtOAc (4×5 mL), the combined organic phase washed with water (5 mL), dried ($MgSO_4$), concentrated in vacuo and the resulting residue purified by chromatography [$SiO_2$; heptane-EtOAc (100:0–95:5 gradient)] to give the title compound (57 mg, 87%) as an orange solid.

Method L
4-(2-Thienylcarbonyl)thieno[3,2-d]pyrimidine-2-carboxylic acid (Example 124)

A solution of ethyl 4-(2-thienylcarbonyl)thieno[3,2-d]pyrimidine-2-carboxylate (80 mg, 0.25 mmol) in MeOH (3 mL) was treated with 2M-NaOH (1 mL), stirred at room temperature for 20 min, acidified with 1M-HCl, diluted with water and filtered to give the title compound (36 mg, 50%) as a pale yellow solid.

Method M
Methyl 4-(2-thienylcarbonyl)thieno[3,2-d]pyrimidine-2-carboxylate (Example 126)

A solution of ethyl 4-(2-thienylcarbonyl)thieno[3,2-d]pyrimidine-2-carboxylate (100 mg, 0.31 mmol) in MeOH (5 mL) was refluxed for 2 h, cooled, diluted with water and filtered to give the title compound (73 mg, 74%) as a cream solid.

Method N
Methanesulphonic Acid 2-(4-(2-thienylcarbonyl)thieno[3,2-d]pyrimidin-2-yl)hydrazide (Example 128)

A mixture of 2-hydrazinothieno[3,2-d]pyrimidin-4-yl 2-thienylmethanone (110 mg, 0.4 mmol) and $Et_3N$ (61 μL, 0.44 mmol) in THF (5 mL) was treated with methanesulphonyl chloride (31 μl, 0.4 mmol), stirred at room temperature for 20 min, poured into water (25 mL), extracted with EtOAc (2×5 mL), dried ($MgSO_4$) and concentrated in vacuo. The crude product was purified by chromatography [$SiO_2$: (EtOAc) to give the title compound (92 mg, 65%) as an orange solid.

Method O
Acetic Acid 2-(4-(2-thieinylcarbonyl)thieno[3,2-d]pyrimidin-2-yl)hydrazide (Example 130)

A solution of 2-hydrazinothieno[3,2-d]pyrimidin-4-yl 2-thienylmethanone (83 mg, 0.3 mmol) in pyridine (5 mL) was treated with acetyl chloride (28 μl, 0.4 mmol), stirred at room temperature for 16 h, concentrated in vacuo and the resulting solid washed with water and EtOAc to give the title compound (42 mg, 44%) as a yellow solid.

Method P
N-Allyl-2-(4-(2-thienylcarbonyl)thieno[3,2-d]pyrimidin-2-yl)hydrazinecarboxamide (Example 131)

A mixture of 2-hydrazinothieno[3,2-d]pyrimidin-4-yl 2-thienylmethanone (100 mg, 0.36 mmol) and THF (5 mL) was treated with allyl isocyanate (32 μl, 0.36 mmol), stirred at room temperature for 1 h and filtered to give the title compound (88 mg, 68%) as a yellow solid.

Method Q
N-(2-Dimethylaminoethyl)-4-(2-thienylcarbonyl)thieno[3,2-d]pyrimidin-2-carboxamide (Example 134)

A mixture of 4-(2-thienylcarbonyl)thieno[3,2-d]pyrimidine-2-carboxylic acid ( 290 mg, 1.0 mmol) and $SOCl_2$ (4 mL) was refluxed for 30 min, concentrated in vacuo, and treated with $CH_2Cl_2$ (10 mL), $Et_3N$ (208 μL, 1.5 mmol) and N,N-dimethylethylenediamine (120 μL, 1.1 mmol). The reaction mixture was stirred at room temperature for 1 h, poured into sat. $NaHCO_3$, extracted with EtOAc (2×10 mL), dried ($MgSO_4$), concentrated in vacuo then triturated with EtOAc and filtered to give the title compound (234 mg, 65%) as a cream solid.

Method R
2-Aminothieno[3,2-d]pyrimidin-4-yl 2-thienylmethanone (Example 10)

A mixture of 2-[N-(3,4-dimethoxybenzyl)]aminothieno[3,2-d]pyrimidin-4-yl 2-thienylmethanone (0.06 g, 0.15 mmol) and TFA (2 mL) was refluxed for 2 h, cooled, concentrated in vacuo to half its original volume, diluted with $CH_2Cl_2$ (50 mL), washed with saturated sodium bicarbonate solution (3×25 mL) then brine (25 mL), dried ($MgSO_4$), concentrated in vacuo and purified by chromatography [$SiO_2$; heptane-EtOAc (3:1)] to give the title compound (40 mg, 100%) as a yellow solid.

Method S
N-Acetyl-N-(4-(2-thienylcarbonyl)thieno[3,2-d]pyrimidin-2-yl)acetamide (Example 137)

A mixture of 2-aminothieno[3,2-d]pyrimidin-4-yl 2-thienylmethanone (0.05 g, 0.19 mmol) and acetyl chloride (4.99 g, 0.063 mol) was refluxed for 5 h, cooled to room temperature, poured into water (50 mL) and extracted with EtOAc (3×30 mL). The organic phase was washed with saturated sodium bicarbonate solution (2×25 mL) and saturated brine (2×25 mL), dried ($MgSO_4$) and concentrated in vacuo to yield a brown solid which was purified by chromatography [$SiO_2$; heptane-EtOAc (2:1)] to give the title compound (40 mg, 60%) as a yellow solid.

Method T
N-(4-(2-Thienylcarbonyl)thieno[3,2-d]pyrimidin-2-yl)acetamide (Example 138)

A mixture of 2-aminothieno[3,2-d]pyrimidin-4-yl 2-thienylmethanone (0.07 g, 0.27 mmol), anhydrous pyridine (3 mL) and acetyl chloride (0.15 g, 1.88 mmol) was refluxed for 24 h, cooled to room temperature, poured into water (30 mL) and extracted with EtOAc (2×30 mL). The organic phase was washed with 1-M HCl (2×25 mL) and saturated brine (25 mL), dried ($MgSO_4$) and concentrated in vacuo to give a yellow solid which was purified by chromatography ($SiO_2$; heptane-EtOAc (2:1)] to give the title compound (50 mg, 58%) as a yellow solid.

Method U
3-Methyl-N-(2-(4-(2-thienylcarbonyl)thieno[3,2-d]pyrimidin-2-yl)aminoethyl)butanamide (Example 150)

A solution of 2-(2-aminoethylamino)thieno[3,2-d]pyrimidin-4-yl 2-thienylmethanone (50 mg, 0.16 mmol) in $CH_2Cl_2$ (2 mL) was treated with triethylammonium methylpolystyrene carbonate (80 mg, 0.25 mmol) then isovaleryl chloride (30 mg, 0.25 mmol) and shaken at room temperature for 6 h. The reaction mixture was treated with tris-(2-aminoethyl)amine polystyrene (0.20 g, 0.75 mmol), shaken at room temperature for 16 h, treated with polystyrene methylisocyanate (0.18 g, 0.25 mmol) and $CH_2Cl_2$ (2 mL), shaken for a further 6 h then filtered and concentrated in vacuo to give the title compound (35 mg, 55%) as a yellow solid.

Method V
N-Allyl-N'-(2-(4-(2-thienylcarbonyl)thieno[3,2-d]pyrimidin-2-yl)aminoethyl)urea (Example 159)

A solution of 2-(2-aminoethylamino)thieno[3,2-d]pyrimidin-4-yl 2-thienylmethanone (50 mg, 0.16 mmol) in anhydrous DMF (1 mL) was treated with allyl isocyanate (21 mg, 0.25 mmol), shaken at room temperature for 4 h, treated with tris-(2-aminoethyl)amine polystyrene (0.20 g, 0.75 mmol), shaken at 35° C. for 16 h, treated with polystyrene methylisocyanate (0.22 g, 0.32 mmol) and DMF (2 mL) and shaken for a further 6 h. The reaction mixture was filtered and concentrated in vacuo to give the title compound (55 mg, 86%) as a yellow solid.

Method W
N-Phenyl-N'-(2-(4-(2-thienylcarbonyl)thieno[3,2-d]pyrimidin-2-yl)aminoethyl)thiourea (Example 164)

A solution of 2-(2-aminoethylamino)thieno[3,2-d]pyrimidin-4-yl 2-thienylmethanone (50 mg, 0.16 mmol) in anhydrous DMF (1 mL) was treated with phenyl isothiocyanate (33 mg, 0.25 mmol), shaken at room temperature for 2 h, poured into water (20 mL) and the resulting yellow precipitate was filtered and dried in vacuo to give the title compound (44 mg, 61%) as a yellow solid.

Method X
2-Dimethylamino-N-(4-(2-thienylcarbonyl)thieno[3,2-d]pyrimidin-2-yl)acetamide hydrochloride (Example 169)

A solution of 2-aminothieno[3,2-d]pyrimidin-4-yl 2-thienylmethanone (0.15 g, 0.57 mmol) in anhydrous pyridine (6 mL) under argon at 0° C. was treated with N,N-dimethylglycinyl chloride hydrochloride (0.11 g, 0.69 mmol), warmed to room temperature, refluxed for 16 h, cooled, concentrated in vacuo and partitioned between 3-M HCl (25 mL) and EtOAc (25 mL). The aqueous phase was washed with EtOAc (25 mL), filtered through celite, basified to pH 12 with 10% aqueous sodium hydroxide and the resulting precipitate filtered and dried in vacuo to give a brown solid which was purified by chromatography [$SiO_2$; EtOAc-MeOH (100:0 to 85:15)]. The resulting yellow solid was dissolved in $CH_2Cl_2$ (5 mL), treated with 1-M HCl in ether (0.25 mL) and the resulting precipitate filtered and dried in vacuo to give the title compound (32 mg, 11%) as a yellow solid.

Method Y
N,N'-Bis(2-(4-(2-thienylcarbonyl)thieno[3,2-d]pyrimidin-2-yl)aminoethyl)urea (Example 170)

A solution of 2-(2-aminoethylamino)thieno[3,2-d]pyrimidin-4-yl 2-thienylmethanone (0.10 g, 0.33 mmol) in anhydrous DMF (4 mL) under argon was treated with 1,1-carbonyldiimidazole (0.05 g, 0.33 mmol), stirred for 2 h, treated with 2-(2-aminoethylamino)thieno[3,2-d]pyrimidin-4-yl 2-thienylmethanone (0.10 g, 0.33 mmol), stirred at room temperature for 4 h and then at 60° C. for 16 h, cooled, poured into water (25 mL) and the resulting orange suspension filtered and dried in vacuo to give the title compound (0.13 g, 31%) as an orange solid.

Method Z
4-Chloro-2-methylthieno[3,2-d]pyrimidine

A suspension of 4-hydroxy-2-methylthieno[3,2-d]pyrimidine (0.631 g, 3.8 mmol) in $POCl_3$ (10 mL, 400 mmol) was refluxed for 4 h, concentrated in vacuo, treated with saturated $NaHCO_3$ (20 mL), extracted with EtOAc (2×20 mL) and the combined extracts dried ($MgSO_4$) and concentrated in vacuo to give the title compound (0.645 g, 92% as a pale yellow solid: mp 82–84° C.; IR $v_{max}$ (Nujol)/$cm^{-1}$ 3073, 2925, 2855, 1566, 1515, 1460, 1378, 1344, 1307, 894 and 795; NMR $\delta_H$ (400 MHz, DMSO-$d_6$) 3.41 (3H, s), 7.72 (1H, d, J 5.0 Hz) and 8.61 (1H, d, J 5.0 Hz).

4-Chloro-2-n-propylthieno[3,2-d]pyrimidine

This was prepared from 4-hydroxy-2-n-propylthieno[3,2-d]pyrimidine by method Z and the title compound (0.91 g, 78%) isolated as a pale yellow oil: IR $\nu_{max}$ (Nujol)/cm$^{-1}$ 2963, 2932, 1564, 1514, 1459, 1338, 1322, 1100 and 799; NMR $\delta_H$ (400 MHz, CDCl$_3$) 1.04 (3H, t, J 7.5 Hz), 1.93 (2H, m), 3.04 (2H, t, J 7.5 Hz), 7.55 (1H, d, J 5.5 Hz) and 8.02 (1H, d, J 5.5 Hz).

Ethyl 4-chlorothieno[3,2-d]pyrimidine-2-carboxylate

This was prepared from ethyl 4-oxothieno[3,2-d]pyrimidine-2-carboxylate by method Z and the crude title compound (757 mg, quantitative) isolated as an off-white solid: IR $\nu_{max}$ (Nujol)/cm$^{-1}$ 3091, 3061, 2925, 2854, 1732, 1547, 1456, 1325 and 1196; NMR $\delta_H$ (400 MHz, CDCl$_3$) 1.49 (3H, t, J 7.1 Hz), 4.59 (2H, q, J 7.1 Hz), 7.80 (1H, d, J 5.5 Hz), and 8.17 (1H, d, J 5.5 Hz).

Method AA

Ethyl 4-oxothieno[3,2-d]pyrimidine-2-carboxylate

A mixture of 3-aminothiophene-2-carboxamide (1.23 g, 8.65 mmol) and EtOH (25 mL) was treated with NaOEt (1.2 g, 17.3 mmol) and diethyloxalate (2.3 mL, 17.3 mmol), refluxed for 18 h, cooled, concentrated in vacuo, treated with water, acidified with HOAc and filtered to give the title compound (1.43 g, 74%) as a cream solid: IR $\nu_{max}$ Nujol/cm$^{-1}$ 3180, 3119, 3078, 3006, 2955, 2924, 2854, 1737, 1667, 1651, 1300 and 1176; NMR $\delta_H$ (400 MHz, DMSO) 1.37 (3H, t, J 7.0 Hz), 4.40 (2H, q, J 7.0 Hz), 7.58 (1H, d, J 5.0 Hz), 8.30 (1H, d, J 5.1 Hz), and 12.92 (1H, s).

Experimental data for Examples 1–170 are provided in Table 2.

HPLC is carried out using the following conditions: Column. Supelcosil ABZ$^+$ (170×4.6 mm), particle size 5 $\mu$M, mobile phase MeOH: 10 mM aq NH$_4$OAc (8:2), (9:1) or (100:0) (specified in Table 2), flow rate 1.0 mL/min., detection wavelength $\lambda$=230 nM (unless otherwise stated), retention times are provided in Table 2.

TABLE 2

| Example | Method | Yield (%) | Physical Data |
| --- | --- | --- | --- |
| 1 | A | 43 | mp 116–118° C.; IR $\nu_{max}$ (Nujol)/cm$^{-1}$ 3138, 3103, 3088, 2924, 1635, 1507, 1443, 1422, 1282, 1245, 1189, 1165, 1092, 760, 734 and 602; NMR $\delta_H$ (400 MHz, CDCl$_3$) 7.42(1H, m), 7.78(1H, d, J 5.5Hz), 8.06(1H, m), 8.42(1H, d, J 5.5Hz) and 8.48(2H, d, J 1.5 Hz); Anal. Calcd for C$_{14}$H$_7$F$_3$N$_2$OS: C, 54.55; H, 2.19; N, 9.08. Found: C, 54.41; H, 2.29; N, 8.99. |
| 2 | A | 53 | mp 173–175° C.; IR $\nu_{max}$ (Nujol)/cm$^{-1}$ 3091, 1632, 1412, 1245, 1195, 1175, 1147, 1056, 771 and 739; NMR $\delta_H$ (400 MHz, CDCl$_3$) 7.30(1H, s), 7.79(1H, d, J 5.5Hz), 7.92(1H, m), 8.41(1H, d, J 5.5Hz) and 8.77(1H, m); Anal. Calcd for C$_{12}$H$_5$F$_3$N$_2$OS$_2$: C, 45.86; H, 1.60; N, 8.91; S, 20.40. Found: C, 45.90; H, 1.67; N, 8.84; S, 20.62. |
| 3 | A | 75 | mp 164–166° C.; IR $\nu_{max}$ (Nujol)/cm$^{-1}$ 3081, 2924, 1647, 1462, 1448, 1235, 1182, 1140, 824, 730 and 669; NMR $\delta_H$ (400 MHz, CDCl$_3$) 7.43(1H, m), 7.79(1H, d, J 5.6Hz), 8.06(1H, m), 8.39(1H, d, J 5.5Hz) and 9.48(1H, m); Anal. Calcd for C$_{12}$H$_5$F$_3$N$_2$OS$_2$: C, 45.86; H, 1.60; N, 8.91. Found: C, 45.78; H, 1.63; N, 8.83. |
| 4 | A | 40 | mp 190–192° C.; IR $\nu_{max}$ (Nujol)/cm$^{-1}$ 3167, 3148, 3089, 1639, 1463, 1441, 1177, 1153, 1137, 1086, 1046, 1016, 912, 820, 791, 772 and 736; NMR $\delta_H$ (400 MHz, CDCl$_3$) 6.74 (1H, m), 7.79(1H, d, J 5.5Hz), 7.88(1H, s), 8.41(1H, d, J 5.5Hz) and 8.63(1H, d, J 3.0Hz); Anal. Calcd for C$_{12}$H$_5$F$_3$N$_2$O$_2$S: C, 48.33; H, 1.69; N, 9.39. Found: C, 48.19; H, 1.75; N, 9.25. |
| 5 | A | 17 | mp 136–138° C.; IR $\nu_{max}$ (Nujol)/cm$^{-1}$ 3170, 3101, 3084, 1640, 1525, 1512, 1465, 1438, 1376, 1300, 1269, 1202, 1178, 1157, 1137, 1092, 998, 917, 873, 787, 778, 747, 735 and 598; NMR $\delta_H$ (400 MHz, CDCl$_3$) 6.92(1H, m), 7.56(1H, s), 7.79(1H, d, J 6Hz), 8.41 (1H, d, J 7Hz) and 9.30(1H, s); Anal. Calcd for C$_{12}$H$_5$F$_3$N$_2$O$_2$S: C, 48.33; H, 1.69; N, 9.39. Found: C, 48.40; H, 1.77; N, 9.22. |
| 6 | A | 8 | mp 230–233° C.; IR $\nu_{max}$ (Nujol)/cm$^{-1}$ 3288, 3087, 1608, 1535, 1465, 1440, 1381, 1199, 1184, 1143, 1049 and 765; NMR $\delta_H$ (400 MHz, CDCl$_3$) 6.45(1H, m), 7.30(1H, m), 7.50(0.5H, br s), 7.78(1H, d, J 5.5Hz), 8.41(1H, br m) and 9.70(0.5H, br s); Anal. Calcd for C$_{12}$H$_6$F$_3$N$_3$OS: C, 48.49; H, 2.03; N, 14.13. Found: C, 48.23; H, 2.06; N, 13.96. |
| 7 | A | 36 | mp 140–142° C; IR $\nu_{max}$ (Nujol)/cm$^{-1}$ 3113, 3077, 1679, 1461, 1440, 1410, 1378, 1363, 1273, 1247, 1203, 1177, 1151, 933, 815, 740 and 772; NMR $\delta_H$ (400 MHz, CDCl$_3$) 7.84 (1H, d, J 2.0Hz), 8.34(2H, d, J 5.5Hz), 8.38(1H, d, J 2.0Hz) and 8.68(2H, d, J 5.5 Hz). |
| 8 | A | 53 | mp 122–123° C.; IR $\nu_{max}$ (Nujol)/cm$^{-1}$ 3119, 3058, 1676, 1590, 1524, 1463, 1440, 1362, 1235, 1212, 1178, 1139, 1021, 931, 820, 747 and 650; NMR $\delta_H$ (400 MHz, CDCl$_3$) 7.4–7.6(3H, m), 7.68(1H, dd, J 7.0, 1.0Hz), 7.81(1H, d, J 6.0Hz) and 8.45(1H, d, J 7.0 Hz); Anal. Calcd for C$_{14}$H$_6$ClF$_3$N$_2$OS: C, 49.06; H, 1.76; N, 8.17. Found: C, 49.24; H, 1.85; N, 8.11. |
| 9 | A | 49 | mp 128–130° C.; IR $\nu_{max}$ (Nujol)/cm$^{-1}$ 3107, 3082, 1651, 1562, 1529, 1465, 1440, 1378, 1362, 1276, 1227, 1178, 1140, 1099, 1029, 847, 823, 773, 752, 731, 694, 672, 657 and 604; NMR $\delta_H$ (400 MHz, CDCl$_3$) 7.52(1H, t, J 8Hz), 7.68(1H, dd, J 2.5, 1.0Hz), 7.81 (1H, d, J 5.5Hz), 8.42(1H, d, J 5.5Hz), 8.46(1H, m) and 8.48(1H, d, J 1.0Hz); Anal. Calcd for C$_{14}$H$_6$ClF$_3$N$_2$OS: C, 49.06; H, 1.76; N, 8.17. Found: C, 48.90; H, 1.83; N, 8.00. |
| 10 | A | 41 | mp 147–149° C.; IR $\nu_{max}$ (Nujol)/cm$^{-1}$ 3105, 3085, 1650, 1562, 1535, 1443, 1379, 1361, 1280, 1225, 1178, 1100, 944, 817, 777, 719, 692 and 662; NMR $\delta_H$ (400 MHz, CDCl$_3$) 7.68(1H, d, J 1.5Hz), 7.83(1H, d, J 5.5Hz), 8.44(1H, d, J 5.5Hz), and 8.47(2H, d, J 1.5Hz); Anal. Calcd for C$_{14}$H$_5$Cl$_2$F$_3$N$_2$OS: C, 44.58; H, 1.34; N, 7.42. Found: C, 44.52; H, 1.33; N, 7.30. |
| 11 | A | 30 | mp 116–118° C.; IR $\nu_{max}$ (Nujol)/cm$^{-1}$ 3118, 3084, 2951, 1665, 1543, 1520, 1477, 1458, 1440, 1380, 1276, 1234, 1194, 1176, 1142, 1093, 930, 745 and 738; NMR $\delta_H$ (400 MHz, CDCl$_3$) 2.51(3H, s), 7.3–7.4(2H, m), 7.52(1H, t, J 7.5Hz), 7.78(2H, m) and 8.41(1H, d, J 6.0Hz); Anal. Calcd for C$_{15}$H$_9$F$_3$N$_2$OS: C, 55.90; H, 2.81; N, 8.69. Found: C, 55.94; H, 2.83; N, 8.69. |

TABLE 2-continued

| Example | Method | Yield (%) | Physical Data |
|---|---|---|---|
| 12 | A | 17 | 0.12 g, 17% mp 165–167° C.; IR $\nu_{max}$ (Nujol)/cm$^{-1}$ 3081, 1638, 1512, 1458, 1440, 1413, 1374, 1324, 1230, 1201, 1174, 1143, 933, 819, 803, 777, 760 and 739; NMR $\delta_H$ (400 MHz, CDCl$_3$) 7.14(1H, d, J 5.5Hz), 7.90(1H, d, J 3.5Hz), 8.42(1H, d, J 3.5Hz) and 8.47(1H, d, J 5.5Hz); Anal. Calcd for C$_{12}$H$_4$ClF$_3$N$_2$OS$_2$: C, 41.33; H, 1.16; N, 8.03. Found: C, 41.42; H, 1.23; N, 7.97. |
| 13 | A | 34 | mp 161–163° C.; IR $\nu_{max}$ (Nujol)/cm$^{-1}$ 3108, 3079, 1629, 1545, 1443, 1240, 1203, 1174, 1140, 1050, 933, 820, 778 and 762; NMR $\delta_H$ (400 MHz, CDCl$_3$) 2.64(3H, s), 6.98(1H, m), 7.78(1H, d, J 8.0Hz), 8.39(1H, d, J 8.0Hz) and 8.71(1H, m); Anal. Calcd for C$_{13}$H$_7$F$_3$N$_2$OS$_2$: C, 47.56; H, 2.15; N, 8.53. Found: C, 47.89; H, 2.28; N, 8.50. |
| 14 | A | 41 | mp 196–197° C.; IR $\nu_{max}$ (Nujol)/cm$^{-1}$ 3104, 3086, 3061, 1655, 1526, 1464, 1396, 1369, 1331, 1265, 1237, 1211, 1173, 1155, 937, 921, 804, 777 and 738; NMR $\delta_H$ (400 MHz, CDCl$_3$) 7.85(1H, d, J 5.5Hz), 7.94(1H, d, J 3.0Hz), 8.31(1H, d, J 3.0Hz) and 8.48 (1H, d, J 5.5Hz); Anal. Calcd for C$_{11}$H$_4$F$_3$N$_3$OS$_2$: C, 41.90; H, 1.28; N, 13.32. Found: C, 41.67; H, 1.34; N, 13.17. |
| 15 | A | 14 | mp 221–223° C.; IR $\nu_{max}$ (Nujol)/cm$^{-1}$ 3140, 3109, 3064, 2925, 2834, 1649, 1611, 1536, 1465, 1438, 1295, 1203, 1171, 1159, 1141, 1094, 1035, 917, 832, 814, 774, 753 and 733; NMR $\delta_H$ (400 MHz, CDCl$_3$) 7.40(1H, t, J 5.5Hz), 7.59(1H, t, J 5.5Hz), 7.68 (1H, d, J 8.0Hz), 7.81(1H, d, J 5.5Hz), 7.89(1H, d, J 8.0Hz), 8.43(1H, d, J 5.5Hz) and 8.95(1H, s); Anal. Calcd for C$_{16}$H$_7$F$_3$N$_2$O$_2$S: C, 55.18; H, 2.03; N, 8.04. Found: C, 55.16; H, 2.03; N, 7.98. |
| 16 | B | 25 | mp 142–143° C.; IR $\nu_{max}$ (Nujol)/cm$^{-1}$ 3096, 2249, 1533, 1526, 1456, 1142, 1202, 1176, 1142, 731, 706 and 698; NMR $\delta_H$ (400 MHz, CDCl$_3$) 5.64(1H, s), 7.4(3H, m), 7.6(2H, m), 7.71(1H, d, J 8.0Hz) and 8.14(1H, d, J 8.0Hz). |
| 17 | B | 41 | mp 157–159° C.; IR $\nu_{max}$ (Nujol)/cm$^{-1}$ 3113, 3098, 2251, 1554, 1525, 1483, 1442, 1439, 1275, 1201, 1177, 819, 771, 736 and 681; NMR $\delta_H$ (400 MHz, CDCl$_3$) 5.79(1H, s), 7.09(1H, m), 7.38(1H, m), 7.61(1H, m), 7.71(1H, d, J 5.5Hz) and 8.17(1H, d, J 8.0 Hz); Anal. Calcd for C$_{13}$H$_6$F$_3$N$_3$S$_2$: C, 48.00; H, 1.86; N, 12.91; S, 19.71. Found: C, 48.29; H, 1.95; N, 12.76; S, 19.70. |
| 18 | B | 12 | IR $\nu_{max}$ (Nujol)/cm$^{-1}$ 3118, 3100, 2184, 1630, 1589, 1551, 1463, 1377, 1283, 1187, 1176, 1145, 1136, 800, 768 and 740; NMR $\delta_H$ (400 MHz, CDCl$_3$) 5.31(1H, s), 6.94 (1H, m), 7.55(1H, d, J 8.0Hz), 7.66(1H, d, J 8.9Hz), 7.84(1H, m), 7.94(1H, d, J 6.0 Hz) and 7.99(1H, d, J 5.0Hz). |
| 19 | B | 59 | NMR $\delta_H$ (400 MHz, CDCl$_3$) 1.24(3H, t, J 8.0Hz), 4.2–4.4(1H, m), 5.48(1H, s), 7.38 (3H, m), 7.50(2H, m), 7.62(1H, d, J 5.5Hz) and 8.02(1H, d, J 5.5Hz). |
| 20 | C | 36 | NMR $\delta_H$ (400 MHz, CDCl$_3$) 3.31(1H, br s), 4.2(1H, m), 4.70(2H, s), 7.2–7.4(5H, m), 7.63(1H, d, J 5.5Hz) and 8.02(1H, d, J 5.5Hz). |
| 21 | D | 27 | NMR $\delta_H$ (400 MHz, CDCl$_3$) 4.40(1H, m), 6.10(1H, m), 7.35(3H, m), 7.50(2H, m), 7.66(1H, d, J 8.0Hz) and 8.10(1H, d, J 8.0Hz). |
| 22 | E | 98 | IR $\nu_{max}$ (Nujol)/cm$^{-1}$ 3199, 3108, 1547, 1522, 1458, 1399, 1261, 1201, 1177, 1146, 813, 740 and 718; NMR $\delta_H$ (400 MHz, CDCl$_3$) 7.35–7.55(5H, m), 7.73–7.77(1H, m) and 8.20–8.26(2H, m). |
| 23 | E | 95 | IR $\nu_{max}$ (Nujol)/cm$^{-1}$ 3186, 2955, 1544, 1523, 1416, 1385, 1256, 1201, 1169, 1142, 1038, 813, 786 and 740; NMR $\delta_H$ (400 MHz, CDCl$_3$) 7.19(0.5H, m), 7.30–7.50(1.5H, m), 7.70–7.90(1.5H, m), 8.10–8.30(2H, m) and 8.70(0.5H, br s). |
| 24 | A | 12 | mp 188–190° C.; IR $\nu_{max}$ (Nujol)/cm$^{-1}$ 3111, 3051, 2924, 1627, 1523, 1494, 1463, 1407, 1372, 1255, 1226, 1216, 1195, 1046, 970, 882, 786, 747 and 596; NMR $\delta_H$ (400 MHz, CDCl$_3$) 2.54(3H, s), 7.29(1H, t, J 5.5Hz), 7.88(1H, d, J 5.5Hz), 7.97(1H, s) and 8.69 (1H, d, J 4.0Hz); Anal. Calcd for C$_{12}$H$_7$ClN$_2$OS$_2$: C, 48.90; H, 2.39; N, 9.50. Found: C, 48.52; H, 2.36; N, 9.14. |
| 25 | A | 46 | mp 128–130° C.; IR $\nu_{max}$ (Nujol)/cm$^{-1}$ 3115, 3096, 2854, 1655, 1583, 1530, 1461, 1439, 1415, 1360, 1268, 1237, 1207, 1196, 1172, 1015, 934, 833, 812, 758, 737 and 688; NMR $\delta_H$ (400 MHz, CDCl$_3$) 7.51(1H, m), 7.84(1H, d, J 5.5Hz), 8.46(1H, d, J 5.5 Hz), 8.70–8.90(2H, m) and 9.71(1H, d, J 1.5Hz); Anal. Calcd for C$_{13}$H$_6$F$_3$N$_3$OS: C, 50.49; H, 1.96, N, 13.58. Found: C, 50.49; H, 1.88; N, 13.51. |
| 26 | A | 32 | mp 165–169° C.; IR $\nu_{max}$ (Nujol)/cm$^{-1}$ 3092, 3068, 2924, 1688, 1586, 1546, 1522, 1465, 1438, 1364, 1287, 1261, 1237, 1178, 1139, 1033, 936, 824, 808, 780, 751, 739, 694, 686 and 600; NMR $\delta_H$ (400 MHz, CDCl$_3$) 7.60(1H, m), 7.81(1H, d, J 5.5Hz), 7.99 (1H, m), 8.01(1H, d, J 2.4Hz), 8.38(1H, d, J 5.5Hz) and 8.84(1H, m); Anal. Calcd for C$_{13}$H$_6$F$_3$N$_3$OS: C, 50.49; H, 1.96, N, 13.58. Found: C, 50.61; H, 1.99; N, 13.38. |
| 27 | A | 65 | mp 155–157° C.; IR $\nu_{max}$ (Nujol)/cm$^{-1}$ 3106, 3092, 3076, 2955, 1636, 1596, 1567, 1535, 1508, 1464, 1440, 1424, 1360, 1288, 1266, 1240, 1173, 1138, 1018, 932, 848, 777, 738, 654 and 600; NMR $\delta_H$ (400 MHz, CDCl$_3$) 3.95(3H, s), 7.07(2H, d, J 12.0 Hz), 7.79(1H, d, J 5.5Hz), 8.40(1H, d, J 5.5Hz) and 8.62(2H, d, J 12.0Hz); Anal. Calcd for C$_{15}$H$_9$F$_3$N$_2$O$_2$S: C, 53.26; H, 2.68, N, 8.28. Found: C, 53.33; H, 2.62; N, 8.27. |
| 28 | A | 48 | mp 162.2–163.1° C.; IR $\nu_{max}$ (Nujol)/cm$^{-1}$ 3095, 3069, 2924, 2855, 1658, 1531, 1517, 1354, 1252 and 1208; NMR $\delta_H$ (400 MHz, CDCl$_3$) 7.55–7.59(2H, m), 7.62(1H, d, J 5.5Hz), 7.67–7.71(1H, m), 8.31(1H, d, J 5.5Hz) and 8.40–8.43(2H, m); ); Anal. Calcd for C$_{13}$H$_7$ClN$_2$OS: C, 56.84; H, 2.57; N, 10.19. Found: C, 56.79; H, 2.34; N, 10.13. |
| 29 | A | 54 | mp 127–129° C.; IR $\nu_{max}$ (Nujol)/cm$^{-1}$ 3099, 3071, 2923, 1645, 1601, 1530, 1460, 1440, 1392, 1358, 1279, 1232, 1210, 1184, 1169, 1132, 1096, 1018, 932, 843, 834, 778, 766, 735, 649, 596 and 562; NMR $\delta_H$ (400 MHz, CDCl$_3$) 2.48(3H, s), 7.43(2H, d, J 6.0Hz), 7.79(1H, d, J 5.5Hz), 8.38(1H, d, J 5.5Hz) and 8.45(2H, d, J 6.0Hz); Anal. Calcd for C$_{15}$H$_9$F$_3$N$_2$OS: C, 55.90; H, 2.81, N, 8.69. Found: C, 56.13; H, 2.74; N, 8.69. |
| 30 | A | 59 | mp 127–128° C.; IR $\nu_{max}$ (Nujol)/cm$^{-1}$ 3108, 3093, 3077, 2924, 1645, 1583, 1529, 1459, 1443, 1405, 1387, 1360, 1284, 1230, 1196, 1177, 1148, 1138, 1090, 1011, 933, 828, 813, 779, 770, 741, 645, 562 and 547; NMR $\delta_H$ (400 MHz, CDCl$_3$) 7.59(2H, d, J 11.0 |

TABLE 2-continued

| Example | Method | Yield (%) | Physical Data |
|---|---|---|---|
| | | | Hz), 7.77(1H, d, J 5.5Hz), 8.43(1H, d, J 5.5Hz) and 8.53(2H, d, J 11.0Hz); Anal. Calcd for $C_{14}H_6ClF_3N_2OS$: C, 49.06; H, 1.76; N, 8.17. Found: C, 48.93; H, 1.75; N, 8.17. |
| 31 | A | 17 | mp 185–186° C.; IR $\nu_{max}$ (Nujol)/cm$^{-1}$ 3104, 3077, 3053, 2955, 2925, 1675, 1600, 1531, 1519, 1442, 1345, 1318, 1281, 1234, 1191, 1176, 1145, 1031, 934, 823, 810 and 740; NMR $\delta_H$ (400 MHz, CDCl$_3$) 7.85(1H, d, J 5.5Hz), 8.40–8.60(3H, m) and 8.67(2H, d, J 11.0Hz); Anal. Calcd for $C_{14}H_6F_3N_3O_3S$: C, 47.60; H, 1.71; N, 11.89. Found: C, 47.47; H, 1.70; N, 11.69. |
| 32 | A | 39 | mp 131–133° C.; IR $\nu_{max}$ (Nujol)/cm$^{-1}$ 3106, 3079, 2924, 1649, 1598, 1530, 1480, 1462, 1439, 1384, 1360, 1281, 1247, 1190, 1142, 1098, 1047, 943, 821, 770, 755, 736, 678, 666 and 604; NMR $\delta_H$ (400 MHz, CDCl$_3$) 2.42(3H, s), 7.40–7.60(2H, m), 7.79(1H, d, J 5.5Hz), 8.20–8.30(2H, m) and 8.39(1H, d, J 5.5Hz); Anal. Calcd for $C_{15}H_9F_3N_2OS$: C, 55.90; H, 2.81, N, 8.69. Found: C, 55.87; H, 2.79; N, 8.69. |
| 33 | A | 14 | mp 117–120° C.; IR $\nu_{max}$ (Nujol)/cm$^{-1}$ 3082, 3042, 1691, 1606, 1572, 1528, 1448, 1394, 1357, 1276, 1255, 1231, 1210, 1168, 1080, 1025, 930, 902, 833, 815, 793, 766, 739, 695 and 684; NMR $\delta_H$ (400 MHz, CDCl$_3$) 7.16(1H, t, J 8.0Hz), 7.35(1H, d, J 8.0Hz), 7.45–7.55(1H, m), 7.83(1H, d, J 5.5Hz) and 8.42(1H, d, J 5.5Hz); Anal. Calcd for $C_{14}H_5ClF_4N_2OS$: C, 46.62; H, 1.40, N, 7.76. Found: C, 46.59; H, 1.42; N, 7.71. |
| 34 | B | 50 | mp 240–242° C.; IR $\nu_{max}$ (Nujol)/cm$^{-1}$ 3089, 2925, 2180, 1614, 1590, 1557, 1501, 1452, 1416, 1377, 1296, 1257 and 1234; NMR $\delta_H$ (400 MHz, CDCl$_3$) 1.50(3H, t, J 7.5Hz), 2.90(2H, q, J 7.5Hz), 6.99–7.02(1H, m), 7.28(1H, d, J 5.5Hz), 7.61–7.63(1H, m), 7.69–7.73(1H, m), 7.76(1H, d, J 5.5Hz) and 8.37(1H, d, J 5.5Hz); Anal. Calcd for $C_{15}H_{12}N_4S$: C, 64.27; H, 4.31, N, 19.98. Found: C, 64.53; H, 4.31; N, 19.96. |
| 35 | A | 66 | mp 111–112° C.; IR $\nu_{max}$ (Nujol)/cm$^{-1}$ 2925, 1632, 1621, 1550, 1498, 1463, 1408, 1378, 1364, 1342, 1296, 1429, 1190 and 1050; NMR $\delta_H$ (400 MHz, CDCl$_3$) 1.58(3H, t, J 7.5 Hz), 3.29(2H, q, J 7.5Hz), 7.24–7.27(1H, m), 7.57(1H, d, J 5.5Hz), 7.86(1H, dd, J 4.0, 1.0Hz), 8.18(1H, d, J 5.5Hz) and 8.63(1H, dd, J 4.0, 1.0Hz); Anal. Calcd for $C_{13}H_{10}N_2OS_2$: C, 56.91; H, 3.67; N, 10.21. Found: C, 56.96; H, 3.64; N, 10.23. |
| 36 | D | 64 | mp 147–149° C.; IR $\nu_{max}$ (Nujol)/cm$^{-1}$ 3134, 2924, 1535, 1460, 1381, 1359, 1310, 1264, 1224, 1138, 1106 and 1097; NMR $\delta_H$ (400 MHz, CDCl$_3$) 1.48(3H, t, J 7.5Hz), 5.52 (1H, br s), 6.23(1H, br s), 7.00(1H, dd, J 3.5, 1.5Hz), 7.23(1H, d, J 3.5Hz), 7.32(1H, dd, J 4.0, 1.0Hz), 7.50(1H, d J 5.5Hz) and 7.91(1H, d, J 5.5Hz); Anal. Calcd for $C_{13}H_{12}N_2OS_2$: C, 56.50; H, 4.38; N, 10.13. Found: C, 56.62; H, 4.40; N, 10.07. |
| 37 | F | 74 | mp 144–146° C.; IR $\nu_{max}$ (Nujol)/cm$^{-1}$ 3110, 3051, 3009, 1630, 1562, 1548, 1497, 1467, 1405, 1381, 1341, 1243, 1061, 1044, 852, 802, 761, 737 and 609; NMR $\delta_H$ (400 MHz, CDCl$_3$) 2.43(3H, s), 4.27(3H, s), 7.28(1H, m), 7.79(1H, s), 7.85(1H, m), and 8.59(1H, m); Anal. Calcd for $C_{13}H_{10}N_2O_2S_2$; C, 53.78; H, 3.47; N, 9.64. Found C, 53.25; H, 3.52; N, 9.47. |
| 38 | F | 68 | mp 156–158° C.; NMR $\delta_H$ (400 MHz, CDCl$_3$) 2.39(3H, s), 3.4(6H, s), 7.22(1H, m), 7.59(1H, s), 7.82(1H, m), and 8.42(1H, m). |
| 39 | F | 70 | mp 144–166° C.; IR $\nu_{max}$ (Nujol/cm$^{-1}$) 3067, 2923, 1625, 1566, 1499, 1463, 1410, 1377, 1309, 1249, 1214, 1045, 759, and 716; NMR $\delta_H$ (400 MHz, CDCl$_3$) 2.49(3H, s), 2.80 (3H, s), 7.24(1H, m), 7.51(1H, s), 7.83(1H, m) and 8.58(1H, m). |
| 40 | F | 76 | mp 116.5–117° C.; IR $\nu_{max}$ (Nujol)/cm$^{-1}$ 3051, 2924, 2854, 1657, 1559, 1355 and 733; NMR $\delta_H$ (400 MHz, CDCl$_3$) 3.27(6H, s), 7.28(1H, d, J 5.5Hz), 7.48–7.52(2H, m), 7.60–7.64(1H, m), 7.97(1H, d, J 5.5Hz) and 8.35–8.38(2H, m). |
| 41 | D | 63 | mp 157–158° C.; NMR $\delta_H$ (400 MHz, CDCl$_3$) 4.45(1H, br s), 6.39(1H, s), 6.98(1H, m), 7.22(1H, m), 7.34(1H, m), 7.70(1H, d, J 5.5Hz) and 8.13(1H, d, J 5.5Hz); Anal. Calcd for $C_{12}H_7F_3N_2OS_2$: C, 45.57; H, 2.23; N, 8.85. Found C, 45.79; H, 2.25; N, 8.82. |
| 42 | A | 18 | mp 201–202° C.; NMR $\delta_H$ (400 MHz, CDCl$_3$) 2.79(3H, s), 7.08(1H, d, J 5.5Hz), 7.6–7.8(2H, m) and 8.39(1H, d, J 5.5Hz); Anal. Calcd for $C_{13}H_7F_3N_2O_2S$; C, 47.56; H, 2.15; N, 8.53. Found C, 47.84; H, 2.17; N, 8.53. |
| 43 | A | 29 | mp 200–201° C.; NMR $\delta_H$ (400 MHz, CDCl$_3$) 2.52(3H, s), 6.37(1H, m), 7.78(1H, d, J 5.5Hz), 8.38(1H, d, J 5.5Hz) and 8.41(1H, d, J 4.8Hz); Anal. Calcd for $C_{13}H_7F_3N_2O_2S$: C, 50.00; H, 2.26; N, 8.97. Found C, 50.26; H, 2.26; N, 8.88. |
| 44 | A | 46 | mp 190.5–191° C.; IR $\nu_{max}$ (Nujol)/cm$^{-1}$ 3102, 3086, 2925, 1619, 1526, 1521, 1463, 1410, 1378, 1364, 1256, 765 and 734; NMR $\delta_H$ (400 MHz, CDCl$_3$) 7.28(1H, dd, J 4.6, 3.9Hz), 7.60(1H, d, J 5.5Hz), 7.89(1H, d, J 4.9Hz), 8.30(1H, d, J 5.5Hz) and 8.71 (1H, d, J 4.0Hz); Anal. Calcd for $C_{11}H_5ClN_2OS_2$: C, 47.06; H, 1.80, N, 9.97. Found: C, 46.84; H, 1.84; N, 9.87. |
| 45 | F | 76 | mp 203.1–204.2° C.; IR $\nu_{max}$ (Nujol)/cm$^{-1}$ 3085, 3065, 2924, 2854, 1637, 1573, 1537, 1506, 1462, 1411, 1373, 1251, 1048, 801, 765 and 717; NMR $\delta_H$ (400 MHz, CDCl$_3$) 3.39(6H, s), 7.23(1H, dd, J 4.6, 4.0Hz), 7.27(1H, d, J 5.5Hz), 7.81(1H, d, J 4.6Hz), 7.99(1H, d, J 5.5Hz) and 8.48(1H, d, J 4.0Hz); Anal. Calcd for $C_{10}H_{11}N_3OS_2$: C, 53.96; H, 3.83; N, 14.51. Found: C, 53.77; H, 3.78; N, 14.36. |
| 46 | A | 45 | mp 180–182° C.; NMR $\delta_H$ (400 MHz, CDCl$_3$) 7.26(1H, m), 7.80(1H, d, J 5.5Hz) and 8.3–8.4(2H, m); Anal. Calcd for $C_{12}H_4F_3BrN_2OS_2$; C, 36.66; H, 1.03; N, 7.12. Found C, 36.80; H, 1.15; N, 7.05. |
| 47 | F | 90 | mp 178.4–178.9° C.; IR $\nu_{max}$ (Nujol)/cm$^{-1}$ 3107, 3081, 2925, 2855, 1624, 1545, 1462, 1409, 1352, 1332 and 1230; NMR $\delta_H$ (400 MHz, CDCl$_3$) 4.24(3H, s), 7.25(1H, dd, J 5.1, 4.0Hz), 7.44(1H, d, J 5.5Hz), 7.84(1H, d, J 5.1Hz), 8.17(1H, d, J 5.5Hz) and 8.60(1H, d, J 4.0Hz); Anal. Calcd for $C_{12}H_8N_2O_2S_2$: C, 52.16; H, 2.92, N, 10.13. Found: C, 52.03; H, 3.00; N, 10.03. |

TABLE 2-continued

| Example | Method | Yield (%) | Physical Data |
|---|---|---|---|
| 48 | F | 90 | mp 189.7–190.6° C.; IR ν$_{max}$ (Nujol)/cm$^{-1}$ 3095, 3079, 2925, 2855, 1633, 1539, 1409, 1371, 1261, 1219 and 759; NMR δ$_H$ (400 MHz, CDCl$_3$) 2.79(3H, s), 7.26(1H, dd, J 5.0, 4.0Hz), 7.48(1H, d, J 5.5Hz), 7.85(1H, d, J 5.0Hz), 8.16(1H, d, J 5.5Hz) and 8.60(1H, d, J 4.0Hz); Anal. Calcd for C$_{12}$H$_8$N$_2$OS$_3$: C, 49.29; H, 2.76, N, 9.58. Found: C, 49.31; H, 2.76; N, 9.53. |
| 49 | F | 68 | mp 166.1–166.6° C.; IR ν$_{max}$ (Nujol)/cm$^{-1}$ 3287, 3104, 2925, 2855, 1634, 1589, 1462 and 1363; NMR δ$_H$ (400 MHz, CDCl$_3$) 1.36(3H, t, J 7.0Hz), 3.68(2H, q, J 7.0Hz), 5.22(1H, s), 7.21–7.26(2H, m), 7.81(1H, d, J 5.1Hz), 8.01(1H, d, J 5.5Hz) and 8.51(1H, d, J 4.0Hz); Anal. Calcd for C$_{13}$H$_{11}$N$_3$OS$_2$: C, 53.96; H, 3.83, N, 14.51. Found: C, 53.82; H, 3.62; N, 14.41. |
| 50 | F | 32 | mp 153.6–154.1° C.; IR ν$_{max}$ (Nujol)/cm$^{-1}$ 3258, 3101, 3024, 2925, 2855, 1635, 1598, 1407, 1366, 1350, 764 and 724; NMR δ$_H$ (400 MHz, CDCl$_3$) 4.87(2H, d, J 5.9Hz), 5.59 (1H, t, J 5.6Hz), 7.17(1H, t, J 4.2Hz), 7.25–7.34(2H, m), 7.37(2H, t, J 7.7Hz), 7.45 (2H, d, J 7.7Hz), 7.76(1H, d, J 5.1Hz), 8.04(1H, d, J 5.5Hz) and 8.40(1H, d, J 5.1 Hz); Anal. Calcd for C$_{18}$H$_{13}$N$_3$OS$_2$: C, 61.52; H, 3.73, N, 11.95. Found: C, 61.47; H, 3.52; N, 11.88. |
| 51 | F | 57 | mp 162.8–163.3° C.; IR ν$_{max}$ (Nujol)/cm$^{-1}$ 3300–3100, 2925, 2855, 1632, 1576, 1409, 1368, 764 and 726; NMR δ$_H$ (400 MHz, CDCl$_3$) 2.62–3.08(1H, s), 3.81(2H, q, J 5.5 Hz), 3.96(2H, q, J 5.2Hz), 5.67(1H, t, J 5.6Hz), 7.21–7.25(2H, m), 7.81(1H, d, J 4.0Hz), 8.02(1H, d, J 5.5Hz) and 8.48(1H, d, J 4.0Hz); Anal. Calcd for C$_{13}$H$_{11}$N$_3$O$_2$S$_2$: C, 51.13; H, 3.63, N, 13.75. Found: C, 51.27; H, 3.46; N, 13.70. |
| 52 | A | 54 | IR ν$_{max}$ (Nujol)/cm$^{-1}$ 2925, 2855, 1625, 1506, 1461, 1411, 1370 and 763; NMR δ$_H$ (400 MHz, CDCl$_3$) 2.99(3H, s), 7.23(1H, dd, J 5.0, 4.0Hz), 7.53(1H, d, J 5.5Hz), 7.82 (1H, dd, J 5.0, 1.5Hz), 8.14(1H, d, J 5.0Hz) and 8.62(1H, dd, J 4.0, 1.5Hz); Anal. Calcd for C$_{12}$H$_8$N$_2$OS$_2$: C, 55.36; H, 3.10; N, 10.76. Found: C, 55.45; H, 3.13; N, 10.74. |
| 53 | D | 48 | mp 144–146° C.; IR ν$_{max}$ (Nujol)/cm$^{-1}$ 2925, 2855, 1559, 1523, 1463, 1379, 1349, 764 and 715; NMR δ$_H$ (400 MHz, CDCl$_3$) 2.76(3H, s), 6.23(1H, d, J 3.5Hz), 7.00(1H, dd, J 5.0, 3.5Hz), 7.14(1H, dt, J 3.5, 1.0Hz), 7.21(1H, d, J 3.5Hz), 7.48(1H, dd, J 5.0, 1.0Hz), 7.58(1H, d J 5.5Hz) and 8.40(1H, d, J 5.5Hz); Anal. Calcd for C$_{12}$H$_{10}$N$_2$OS$_2$: C, 54.94; H, 3.84; N, 10.68. Found: C, 54.76; H, 3.94; N, 10.67. |
| 54 | F | 72 | mp 199.9–200.7° C.; IR ν$_{max}$ (Nujol)/cm$^{-1}$ 3385, 3043, 2925, 2854, 1679, 1642, 1571, 1546, 1521, 1459 and 1366; NMR δ$_H$ (400 MHz, CDCl$_3$) 1.42(9H, s), 3.49–3.51(2H, m), 3.74–3.78(2H, m), 4.90–5.04(1H, s), 5.53–5.68(1H, s), 7.21–7.25(2H, m), 7.81(1H, d, J 5.0Hz), 8.02(1H, d, J 5.5Hz) and 8.49(1H, d, J 5.0Hz); Anal. Calcd for C$_{18}$H$_{20}$N$_4$O$_3$S$_2$: C, 53.45; H, 4.98, N, 13.84. Found: C, 53.48; H, 4.98; N, 13.76. |
| 55 | G | 77 | mp >190° C. dec.; IR ν$_{max}$ (Nujol)/cm$^{-1}$ 3186, 3103, 3066, 2922, 2854, 2422, 1624, 1462, 1407, 1377, 1347 and 1320; NMR δ$_H$ (400 MHz, DMSO-d$_6$) 3.18–3.24(2H, m), 3.72–3.84(2H, m), 7.41–7.45(2H, m), 7.65–7.88(1H, s), 8.08–8.26(2H, s), 8.32 (1H, d, J 4.0Hz), 8.53(1H, d, J 5.5Hz) and 8.59–8.78(1H, s); Anal. Calcd for C$_{13}$H$_{12}$N$_4$O$_2$S$_2$.0.5H$_2$O.2.1HCl: C, 40.04; H, 3.90, N, 14.37; Cl, 19.09. Found: C, 39.62; H, 3.87; N, 14.04; Cl, 19.20. |
| 56 | H | 42 | mp 188–191° C.; IR ν$_{max}$ (Nujol)/cm$^{-1}$ 3060, 1592, 1533, 1492, 1465, 1409, 1378, 1321, 1172, 1136, 1085, 919 and 737; NMR δ$_H$ (400 MHz, CDCl$_3$) 3.20(6H, s), 6.15(1H, br s) 7.70(1H, d, J 5.5Hz), 8.33(1H, d, J 5.5Hz), 8.33(0.5H, br s) and 9.05(0.5H, br s); Anal. Calcd for C$_{14}$H$_{10}$F$_3$N$_3$OS$_2$: C, 47.05; H, 2.82; N, 11.75. Found: C, 46.69; H, 2.85; N, 11.20; M/Z 358 (M+H)$^+$. |
| 57 | A | 44 | mp 178–179° C.; NMR δ$_H$ (400 MHz, CDCl$_3$) 7.70(1H, d, J 1.4Hz), 7.80(1H, d, J 5.5 Hz), 8.43(1H, d, J 5.6Hz) and 8.57(1H, d, J 1.4Hz); Anal. Calcd for C$_{12}$H$_4$F$_3$BrN$_2$OS$_2$: C, 36.66; H, 1.03; N, 7.12. Found C, 36.76; H, 1.21; N, 7.09. |
| 58 | F | 50 | mp 200.4–200.9° C.; IR ν$_{max}$ (Nujol)/cm$^{-1}$ 3275, 3115, 2924, 2855, 1630, 1598, 1558, 1504, 1464 and 1363; NMR δ$_H$ (400 MHz, CDCl$_3$) 3.23(3H, d, J 5.0Hz), 5.26–5.30 (1H, m), 7.22–7.27(2H, m), 7.82(1H, d, J 5.5Hz), 8.02(1H, d, J 5.5Hz) and 8.53 (1H, d, J 5.0Hz); Anal. Calcd for C$_{14}$H$_{13}$N$_3$OS$_2$.0.3H$_2$O: C, 54.45; H, 4.44; N, 13.61. Found: C, 54.77; H, 4.65; N, 13.35. |
| 59 | F | 38 | mp 142.1–142.9° C.; IR ν$_{max}$ (Nujol)/cm$^{-1}$ 3265, 3125, 3074, 2925, 2855, 1634, 1593, 1561, 1461, 1408 and 1365; NMR δ$_H$ (400 MHz, CDCl$_3$) 4.29–4.34(2H, m), 5.21(1H, d, J 9.1Hz), 5.34–5.38(2H, m), 6.06–6.14(1H, m), 7.23–7.27(2H, m), 7.83(1H, d, J 5.0Hz), 8.04(1H, d, J 5.5Hz) and 8.52(1H, d, J 5.0Hz); Anal. Calcd for C$_{14}$H$_{11}$N$_3$OS$_2$: C, 55.79; H, 3.68, N, 13.94. Found: C, 55.59; H, 3.79; N, 13.64. |
| 60 | B | 51 | mp 185–187° C.; IR ν$_{max}$ (Nujol)/cm$^{-1}$ 3079, 2925, 2855, 2182, 1608, 1587, 1454 and 784; NMR δ$_H$ (400 MHz, CDCl$_3$) 1.08(3H, t, J 7.5Hz), 1.95(2H, m), 2.82(2H, t, J 7.5 Hz), 7.02(1H, ddd, J 9.0, 5.0, 1.0Hz), 7.31(1H, d, J 5.5Hz), 7.64(1H, dt, J 8.0, 1.0 Hz), 7.73(1H, ddd, J 9.0, 8.0, 2.0Hz), 7.78(1H, d, J 5.5Hz) and 8.38(1H, d, J 5.0 Hz); Anal. Calcd for C$_{16}$H$_{14}$N$_4$S: C, 65.28; H, 4.79; N, 19.03. Found: C, 65.09; H, 4.72; N, 18.84. |
| 61 | F | 20 | mp 134.8–135.6° C.; IR ν$_{max}$ (Nujol)/cm$^{-1}$ 3380, 3087, 2956, 2925, 2854, 1623, 1572, 1519, 1408 and 1365; NMR δ$_H$ (400 MHz, CDCl$_3$) 1.35(6H, d, J 6.5Hz), 4.36–4.45 (1H, m), 5.11(1H, d, J 7.4Hz), 7.21–7.25(2H, m), 7.81(1H, d, J 6.0Hz), 8.00(1H, d, J 5.5Hz) and 8.50(1H, d, J 4.0Hz). |
| 62 | A | 5 | mp 262–263° C.; NMR δ$_H$ (400 MHz, CDCl$_3$) 3.30(3H, s), 7.49(1H, t, J 12.0Hz), 7.56(2H, t, J 12.0Hz), 7.70(1H, d, J 5.5Hz), 8.2–8.0(2H, m) and 8.41(1H, d, J 5.5Hz); Anal. Calcd for C$_{17}$H$_9$F$_3$N$_2$OS$_2$: C, 53.96; H, 2.40; N, 7.40. Found C, 53.86; H, 2.33; N, 7.27. |

TABLE 2-continued

| Example | Method | Yield (%) | Physical Data |
|---|---|---|---|
| 63 | A | 13 | mp 122–125° C.; IR $\nu_{max}$ (Nujol)/cm$^{-1}$ 2956, 2925, 2855, 1633, 1551, 1505, 1464, 1409, 1378, 1236, 762 and 729; NMR $\delta_H$ (400 MHz, CDCl$_3$) 1.07(3H, t, J 7.5Hz), 2.06(2H, m), 3.22(2H, t, J 7.5Hz), 7.24(1H, dd, J 5.0, 4.0Hz), 7.50(1H, d, J 5.5Hz), 7.83(1H, dd, J 5.0, 1.0Hz), 8.14(1H, d, J 5.5Hz) and 8.60(1H, dd, J 4.0, 1.0Hz); Anal. Calcd for C$_{14}$H$_{12}$N$_2$OS$_2$: C, 58.31; H, 4.20; N, 9.71. Found: C, 58.53; H, 4.24; N, 9.69. |
| 64 | B | 62 | mp 266–269° C.; IR $\nu_{max}$ (Nujol)/cm$^{-1}$ 3078, 2925, 2855, 2180, 1613, 1590, 1503, 1454 and 783; NMR $\delta_H$ (400 MHz, CDCl$_3$) 2.60(3H, s), 7.02(1H, m), 7.29(1H, d, J 5.0Hz), 7.63(1H, d, J 8.5Hz), 7.73(1H, m), 7.78(1H, d, J 5.0Hz) and 8.39(1H, d, J 5.0Hz); Anal. Calcd for C$_{14}$H$_{10}$N$_4$S: C, 63.14; H, 3.80; N, 21.04. Found: C, 63.21; H, 3.78; N, 21.13. |
| 65 | F | 19 | mp 135.6–135.9° C.; IR $\nu_{max}$ (Nujol)/cm$^{-1}$ 3300–3100, 3094, 3080, 2925, 2854, 1635, 1578, 1367, 1239 and 763; NMR $\delta_H$ (400 MHz, CDCl$_3$) 3.43(3H, s), 3.69(2H, t, J 5.3 Hz), 3.84(2H, q, J 5.4Hz), 5.60(1H, t, J 5.6Hz), 7.21–7.25(2H, m), 7.81(1H, d, J 5.0Hz), 8.02(1H, d, J 5.5Hz) and 8.50(1H, d, J 5.0Hz); Anal. Calcd for C$_{14}$H$_{13}$N$_3$O$_2$S$_2$.0.4H$_2$O: C, 51.48; H, 4.26; N, 12.87. Found: C, 51.77; H, 4.60; N, 12.48. |
| 66 | F | 24 | mp >150° C. dec.; NMR $\delta_H$ (400 MHz, DMSO-d$_6$) 2.92(3H, s), 2.93(3H, s), 3.41–3.48 (2H, m), 3.92–3.40(2H, m), 7.43–7.46(2H, m), 7.78–7.96(1H, s), 8.33(1H, d, J 5.0Hz), 8.54(1H, d, J 5.5Hz) 8.65–8.70(1H, s) and 10.01–10.27(1H, br s). |
| 67 | D | 99 | IR $\nu_{max}$ (Nujol)/cm$^{-1}$ 3069, 2928, 2855, 1533, 1462, 1369 and 696; NMR $\delta_H$ (400 MHz, CDCl$_3$) 0.96(3H, t, J 7.5Hz), 1.84(2H, m), 2.94(2H, t, J 7.5Hz), 6.19(1H, dd, J 4.0, 1.0Hz), 6.96(1H, dd, J 5.0, 3.5Hz), 7.08(1H, dt, J 3.5, 1.0Hz), 7.18(1H, d, J 4.0Hz), 7.43(1H, dd, J 5.0, 1.0Hz), 7.54(1H, d J 5.5Hz) and 8.42(1H, d, J 5.5Hz). |
| 68 | I | 71 | mp 160–162° C.; IR $\nu_{max}$ (Nujol)/cm$^{-1}$ 3076, 1620, 1543, 1529, 1463, 1414, 1402, 1342, 1202, 1174, 1139, 1049, 817, 801, 770, 757 and 570; NMR $\delta_H$ (400 MHz, CDCl$_3$) 4.08 (3H, s), 6.25(1H, d, J 4.5Hz), 7.60(1H, d, J 5.6Hz), 8.36(1H, d, J 5.6Hz) and 8.68 (1H, br s); Anal. Calcd for C$_{13}$H$_7$F$_3$N$_2$O$_2$S$_2$: C, 45.35; H, 2.05; N, 8.13. Found: C, 45.34; H, 2.10; N, 8.15. |
| 69 | A | 26 | IR $\nu_{max}$ (Nujol)/cm$^{-1}$ 3065, 2923, 2854, 1624, 1533, 1465, 1409, 1377, 1257, 1059 and 728; NMR $\delta_H$ (400 MHz, CDCl$_3$) 7.29(1H, dd, J 4.0, 5.0Hz), 7.92(1H, dd, J 1.0, 5.0 Hz), 8.27(1H, s) and 8.73(1H, dd, J 1.0, 4.0Hz). |
| 70 | F | 84 | IR $\nu_{max}$ (Nujol)/cm$^{-1}$ 3093, 2923, 2854, 1629, 1573, 1499, 1463, 1404, 1371, 1248, 1193, 1056 and 732; NMR $\delta_H$ (400 MHz, CDCl$_3$) 3.43(6H, s), 7.29(1H, dd, J 4.0, 5.0 Hz), 7.82(1H, dd, J 1.0, 5.0Hz), 7.96(1H, s) and 8.48(1H, dd, J 1.0, 4.0Hz). |
| 71 | J | 87 | IR $\nu_{max}$ (Nujol)/cm$^{-1}$ 2295, 2854, 1624, 1567, 1534, 1462, 1409, 1368, 1250, 1194, 1049 and 763; NMR $\delta_H$ (400 MHz, CDCl$_3$) 3.41(6H, s), 7.24(1H, dd, J 4.0, 5.0Hz), 7.37 (1H, tt, J 1.0, 7.5Hz), 7.45–7.50(2H, m), 7.82(1H, dd, J 1.0, 5.0Hz), 8.05–8.09(2H, m), 8.11(1H, s) and 8.50(1H, dd, J 1.0, 4.0Hz). |
| 72 | F | 32 | mp 114.1–114.9° C.; IR $\nu_{max}$ (Nujol)/cm$^{-1}$ 3300–3210, 3102, 2925, 2855, 1656, 1581, 1552, 1461, 1339 and 1229; NMR $\delta_H$ (400 MHz, CDCl$_3$) 2.97–3.29(1H, m), 3.68–3.72(2H, m), 3.87–3.90(2H, m), 5.63(1H, t, J 5.2Hz), 7.28(1H, d, J 5.5Hz), 7.49–7.54(2H, m), 7.61–7.67(1H, m), 8.02(1H, d, J 5.5Hz) and 8.26–8.30(2H, m). |
| 73 | F | 24 | mp 164.6–165.4° C.; IR $\nu_{max}$ (Nujol)/cm$^{-1}$ 3064, 2925, 2855, 1632, 1558, 1410, 1375, 1339, 1235 and 1049; NMR $\delta_H$ (400 MHz, CDCl$_3$) 1.56(3H, t, J 6.8Hz), 4.67(2H, q, J 7.1Hz), 7.24–7.26(1H, m), 7.42(1H, d, J 5.5Hz), 7.84(1H, d, J 4.0Hz), 8.16(1H, d, J 5.5Hz) and 8.58(1H, d, J 4.0Hz); Anal. Calcd for C$_{13}$H$_{10}$N$_2$O$_2$S$_2$: C, 53.78; H, 3.47, N, 9.64. Found: C, 53.55; H, 3.51; N, 9.57. |
| 74 | A | 8 | mp 185–186° C.; IR $\nu_{max}$ (Nujol)/cm$^{-1}$ 3082, 2955, 1630, 1626, 1504, 1306, 1219, 1202, 1178, 1166, 1144, 1132, 922, 806 and 775; NMR $\delta_H$ (400 MHz, CDCl$_3$) 2.12(3H, s), 2.43(3H, s), 7.80(1H, d, J 5.5Hz) and 8.30–8.45(2H, m). |
| 75 | F | 99 | mp 146.5–148.1° C.; IR $\nu_{max}$ (Nujol)/cm$^{-1}$ 4329, 4259, 2920, 2669, 1621, 1562, 1463 and 1377; NMR $\delta_H$ (400 MHz, DMSO) 2.85(3H, s), 2.86(3H, s), 3.36(3H, s), 3.42 (1H, q, J 6.2Hz), 4.19(1H, t, J 6.0Hz), 7.38–7.40(2H, m), 8.26(1H, d, J 3.5Hz), 8.46(1H, d, J 3.0Hz) and 8.49(1H, d, J 5.5Hz). |
| 76 | F | 26 | mp 143.3–143.7° C.; IR $\nu_{max}$ (Nujol)/cm$^{-1}$ 3262, 3119, 2924, 2854, 1729, 1628, 1594, 1557 and 1367; NMR $\delta_H$ (400 MHz, CDCl$_3$) 1.25(3H, t, J 7.2Hz), 2.09(2H, quin, J 7.1 Hz), 2.49(2H, t, J 7.3Hz), 3.72(2H, q, J 6.5Hz), 4.14(2H, q, J 7.2Hz), 5.35–5.43 (1H, m), 7.22–7.28(2H, m), 7.83(1H, d, J 5.0Hz), 8.03(1H, d, J 5.5Hz) and 8.51 (1H, d, J 4.0Hz). Anal. Calcd for C$_{17}$H$_{17}$N$_3$O$_3$S$_2$: C, 54.38; H, 4.56; N, 11.19. Found: C, 54.28; H, 4.53; N, 11.02. |
| 77 | F | 91 | mp 199.9–200.5° C.; IR $\nu_{max}$ (Nujol)/cm$^{-1}$ 3079, 3064, 2923, 2854, 1620, 1562, 1497, 1465, 1415, 1376, 1264 and 765; NMR $\delta_H$ (400 MHz, CDCl$_3$) 3.88(4H, t, J 4.7Hz), 4.0 (4H, t, J 5.0Hz), 7.22–7.28(2H, m), 7.82(1H, d, J 5.0Hz), 8.02(1H, d, J 6.0Hz), 8.43(1H, dd, J 3.7, 1.4Hz). Anal. Calcd for C$_{15}$H$_{13}$N$_3$O$_2$S$_2$: C, 54.36; H, 3.95; N, 12.67. Found: C, 54.40; H, 3.88; N, 12.52. |
| 78 | F | 60 | mp >120° C. dec; IR $\nu_{max}$ (Nujol)/cm$^{-1}$ 3309, 3251, 3107, 3066, 2924, 2854, 1623, 1588, 1556, 1502, 1461, 1408, 1367 and 1234; NMR $\delta_H$ (400 MHz, DMSO) 3.11–3.23(2H, m), 3.41–3.49(2H, m), 3.55–3.65(2H, m), 3.75–4.04(7H, m), 7.35–7.41(2H, m), 7.78–7.86(1H, s), 8.26(1H, d, J 4.0Hz), 8.48(1H, d, J 5.5Hz), 8.54–8.69(1H, s) and 10.41–10.71(1H, s). |
| 79 | K | 87 | IR $\nu_{max}$ (Nujol)/cm$^{-1}$ 2925, 2855, 1632, 1568, 1535, 1504, 1458, 1410, 1370, 1249, 1193, 1056, 762, and 723; NMR $\delta_H$ (400 MHz, CDCl$_3$) 3.42(6H, s), 6.53(1H, dd, J 1.5, 3.0Hz), 7.22(1H, dd, J 4.0, 5.0Hz), 7.38(1H, d, J 3.0Hz), 7.47–7.49(1H, m), 7.80 (1H, dd, J 1.5, 5.0Hz), 8.16(1H, s) and 8.47(1H, dd, J 1.5, 4.0Hz). |
| 80 | K | 61 | IR $\nu_{max}$ (Nujol)/cm$^{-1}$ 2925, 2855, 1630, 1571, 1461, 1408, 1378, 1249, 1220, 1192, 1045, and 760; NMR $\delta_H$ (400 MHz, CDCl$_3$) 3.44(6H, s), 7.13(1H, dd, J 3.5, 5.0Hz), 7.23(1H, dd, J 4.0, 5.0Hz), 7.35(1H, dd, J 1.0, 5.0Hz), 7.81(1H, dd, J 1.5, 5.0Hz), 7.82(1H, dd, J 1.0, 3.5Hz), 8.10(1H, s) and 8.48(1H, dd, J 1.5, 4.0Hz). |

TABLE 2-continued

| Example | Method | Yield (%) | Physical Data |
|---|---|---|---|
| 81 | F | 67 | mp 214.6–215.3° C.; NMR $\delta_H$ (400 MHz, DMSO) 4.41(2H, s), 7.33–7.38(2H, m), 8.24(1H, d, J 5.1Hz), 8.44(1H, d, J 5.6Hz), 8.59(1H, s) and 8.72–8.75(1H, m). Anal. Calcd for $C_{11}H_8N_4OS_2$: C, 47.81; H, 2.92; N, 20.27. Found: C, 48.03; H, 2.96; N, 20.05. |
| 82 | F | 93 | IR $v_{max}$ (Nujol)/cm$^{-1}$ 3301, 1637, 1565, 1527, 1506, 1412, 1308, 1249, 1219, 1195, 1066, 1045 and 1026; NMR $\delta_H$ (400 MHz, CDCl$_3$) 3.46(3H, s), 4.00(4H, s), 7.23(1H, dd, J 4.0, 5.0Hz), 7.27(1H, m), 7.81(1H, dd, J 1.0, 5.0Hz), 8.00(1H, d, J 5.5Hz) and 8.45(1H, dd, J 1.0, 4.0Hz); Retention time: 3.10 min (9:1). |
| 83 | F | 93 | IR $v_{max}$ (Nujol)/cm$^{-1}$ 1627, 1562, 1529, 1504, 1412, 1300, 1267, 1248, 1196, 1147, 1096 and 1007; NMR $\delta_H$ (400 MHz, CDCl$_3$) 2.41(3H, s), 2.62(4H, t, J 5.0Hz), 4.08(4H, t, J 5.0Hz), 7.24(1H, dd, J 4.0, 5.0Hz), 7.26(1H, d, J 5.5Hz), 7.81(1H, dd, J 1.0, 5.0Hz), 8.00(1H, d, J 5.5Hz) and 8.42(1H, dd, J 1.0, 4.0Hz); Retention time: 3.77 min (9:1), detection wavelength λ 210 nm. |
| 84 | F | 94 | IR $v_{max}$ (Nujol)/cm$^{-1}$ 1675, 1626, 1565, 1527, 1497, 1411, 1263, 1169, 1134, 1048 and 989; NMR $\delta_H$ (400 MHz, CDCl$_3$) 1.52(9H, s), 3.61(4H, t, J 5.3Hz), 4.02(4H, t, J 5.0 Hz), 7.25(1H, dd, J 4.0, 5.0Hz), 7.27(1H, d, J 5.5Hz), 7.83(1H, dd, J 1.0, 5.0Hz), 8.03(1H, d, J 5.5Hz) and 8.41(1H, dd, J 1.0, 4.0Hz); Retention time: 2.89 min (10:0). |
| 85 | F | 92 | IR $v_{max}$ (Nujol)/cm$^{-1}$ 3347, 1634, 1562, 1506, 1412, 1340, 1322, 1241, 1224 and 1078; NMR $\delta_H$ (400 MHz, CDCl$_3$) 1.88(1H, m), 2.01–2.16(2H, m), 2.23(1H, m), 3.79–4.02(4H, m), 4.47(1H, m), 7.23(1H, dd, J 4.0, 5.0Hz), 7.26(1H, d, J 5.5Hz), 7.82 (1H, dd, J 1.0, 5.0Hz), 8.02(1H, d, J 5.5Hz) and 8.48(1H, dd, J 1.5, 4.0Hz); Retention time: 3.48 min (9:1). |
| 86 | F | 90 | IR $v_{max}$ (Nujol)/cm$^{-1}$ 3284, 1630, 1566, 1500, 1408, 1299, 1268, 1247, 1222, 1190 and 1052; NMR $\delta_H$ (400 MHz, CDCl$_3$) 1.67(2H, m), 2.06(2H, m), 3.53(2H, m), 4.05(4H, septet, J 4.0Hz), 4.60(1H, m), 4.64(1H, m), 7.24(1H, dd, J 4.0, 5.0Hz), 7.26(1H, d, J 5.5Hz), 7.81(1H, dd, J 1.5, 5.0Hz), 8.00(1H, d, J 5.5Hz) and 8.42(1H, dd, J 1.5, 4.0 Hz); Retention time: 3.36 min (9:1). |
| 87 | F | 84 | IR $v_{max}$ (Nujol)/cm$^{-1}$ 3385, 2727, 2475, 1629, 1609, 1563, 1499, 1453, 1409, 1278, 1231, 1163 and 1046; NMR $\delta_H$ (400 MHz, DMSO) 3.25(4H, m), 4.16(4H, m), 7.36 (1H, dd, J 4.0, 5.0Hz), 7.39(1H, d, J 5.5Hz), 8.21(1H, dd, J 1.0, 5.0Hz), 8.37(1H, dd, J 1.0, 4.0Hz), 8.50(1H, d, J 5.5Hz) and 9.50(2H, br s); Retention time: 3.27 min (8:2). |
| 88 | A | 18 | mp 194–195° C.; IR $v_{max}$ (Nujol)/cm$^{-1}$ 3076, 1626, 1534, 1521, 1457, 1400, 1354, 1268, 1042, 1012, 909, 786, 779 and 767; NMR $\delta_H$ (400 MHz, CDCl$_3$) 6.72(1H, m) 7.59(1H, d, J 5.6Hz), 7.86(1H, d, J 1.3Hz), 8.30(1H, d, J 5.6Hz) and 8.51(1H, d, J 1.3Hz),; Anal. Calcd for $C_{11}H_4Cl_2N_2OS_2$: C, 49.92; H, 1.90; N, 10.58. Found: C, 50.06; H, 1.96; N, 10.50. |
| 89 | F | 43 | IR $v_{max}$ (Nujol)/cm$^{-1}$ 3281, 1635, 1581, 1526, 1504, 1411, 1323, 1241, 1199, 1078 and 1049; NMR $\delta_H$ (400 MHz, CDCl$_3$) 1.38(3H, d, J 6.5Hz), 2.70(1H, dd, J 5.9 and 11.1Hz), 3.89(1H, dd, J 4.1 and 11.1Hz), 4.47(1H, m), 5.68(1H, br s), 7.24 (1H, dd, J 4.0, 5.0Hz), 7.25(1H, d, J 5.5Hz), 7.82(1H, dd, J 1.0, 5.0Hz), 8.03(1H, d, J 5.5Hz) and 8.48(1H, dd, J 1.0, 4.0Hz); Retention time: 3.61 min (8:2). |
| 90 | F | 70 | mp 212.2–212.5° C.; IR $v_{max}$ (Nujol)/cm$^{-1}$ 3288, 3082, 2924, 2854, 1636, 1568, 1533, and 1355; NMR $\delta_H$ (400 MHz, DMSO) 1.84(3H, s), 3.28–3.39(2H, m), 3.49–3.61(2H, m), 7.32(1H, d, J 5.5Hz), 7.37(1H, t, J 4.5Hz), 7.52–7.61(1H, m), 7.97–8.04(1H, m), 8.24(1H, d, J 4.5Hz), 8.42(1H, d, J 5.5Hz) and 8.50–8.72(1H, s). Anal. Calcd for $C_{15}H_{14}N_4O_2S_2$: C, 52.01; H, 4.07; N, 16.17. Found: C, 52.02; H, 4.09; N, 16.03. |
| 91 | A | 19 | mp 160–161° C.; IR $v_{max}$ (Nujol)/cm$^{-1}$ 3091, 1661, 1582, 1531, 1519, 1463, 1415, 1357, 1255, 1214, 1014, 931, 827, 762, 698 and 685; NMR $\delta_H$ (400 MHz, CDCl$_3$) 7.55(1H, m), 7.65(1H, d, J 5.6Hz), 8.35(1H, d, J 5.5Hz), 8.75(1H, m), 8.90(1H, m) and 9.65 (1H, b s); Anal. Calcd for $C_{11}H_5ClN_2O_2S$: C, 52.28; H, 2.19; N, 15.23. Found: C, 52.25; H, 2.22; N, 15.08. |
| 92 | F | 31 | IR $v_{max}$ (Nujol)/cm$^{-1}$ 3406, 1631, 1564, 1501, 1410, 1279, 1246, 1224, 1192 and 1054; NMR $\delta_H$ (400 MHz, DMSO) 1.16(6H, d, J 6.1Hz), 2.70(2H, m), 2.89(2H, m), 4.75 (2H, m), 6.50(1H, s), 7.36–7.42(2H, m), 8.27(1H, dd, J 1.0, 5.0Hz), 8.37(1H, dd, J 1.0, 4.0Hz) and 8.48(1H, d, J 5.5Hz); Retention time: 3.60 min (8:2). |
| 93 | F | 39 | IR $v_{max}$ (Nujol)/cm$^{-1}$ 3401, 1633, 1569, 1525, 1500, 1407, 1243, 1198 and 1052; NMR $\delta_H$ (400 MHz, CDCl$_3$) 3.44–3.62(6H, m), 3.77(1H, m), 7.29(2H, m), 7.33(1H, dd, J 4.0, 5.0Hz), 8.21(1H, dd, J 1.0, 5.0Hz), 8.38(1H, d, J 5.5Hz) and 8.64(1H, br s); Retention time: 2.87 min (8:2). |
| 94 | F | 66 | IR $v_{max}$ (Nujol)/cm$^{-1}$ 3278, 1621, 1588, 1557, 1521, 1497, 1409, 1326, 1245, 1223, 1199, 1077 and 1049; NMR $\delta_H$ (400 MHz, CDCl$_3$) 1.73(1H, m), 1.95(2H, m), 2.07 (1H, m), 3.67(1H, m), 3.82(1H, m), 3.88(1H, m), 3.96(1H, m), 4.23(1H, m), 5.71 (1H, br s), 7.23(1H, dd, J 4.0, 5.0Hz), 7.25(1H, d, J 5.5Hz), 7.81(1H, dd, J 1.0, 5.0 Hz), 8.02(1H, d, J 5.5Hz) and 8.50(1H, dd, J 1.0, 4.0Hz); Retention time: 4.97 min (8:2). |
| 95 | F | 24 | mp 178.6–179.3° C.; IR $v_{max}$ (Nujol)/cm$^{-1}$ 3261, 2924, 2854, 1629, 1590, 1556, 1409, and 1367; NMR $\delta_H$ (400 MHz, DMSO) 4.82(2H, d, J 5.5Hz), 7.27(2H, app t, J 3.0 Hz), 7.34(1H, d, J 5.5Hz), 7.74(1H, t, J 8.8Hz), 8.11–8.23(2H, m), 8.43(1H, d, J 5.6Hz), and 8.56(1H, d, J 4.1Hz). Anal. Calcd for $C_{17}H_{12}N_4OS_2 \cdot 0.25H_2O$: C, 57.20; H, 3.53; N, 15.70. Found: C, 57.03; H, 3.37; N, 15.60. |
| 96 | F | 22 | mp >140° C. dec; IR $v_{max}$ (Nujol)/cm$^{-1}$ 3261, 3104, 2925, 2854, 1630, 1591, 1555, and 1365; NMR $\delta_H$ (400 MHz, DMSO) 4.71(2H, d, J 5.4Hz), 6.31(1H, 1H, d, J 3.1Hz), 6.38–6.41(1H, m), 7.34–7.37(2H, m), 7.60–7.61(1H, m), 8.04(1H, t, J 5.9Hz), 8.23(1H, d, J 5.1Hz), and 8.55–8.71(1H, s). Anal. Calcd for $C_{16}H_{11}N_3O_2S_2 \cdot 0.5H_2O$: C, 54.84; H, 3.45; N, 11.99. Found: C, 54.62; H, 3.31; N, 11.89. |

TABLE 2-continued

| Example | Method | Yield (%) | Physical Data |
|---|---|---|---|
| 97 | A | 14 | mp 186–188° C.; IR $\nu_{max}$ (Nujol)/cm$^{-1}$ 3074, 3071, 1622, 1541, 1529, 1503, 1463, 1411, 1373, 1247, 1215, 1085, 1025, 932, 822, and 760; NMR $\delta_H$ (400 MHz, CDCl$_3$) 7.13 (1H, d, J 4.4Hz), 7.61(1H, d, J 5.9Hz), 8.30(1H, d, J 5.9Hz), and 8.40(1H, d, J 4.4 Hz); Anal. Calcd for C$_{12}$H$_6$ClN$_3$OS: C, 41.92; H, 1.28; N, 8.88. Found: C, 42.14; H, 1.35; N, 8.79. |
| 98 | F | 94 | IR $\nu_{max}$ (Nujol)/cm$^{-1}$ 3345, 1634, 1562, 1506, 1411, 1224 and 1078; NMR $\delta_H$ (400 MHz, CDCl$_3$) 1.87(1H, m), 2.00–2.16(2H, m), 2.23(1H, m), 3.79–4.02(4H, m), 4.45(4H, m), 7.23(1H, d, J 5.5Hz), 7.23(1H, dd, J 4.0, 5.0Hz), 7.82(1H, dd, J 1.5, 5.0Hz), 8.01(1H, d, J 5.5Hz) and 8.49(1H, dd, J 1.5, 4.0Hz); Retention time: 3.43 min (9:1). |
| 99 | F | 29 | IR $\nu_{max}$ (Nujol)/cm$^{-1}$ 3259, 1599, 1558, 1522, 1498, 1409, 1335, 1235, 1197, 1116 and 1050; NMR $\delta_H$ (400 MHz, CDCl$_3$) 1.91(2H, quintet, J 6.5Hz), 2.51(4H, m), 2.57(2H, t, J 6.6Hz), 3.71(2H, q, J 6.0Hz), 3.78(4H, t, J 4.5Hz), 6.24(1H, br s), 7.22(2H, m), 7.80(1H, dd, J 1.0, 5.0Hz), 8.00(1H, d, J 5.5Hz) and 8.51(1H, dd, J 1.0, 4.0Hz); Retention time: 2.84 min (9:1). |
| 100 | F | 64 | IR $\nu_{max}$ (Nujol)/cm$^{-1}$ 3292, 1634, 1576, 1523, 1502, 1408, 1315, 1242, 1198 and 1050; NMR $\delta_H$ (400 MHz, CDCl$_3$) 1.92(2H, quintet, J 6.1Hz), 3.75–3.82(4H, m), 5.54(1H, m), 7.22(1H, dd, J 4.0, 5.0Hz), 7.24(1H, d, J 5.5Hz), 7.81(1H, dd, J 1.5, 5.0Hz), 8.02(1H, d, J 5.5Hz) and 8.50(1H, dd, J 1.5, 4.0Hz); Retention time: 2.62 min (9:1). |
| 101 | F | 91 | IR $\nu_{max}$ (Nujol)/cm$^{-1}$ 3340, 1634, 1576, 1521, 1502, 1411, 1323, 1246, 1201, 1052 and 1041; NMR $\delta_H$ (400 MHz, CDCl$_3$) 1.38(3H, d, J 6.5Hz), 2.86(1H, br s), 3.76(1H, m), 3.88(1H, m), 4.43(1H, m), 5.32(1H, d, J 6.9Hz), 7.23(1H, dd, J 4.0, 5.0Hz), 7.23 (1H, d, J 5.5Hz), 7.82(1H, dd, J 1.5, 5.0Hz), 8.02(1H, d, J 5.5Hz) and 8.49(1H, dd, J 1.5, 4.0Hz); Retention time: 3.62 min (8:2). |
| 102 | F | 72 | IR $\nu_{max}$ (Nujol)/cm$^{-1}$ 3339, 1633, 1575, 1521, 1500, 1411, 1323, 1246, 1201, 1052 and 1041; NMR $\delta_H$ (400 MHz, CDCl$_3$) 1.38(3H, d, J 6.6Hz), 2.87(1H, br s), 3.75(1H, m), 3.89(1H, m), 4.43(1H, m), 5.33(1H, d, J 7.3Hz), 7.23(1H, d, J 5.5Hz), 7.23(1H, dd, J 4.0, 5.0Hz), 7.81(1H, dd, J 1.0, 5.0Hz), 8.02(1H, d, J 5.5Hz) and 8.49(1H, dd, J 1.0, 4.0Hz); Retention time: 3.63 min (8:2). |
| 103 | F | 76 | IR $\nu_{max}$ (Nujol)/cm$^{-1}$ 3400, 3235, 1633, 1573, 1527, 1501, 1408, 1356, 1234, 1199, 1129, 1080 and 1051; NMR $\delta_H$ (400 MHz, CDCl$_3$) 1.33(3H, d, J 7.0Hz), 2.99(1H, br s), 3.52(1H, ddd, J 5.5, 7.5, 14.0Hz), 3.80(1H, ddd, J 3.0, 6.5, 14.0Hz), 4.18(1H, m), 5.68(1H, t, J 6.0Hz), 7.23(1H, dd, J 4.0, 5.0Hz), 7.24(1H, d, J 5.5Hz), 7.81(1H, dd, J 1.0, 5.0Hz), 8.02(1H, d, J 5.5Hz) and 8.49(1H, dd, J 1.0, 4.0Hz); Retention time: 3.72 min (8:2). |
| 104 | F | 51 | IR $\nu_{max}$ (Nujol)/cm$^{-1}$ 3258, 3101, 1628, 1593, 1557, 1524, 1504, 1408, 1331, 1240, 1228, 1200, 1089 and 1046; NMR $\delta_H$ (400 MHz, CDCl$_3$) 2.25(2H, quintet, J 6.8Hz), 3.68(2H, q, J 6.7Hz), 4.14(2H, t, J 6.8Hz), 5.29(1H, t, J 6.0Hz), 6.98(1H, m), 7.09 (1H, m), 7.23(1H, dd, J 4.0, 5.0Hz), 7.25(1H, d, J 5.5Hz), 7.55(1H, s), 7.83(1H, dd, J 1.0, 5.0Hz), 8.04(1H, d, J 5.5Hz) and 8.49(1H, dd, J 1.0, 4.0Hz); Retention time: 3.69 min (8:2). |
| 105 | F | 3 | mp 210–212° C.; IR $\nu_{max}$ (Nujol)/cm$^{-1}$ 3241, 3084, 3046, 1654, 1596, 1571, 1521, 1459, 1365, 1353, 1201, 1060, 1042, 978, 804, 763, and 705; NMR $\delta_H$ (400 MHz, CDCl$_3$) 6.65(1H, m), 7.23(1H, m), 7.75(1H, m), 7.97(1H, d, J 3.5Hz) and 8.31(1H, d, J 3.5Hz); Anal. Calcd for C$_{13}$H$_{11}$N$_3$O$_2$S: C, 57.13; H, 4.06; N, 15.37. Found: C, 57.01; H, 4.02; N, 15.24. |
| 106 | F | 11 | mp 161–163° C.; IR $\nu_{max}$ (Nujol)/cm$^{-1}$ 3099, 1636, 1562, 1533, 1518, 1463, 1409, 1396, 1354, 1264, 1214, 1050, 1019, 882, 793, and 668; NMR $\delta_H$ (400 MHz, CDCl$_3$) 3.72 (2H, m), 3.85(2H, m), 5.64(1H, b m), 7.31(1H, d, J 5.6Hz), 7.49(1H, m), 8.00(1H, m), 8.56(1H, m), 8.83(1H, b s) and 9.60(1H, b s); Anal. Calcd for C$_{14}$H$_{12}$N$_4$O$_2$S: C, 55.99; H, 4.03; N, 18.65. Found: C, 56.00; H, 4.02; N, 18.80. |
| 107 | F | 32 | IR $\nu_{max}$ (Nujol)/cm$^{-1}$ 3258, 3106, 1634, 1592, 1555, 1516, 1407, 1356, 1317, 1252, 1160, 1129, 1047 and 1017; NMR $\delta_H$ (400 MHz, CDCl$_3$) 3.85(3H, s), 3.88(3H, s), 4.79 (2H, d, J 5.1Hz), 5.53(1H, t, J 6.0Hz), 6.85(1H, m), 6.99(2H, m), 7.19(1H, dd, J 4.0, 5.0Hz), 7.26(1H, d, J 5.5Hz), 7.77(1H, dd, J 1.0, 5.0Hz), 8.03(1H, d, J 5.5Hz) and 8.44(1H, dd, J 1.0, 4.0Hz); Retention time: 5.17 min (8:2). |
| 108 | F | 59 | IR $\nu_{max}$ (Nujol)/cm$^{-1}$ 3063, 1633, 1567, 1519, 1500, 1410, 1302, 1281, 1245, 1193, 1112 and 1014; NMR $\delta_H$ (400 MHz, CDCl$_3$) 3.38(6H, s), 3.72(4H, t, J 6.0Hz), 4.06(4H, t, J 6.0Hz), 7.23(1H, dd, J 4.0, 5.0Hz), 7.24(1H, d, J 5.5Hz), 7.80(1H, dd, J 1.0, 5.0Hz), 7.98(1H, d, J 5.5Hz) and 8.47(1H, dd, J 1.0, 4.0Hz); Retention time: 5.85 min (8:2). |
| 109 | F | 94 | mp 229.1–229.4° C.; IR $\nu_{max}$ (Nujol)/cm$^{-1}$ 3091, 3050, 2924, 2834, 1625, 1570, 1523, 1460, 1407 and 1376; NMR $\delta_H$ (400 MHz, DMSO) 2.03–2.09(4H, m), 3.60–3.81 (4H, m), 7.35–7.40(2H, m), 8.25(1H, d, J 5.0Hz), 8.43(1H, d, J 5.5Hz), and 8.49 (1H, dd, J 5.0, 1.1Hz). Anal. Calcd for C$_{15}$H$_{13}$N$_3$OS$_2$: C, 57.12; H, 4.15; N, 13.32. Found: C, 57.16; H, 4.11; N, 13.12. |
| 110 | R | 99 | IR $\nu_{max}$ (Nujol)/cm$^{-1}$ 3476, 3298, 3160, 1631, 1562, 1536, 1455, 1406, 1239, 1080 and 1050; NMR $\delta_H$ (400 MHz, CDCl$_3$) 5.19(2H, s), 7.24(1H, dd, J 4.0, 5.0Hz), 7.27(1H, d, J 5.5Hz), 7.82(1H, dd, J 1.0, 5.0Hz), 8.06(1H, d, J 5.5Hz) and 8.55(1H, dd, J 1.0, 4.0Hz); Retention time: 3.59 min (8:2). |
| 112 | F | 85 | IR $\nu_{max}$ (Nujol)/cm$^{-1}$ 3374, 1623, 1567, 1522, 1409, 1250, 1223, 1188, 1062 and 1050; NMR $\delta_H$ (400 MHz, DMSO) 2.00(1H, m), 2.11(1H, m), 3.55–3.90(4H, m), 4.47(1H, m), 5.06(1H, m), 7.35(1H, m), 7.36(1H, d, J 5.5Hz), 8.24(1H, br d, J 5.0Hz), 8.41 (1H, d, J 5.5Hz) and 8.46(1H, dd, J 1.0, 4.0Hz); Retention time: 4.48 min (8:2). |

TABLE 2-continued

| Example | Method | Yield (%) | Physical Data |
| --- | --- | --- | --- |
| 113 | F | 90 | IR $v_{max}$ (Nujol)/cm$^{-1}$ 3301, 1618, 1565, 1520, 1409, 1250, 1222, 1188, 1105 and 1049; NMR $\delta_H$ (400 MHz, DMSO) 1.99(1H, m), 2.10(1H, m), 3.66–3.81(4H, m), 4.47(1H, m), 5.06(1H, m), 7.35(1H, dd, J 4.0, 5.0Hz), 7.36(1H, d, J 5.5Hz), 8.23(1H, br d, J 5.0Hz), 8.41(1H, d, J 5.5Hz) and 8.46(1H, dd, J 1.0, 4.0Hz); Retention time: 4.50 min (8:2). |
| 114 | F | 56 | IR $v_{max}$ (Nujol)/cm$^{-1}$ 3554, 3287, 1626, 1585, 1526, 1501, 1410, 1311, 1243, 1200, 1074 and 1047; NMR $\delta_H$ (400 MHz, DMSO) 3.62(4H, m), 4.15(1H, br s), 4.71(2H, t, J 5.5 Hz), 7.04(1H, br s), 7.29(1H, d, J 5.5Hz), 7.35(1H, dd, J 4.0, 5.0Hz), 8.22(1H, dd, J 1.0, 5.0Hz), 8.39(1H, d, J 5.5Hz) and 8.74(1H, br s); Retention time: 2.84 min (8:2). |
| 115 | F | 10 | mp 155.9–156.3° C.; IR $v_{max}$ (Nujol)/cm$^{-1}$ 3104, 2925, 2854, 1733, 1565, 1513, 1463, 1408 and 1372; NMR $\delta_H$ (400 MHz, CDCl$_3$) 1.58(3H, s), 2.07–2.33(3H, m), 2.36–2.51(1H, m), 3.60–4.20(4H, m), 7.16–7.45(2H, m), 7.82(1H, d, J 3.9Hz), 8.01 (1H, s), and 8.50(1H, s). Anal. Calcd for C$_{17}$H$_{15}$N$_3$O$_3$S$_2$.0.5H$_2$O: C, 53.39; H, 4.22; N, 10.99. Found: C, 53.54; H, 4.08; N, 10.57 |
| 116 | A | 52 | IR $v_{max}$ (Nujol)/cm$^{-1}$ 3092, 2924, 2854, 1613, 1502, 1462, 1404, 1376 and 1253; NMR $\delta_H$ (400 MHz, CDCl$_3$) 2.78(3H, s), 7.08(1H, d, J 5.1Hz), 7.59(1H, d, J 6.1Hz), 7.76 (1H, d, 5.1Hz), and 8.31(1H, d, J 5.6Hz). |
| 117 | F | 80 | mp 165.1–165.7° C.; IR $v_{max}$ (Nujol)/cm$^{-1}$ 3066, 2924, 2854, 1626, 1569, 1508, 1462, 1399 and 1366; NMR $\delta_H$ (400 MHz, CDCl$_3$) 2.76(3H, s), 3.38(6H, s), 7.03(1H, d, J 4.5Hz), 7.24–7.27(1H, m), 7.64(1H, d, J 4.5Hz), and 7.96(1H, d, J 5.5Hz). Anal. Calcd for C$_{14}$H$_{13}$N$_3$OS$_2$.0.1H$_2$O: C, 55.09; H, 4.36; N, 13.77. Found: C, 54.97; H, 4.27; N, 13.59 |
| 118 | F | 42 | mp 194.5–195.0° C.; IR $v_{max}$ (Nujol)/cm$^{-1}$ 3337, 3265, 3117, 2924, 2854, 1592, 1462 and 1399; NMR $\delta_H$ (400 MHz, DMSO) 2.68(3H, s), 3.55–3.62(2H, m), 3.63–3.69(2H, m), 4.74(1H, t, J 5.1Hz), 7.21(1H, d, J 5.0Hz), 7.26–7.34(2H, m), 8.08(1H, d, J 5.1 Hz), and 8.41(1H, d, J 5.6Hz). Anal. Calcd for C$_{14}$H$_{13}$N$_3$O$_2$S$_2$: C, 52.65; H, 4.10; N, 13.15. Found: C, 52.40; H, 4.08; N, 13.01 |
| 119 | F | 22 | mp 126.4–127.1° C.; IR $v_{max}$ (Nujol)/cm$^{-1}$ 3537, 3499, 3438, 3082, 2955, 2854, 1613, 1568, 1533, 1506, 1409 and 1375; NMR $\delta_H$ (400 MHz, CDCl$_3$) 1.48(6H, s), 3.81(2H, d, J 2.9Hz), 5.40(1H, s), 5.80–5.90(1H, s), 7.20–7.29(2H, m), 7.82(1H, d, J 5.0 Hz), 8.03(1H, d, J 5.5Hz), 8.48(1H, d, J 4.0Hz). Anal. Calcd for C$_{15}$H$_{15}$N$_3$O$_2$S$_2$: C, 54.04; H, 4.53; N, 12.60. Found: C, 54.21; H, 4.65; N, 12.17 |
| 120 | F | 22 | mp 151.6–152.4° C.; NMR $\delta_H$ (400 MHz, DMSO) 3.16–3.25(2H, m), 3.39(3H, s), 4.01–4.12(2H, m), 7.36–7.42(2H, m), 8.02–8.14(2H, s), 8.25(1H, d, J 5.0Hz), 8.45–8.47(1H, m) and 8.49(1H, d, J 6.1Hz). Anal. Calcd for C$_{14}$H$_{14}$N$_4$OS$_2$.2HCl.1.5 H$_2$O: C, 40.19; H, 4.58; N, 13.39. Found: C, 39.78; H, 4.35; N, 13.39 |
| 121 | F | 37 | mp >131° C. dec; NMR $\delta_H$ (400 MHz, CDCl$_3$) 2.12–2.28(3H, m), 2.62–2.72(1H, m), 3.81–3.93(1H, m), 3.96–4.05(1H, m), 4.71–4.79(1H, m), 7.21(1H, t, J 4.5Hz), 7.30(1H, d, J 5.6Hz), 7.78–7.82(1H, m), 8.10(1H, d, J 5.5Hz), and 8.46–8.49(1H, m). Anal. Calcd for C$_{16}$H$_{13}$N$_3$O$_3$S$_2$.0.5H$_2$O: C, 52.16; H, 3.83; N, 11.41. Found: C, 52.27; H, 3.70; N, 11.51 |
| 122 | A | 50 | mp 185.7–186.2° C.; IR $v_{max}$ (Nujol)/cm$^{-1}$ 3074, 2924, 2854, 1739, 1623, 1461, 1409, 1376 and 1203; NMR $\delta_H$ (400 MHz, CDCl$_3$) 1.57(3H, t, J 7.1Hz), 4.66(2H, q, J 7.1 Hz), 7.30(1H, t, J 5.0Hz), 7.85(1H, d, J 5.4Hz), 7.89–7.92(1H, m), 8.34(1H, d, J 5.5Hz), and 8.88(1H, d, J 4.1Hz); Anal. Calcd for C$_{14}$H$_{10}$N$_2$O$_3$S$_2$: C, 52.82; H, 3.17; N, 8.79. Found: C, 52.53; H, 3.14; N, 8.70 |
| 123 | F | 46 | mp 144.6–145.2° C.; IR $v_{max}$ (Nujol)/cm$^{-1}$ 3380, 3266, 3113, 3076, 2925, 2855, 1739, 1596, 1564, 1365 and 1207; NMR $\delta_H$ (400 MHz, CDCl$_3$) 3.81(3H, s), 4.45(2H, d, J 5.7 Hz), 5.78(1H, t, J 5.6Hz), 7.22–7.29(1H, m), 7.83(1H, d, J 3.5Hz), 8.06(1H, d, J 5.6Hz) and 8.49–8.51(1H, m). Anal. Calcd for C$_{14}$H$_{11}$N$_3$O$_3$S$_2$: C, 50.44; H, 3.33; N, 12.60. Found: C, 50.44; H, 3.32; N, 12.55 |
| 124 | L | 50 | mp >250° C. dec; IR $v_{max}$ (Nujol)/cm$^{-1}$ 3084, 3078, 2924, 2854, 2730, 2647, 1723, 1621, 1459, 1410, 1377 and 1233; NMR $\delta_H$ (400 MHz, DMSO) 7.43(1H, t, J 4.5Hz), 7.91 (1H, d, J 5.5Hz), 8.32(1H, d, J 5.1Hz), 8.82(1H, d, J 5.6Hz), 8.87(1H, d, J 3.0Hz) and 13.70–13.90(1H, s). Anal. Calcd for C$_{12}$H$_{16}$N$_2$O$_3$S$_2$.0.75H$_2$O: C, 47.44; H, 2.49; N, 9.22. Found: C, 47.39; H, 2.73; N, 9.23 |
| 125 | F | 67 | mp 232.1–233.7° C.; IR $v_{max}$ (Nujol)/cm$^{-1}$ 3443, 3378, 3178, 2924, 2854, 1737, 1644, 1562, 1510, 1498, 1462, 1406, 1358 and 1321; NMR $\delta_H$ (400 MHz, DMSO) 3.98–4.09 (2H, m), 7.03–7.09(1H, s), 7.31–7.39(2H, m), 7.42–7.48(1H, s), 7.56–7.66(1H, m), 8.24(1H, d, J 4.4Hz), 8.44(1H, d, J 5.5Hz) and 8.55–8.75(1H, s). |
| 126 | M | 74 | mp 232.8–233.0° C.; IR $v_{max}$ (Nujol)/cm$^{-1}$ 3101, 3087, 3073, 2924, 2854, 1728, 1620, 1463, 1410, 1248 and 758; NMR $\delta_H$ (400 MHz, DMSO) 4.06(3H, s), 7.43(1H, t, J 4.5 Hz), 7.93(1H, d, J 5.5Hz), 8.32(1H, d, J 4.4Hz) and 8.79–8.86(2H, m). Anal. Calcd for C$_{13}$H$_8$N$_2$O$_3$S$_2$: C, 51.31; H, 2.65; N, 9.20. Found: C, 51.31; H, 2.65; N, 9.09 |
| 127 | L | 70 | mp 232.9–234.0° C.; IR $v_{max}$ (Nujol)/cm$^{-1}$ 3289, 2925, 2854, 2429, 1712, 1630, 1565, 1409 and 1371; NMR $\delta_H$ (400 MHz, DMSO) 3.96–4.38(2H, m), 7.28–7.44(2H, m), 7.68–7.93(1H, s), 8.25(1H, s, J 4.5Hz), 8.44(1H, d, J 5.0Hz), 8.57–8.82(1H, s) and 12.01–13.19(1H, s). Anal. Calcd for C$_{13}$H$_{19}$N$_3$O$_3$S$_2$.0.5H$_2$O: C, 47.55; H, 3.07; N, 12.80. Found: C, 47.46; H, 2.84; N, 12.87 |
| 128 | N | 65 | mp 242.1–242.7° C.; IR $v_{max}$ (Nujol)/cm$^{-1}$ 3262, 3202, 3102, 3018, 2955, 2924, 2854, 1622, 1574, 1547, 1409, 1362, 1340, 1234 and 1160; NMR $\delta_H$ (400 MHz, DMSO) 3.06 (3H, m), 7.38(1H, t, J 4.2Hz), 7.47(1H, d, J 5.5Hz), 8.28(1H, d, J 3.5Hz), 8.54(1H, d, J 5.5Hz), 9.47(1H, s) and 9.74(1H, s); Anal. Calcd for C$_{12}$H$_{10}$N$_4$O$_3$S$_3$: C, 40.67; H, 2.84; N, 15.80. Found: C, 40.99; H, 2.92; N, 15.53 |
| 129 | F | 99 | mp 96.2–96.9° C.; IR $v_{max}$ (Nujol)/cm$^{-1}$ 3339, 3080, 3061, 2924, 2854, 1630, 1561, 1503, 1458, 1401, 1371, 1079 and 773; NMR $\delta_H$ (400 MHz, CDCl$_3$) 1.81–1.92(1H, m), 1.97–2.30(3H, m), 2.79(3H, s), 3.78–3.95(3H, m), 3.98–4.08(1H, m), 4.42– |

TABLE 2-continued

| Example | Method | Yield (%) | Physical Data |
|---|---|---|---|
| | | | 4.53(1H, s), 7.07(1H, d, J 5.0Hz), 7.25(1H, d, J 5.6Hz), 7.68(1H, d, J 5.0Hz) and 8.03(1H, d, J 5.5Hz); Anal. Calcd for $C_{17}H_{17}N_3O_2S_2$: C, 55.96; H, 4.86; N, 11.52. Found: C, 55.92; H, 4.78; N, 11.14 |
| 130 | O | 44 | mp 258.3–259.0° C.; IR $v_{max}$ (Nujol)/cm$^{-1}$ 3276, 2928, 2854, 1667, 1629, 1584, 1556, 1463, 1407 and 1365; NMR $\delta_H$ (400 MHz, DMSO) 2.02(3H, s), 7.38(1H, t, J 4.5Hz), 7.42(1H, d, J 5.5Hz), 8.28(1H, d, J 3.6Hz), 8.51(1H, d, J 5.5Hz), 8.67–8.72(1H, s), 9.30(1H, s) and 10.02(1H, s); Anal. Calcd for $C_{13}H_{10}N_4O_2S_2 \cdot 0.5H_2O$: C, 47.69; H, 3.39; N, 17.11. Found: C, 47.52; H, 3.04; N, 16.87 |
| 131 | P | 68 | mp 252.8–253.3° C.; IR $v_{max}$ (Nujol)/cm$^{-1}$ 3308, 3243, 3073, 2924, 2854, 1642, 1586, 1557, 1463, 1407, 1364, 1326 and 762; NMR $\delta_H$ (400 MHz, DMSO) 3.69(2H, t, J 5.5 Hz), 4.98(1H, d, J 10.4Hz), 5.14(1H, d, J 17.1Hz), 5.74–5.86(1H, m), 6.67–6.82 (1H, s), 7.35(1H, t, J 4.2Hz), 7.43(1H, d, J 5.6Hz), 8.09(1H, s), 8.25(1H, d, J 4.5 Hz), 8.51(1H, d, J 5.5Hz), 8.79(1H, s) and 9.17(1H, s); Anal. Calcd for $C_{15}H_{13}N_5O_2S_2 \cdot 0.25H_2O$: C, 49.50; H, 3.74; N, 19.24. Found: C, 49.38; H, 3.64; N, 19.11 |
| 132 | F | 44 | mp 138.1–138.7° C.; IR $v_{max}$ (Nujol)/cm$^{-1}$ 3258, 3108, 3047, 2926, 2855, 1593, 1553, 1519, 1505, 1463, 1391, 1372, 1229 and 776; NMR $\delta_H$ (400 MHz, CDCl$_3$) 2.24(2H, quin, J 6.9Hz), 2.76(3H, s), 3.69(2H, q, J 6.5Hz), 4.13(2H, t, J 7.1Hz), 5.27–5.29 (1H, m), 6.96(1H, s), 7.04(1H, d, J 5.0Hz), 7.08(1H, d, J 5.5Hz), 7.24(1H, t, J 5.6Hz), 7.53 (1H, s), 7.67(1H, d, J 5.1Hz) and 8.04(1H, d, J 5.5Hz); Anal. Calcd for $C_{18}H_{17}N_5OS_2 \cdot 0.3H_2O$: C, 55.59; H, 4.56; N, 18.01. Found: C, 55.56; H, 4.40; N, 17.85 |
| 133 | F | 26 | IR $v_{max}$ (Nujol)/cm$^{-1}$ 3400, 3232, 1633, 1573, 1528, 1501, 1408, 1356, 1234, 1199, 1129, 1080 and 1051; NMR $\delta_H$ (400 MHz, CDCl$_3$) 1.33(3H, d, J 6.5Hz), 2.95(1H, br s), 3.53(1H, ddd, J 5.5, 7.5, 14.0Hz), 3.81(1H, ddd, J 3.0, 6.5, 14.0Hz), 4.18(1H, m), 5.67(1H, t, J 6.0Hz), 7.23(1H, dd, J 4.0, 5.0Hz), 7.25(1H, d, J 5.5Hz), 7.81(1H, dd, J 1.0, 5.0Hz), 8.03(1H, d, J 5.5Hz) and 8.50(1H, dd, J 1.0, 4.0Hz); Retention time: 3.74 min (8:2). |
| 134 | Q | 65 | mp 143.6–144.7° C.; IR $v_{max}$ (Nujol)/cm$^{-1}$ 3319, 3107, 3098, 3061, 2924, 2854, 2764, 1663, 1624, 1353, 1460, 1400, 1376 and 764; NMR $\delta_H$ (400 MHz, CDCl$_3$) 2.28(6H, s), 2.55(2H, t, J 6.5Hz), 3.55(2H, q, J 6.2Hz), 7.44(1H, t, J 4.3Hz), 7.90(1H, d, J 5.5 Hz), 8.33(1H, d, J 5.1Hz) and 8.76–8.84(3H, m); Anal. Calcd for $C_{16}H_{16}N_4O_2S_2 \cdot 0.55 H_2O$: C, 51.89; H, 4.65; N, 15.13. Found: C, 51.54; H, 4.27; N, 15.02 |
| 135 | F | 14 | Byproduct from the preparation of Example 143. IR $v_{max}$ (Nujol)/cm$^{-1}$ 3145, 3088, 1725, 1620, 1546, 1509, 1435, 1410, 1339, 1234 and 1064; NMR $\delta_H$ (400 MHz, CDCl$_3$) 2.26(2H, quintet, J 7.5Hz), 2.79(2H, t, J 8.0Hz), 4.32(2H, t, J 7.0Hz), 7.32(1H, dd, J 4.0, 5.0Hz), 7.57(1H, d, J 5.5Hz), 7.85(1H, dd, J 1.0, 5.0Hz), 8.21(1H, d, J 5.5Hz) and 9.23(1H, dd, J 1.0, 4.0Hz); Retention time: 3.58 min (8:2). |
| 136 | Q | 71 | mp 173.1–174.0° C.; IR $v_{max}$ (Nujol)/cm$^{-1}$ 3082, 2924, 2854, 1654, 1630, 1541, 1500, 1459, 1406, 1374, 1137 and 756; NMR $\delta_H$ (400 MHz, DMSO) 2.96(3H, s), 3.15(3H, s), 7.40(1H, t, J 4.2Hz), 7.82(1H, d, J 5.6Hz), 8.28(1H, d, J 5.0Hz), 8.58–8.61(1H, m) and 8.80(1H, d, J 5.5Hz); Anal. Calcd for $C_{14}H_{11}N_3O_2S_2$: C, 52.98; H, 3.49; N, 13.23. Found: C, 53.02; H, 3.44; N, 13.23 |
| 137 | S | 60 | IR $v_{max}$ (Nujol)/cm$^{-1}$ 3106, 1717, 1625, 1528, 1503, 1409, 1340, 1273, 1232 and 1045; NMR $\delta_H$ (400 MHz, CDCl$_3$) 2.40(6H, s), 7.26(1H, m), 7.67(1H, d, J 5.5Hz), 7.86 (1H, dd, J 1.0, 5.0Hz), 8.34(1H, d, J 5.5Hz) and 8.57(1H, dd, J 1.0, 4.0Hz); Retention time: 2.70 min (8:2). |
| 138 | T | 58 | IR $v_{max}$ (Nujol)/cm$^{-1}$ 3195, 3121, 1678, 1622, 1539, 1499, 1411, 1342, 1254, 1227, 1211, 1062 and 1021; NMR $\delta_H$ (400 MHz, CDCl$_3$) 2.57(3H, s), 7.29(1H, dd, J 4.0, 5.0 Hz), 7.49(1H, d, J 5.5Hz), 7.86(1H, dd, J 1.0, 5.0Hz), 8.22(1H, d, J 5.5Hz), 8.24 (1H, br s) and 8.89(1H, br s); Retention time: 3.22 min (8:2). |
| 139 | F | 18 | IR $v_{max}$ (Nujol)/cm$^{-1}$ 3424, 3091, 1629, 1555, 1502, 1409, 1326, 1238, 1101, 1055 and 1003; NMR $\delta_H$ (400 MHz, CDCl$_3$) 7.28(1H, m), 7.31(1H, dd, J 4.0, 5.0Hz), 7.61, (1H, d, J 5.5Hz), 7.93(1H, dd, J 1.5, 5.0Hz), 8.14(1H, t, J 1.5Hz), 8.33(1H, d, J 5.5Hz), 8.53(1H, dd, J 1.5, 4.0Hz) and 8.88(1H, m); Retention time: 5.52 min (8:2). |
| 140 | F | 76 | IR $v_{max}$ (Nujol)/cm$^{-1}$ 3252, 3072, 1595, 1557, 1524, 1497, 1405, 1305, 1279, 1240, 1197, 1087 and 1046; NMR $\delta_H$ (400 MHz, CDCl$_3$) 2.22(2H, quintet, J 6.8Hz), 3.65 (1H, q, J 6.5Hz), 4.08(2H, t, J 6.8Hz), 5.21(1H, t, J 6.0Hz), 6.18(2H, t, J 2.0Hz), 6.71(2H, t, J 2.0Hz), 7.23(1H, m), 7.24(1H, d, J 5.5Hz), 7.81(1H, dd, J 1.0, 5.0Hz), 8.02(1H, d, J 5.5Hz) and 8.47(1H, dd, J 1.0, 4.0Hz); Retention time: 7.36 min (8:2). |
| 141 | F | 88 | IR $v_{max}$ (Nujol)/cm$^{-1}$ 3096, 1628, 1617, 1518, 1409, 1359, 1255, 1226, 1212, 1174 and 1050; NMR $\delta_H$ (400 MHz, CDCl$_3$) 4.12(3H, s), 7.21(1H, dd, J 4.0, 5.0Hz), 7.49(1H, d, J 5.5Hz), 7.82(1H, dd, J 1.0, 5.0Hz), 8.14(1H, dd, J 1.0, 4.0Hz) and 8.29(1H, d, J 5.5Hz); m/z 361 MH$^+$; Retention time: 3.10 min (8:2). |
| 142 | F | 15 | IR $v_{max}$ (Nujol)/cm$^{-1}$ 3257, 3120, 1630, 1559, 1497, 1408, 1237, 1089 and 1046; NMR $\delta_H$ (400 MHz, CDCl$_3$) 2.98(2H, t, J 7.0Hz), 3.57(3H, s), 3.91(2H, q, J 6.8Hz), 5.46 (1H, t, J 6.0Hz), 6.05(1H, m), 6.10(1H, t, J 3.0Hz), 6.59(1H, t, J 2.5Hz), 7.21(1H, dd, J 4.0, 5.0Hz), 7.24(1H, d, J 5.5Hz), 7.79(1H, dd, J 1.0, 5.0Hz), 8.02(1H, d, J 5.5 Hz) and 8.49(1H, dd, J 1.0, 4.0Hz); Retention time: 7.51 min (8:2). |
| 143 | F | 13 | IR $v_{max}$ (Nujol)/cm$^{-1}$ 3298, 1694, 1633, 1567, 1503 and 1082; NMR $\delta_H$ (400 MHz, DMSO) 1.88(2H, t, J 7.0Hz), 2.36(2H, t, J 7.0Hz), 3.48(2H, m), 7.30(1H, m), 7.35 (1H, br d, J 4.0Hz), 7.62(1H, m), 8.23(1H, br d, J 5.0Hz), 8.39(1H, br d, J 5.5Hz) and 8.57(1H, br s); Retention time: 5.31 min (8:2). |
| 144 | F | 52 | IR $v_{max}$ (Nujol)/cm$^{-1}$ 3230, 3093, 1635, 1563, 1523, 1504, 1408, 1229, 1080 and 1046; NMR $\delta_H$ (400 MHz, CDCl$_3$) 1.43(1H, br s), 3.06(2H, t, J 6.5Hz), 3.96(2H, q, J 6.2 Hz), 5.70(1H, m), 6.90(1H, s), 7.23(1H, dd, J 4.0, 5.0Hz), 7.26(1H, m), 7.81(1H, dd, J 1.0, 5.0Hz), 8.01(1H, d, J 5.5Hz) and 8.50(1H, dd, J 1.0, 4.0Hz); Retention time: 3.87 min (8:2), detection wavelength λ 210 nm. |

TABLE 2-continued

| Example | Method | Yield (%) | Physical Data |
| --- | --- | --- | --- |
| 145 | F | 71 | IR $v_{max}$ (Nujol)/cm$^{-1}$ 3102, 1629, 1597, 1536, 1516, 1500, 1407, 1260, 1215, 1169 and 1051; NMR $\delta_H$ (400 MHz, DMSO) 6.79(2H, m), 7.27(1H, dd, J 4.0, 5.0Hz), 7.40(2H, m), 7.63(1H, d, J 5.5Hz), 8.08(1H, dd, J 1.5, 4.0Hz), 8.19(1H, dd, J 1.5, 5.0Hz), 8.74(1H, d, J 5.5Hz) and 10.11(1H, s); m/z 437 MH$^+$; Retention time: 4.29 min (8:2). |
| 146 | F | 27 | NMR $\delta_H$ (400 MHz, CDCl$_3$) 2.41(3H, br s), 4.05(2H, m), 4.69(2H, t, J 6.1Hz), 5.48 (1H, t, J 6.0Hz), 7.24(1H, m), 7.25(1H, d, J 5.5Hz), 7.83(1H, dd, J 1.5, 5.0Hz), 7.94 (1H, s), 8.08(1H, dd, J 1.5, 4.0Hz) and 8.46(1H, dd, J 1.5, 4.0Hz); Retention time: 3.55 min (8:2). |
| 147 | F | 39 | IR $v_{max}$ (Nujol)/cm$^{-1}$ 3098, 3057, 1632, 1535, 1510, 1411, 1264, 1203, 1167 and 1050; NMR $\delta_H$ (400 MHz, DMSO) 3.64(3H, s), 7.26(1H, dd, J 4.0, 5.0Hz), 7.65(1H, d, J 5.5Hz), 8.01(1H, dd, J 1.5, 4.0Hz), 8.17(1H, dd, J 1.5, 5.0Hz), 8.73(1H, d, J 5.5Hz) and 8.96(1H, s); Retention time: 2.59 min (8:2). |
| 148 | F | 52 | IR $v_{max}$ (Nujol)/cm$^{-1}$ 3070, 1635, 1536, 1521, 1408, 1223, 1200, 1098 and 1050; NMR $\delta_H$ (400 MHz, DMSO) 2.84(3H, s), 7.30(1H, t, J 4.5Hz), 7.70(1H, d, J 5.5Hz), 8.24 (2H, m) and 8.77(1H, d, J 5.5Hz); m/z 377 MH$^+$; Retention time: 5.48 min (8:2). |
| 149 | F | 38 | IR $v_{max}$ (Nujol)/cm$^{-1}$ 3109, 3072, 2446, 2389, 1625, 1529, 1516, 1412, 1300, 1255, 1213, 1170 and 1076; NMR $\delta_H$ (400 MHz, DMSO) 3.85(3H, s), 7.31(1H, dd, J 4.0, 5.0 Hz), 7.67(1H, d, J 5.5Hz), 7.91(1H, d, J 1.5Hz), 8.07(1H, d, J 1.5Hz), 8.09(1H, dd, J 1.5, 4.0Hz), 8.20(1H, dd, J 1.5, 5.0Hz) and 8.78(1H, d, J 5.5Hz); Retention time: 2.97 min (8:2). |
| 150 | U | 55 | NMR $\delta_H$ (400 MHz, DMSO) 0.85(6H, d, J 6.5Hz), 1.96(3H, m), 3.37(2H, q, J 6.0 Hz), 3.54(2H, m), 7.29(1H, d, J 5.5Hz), 7.35(1H, dd, J 4.0, 5.0Hz), 7.47(1H, m), 7.90(1H, m), 8.20(1H, br d, J 4.0Hz), 8.39(1H, d, J 5.5Hz) and 8.59(1H, br s); Retention time: 3.92 min (8:2). |
| 151 | U | 50 | NMR $\delta_H$ (400 MHz, DMSO) 1.11–1.35(5H, m), 1.58–1.69(5H, m), 2.08(1H, m), 3.35(2H, q, J 6.0Hz), 3.53(2H, m), 7.30(1H, d, J 5.5Hz), 7.36(1H, dd, J 4.0, 5.0Hz), 7.48(1H, m), 7.78(1H, m), 8.21(1H, br d, J 4.5Hz), 8.39(1H, d, J 5.5Hz) and 8.59 (1H, br s); Retention time: 4.81 min (8:2). |
| 152 | U | 63 | NMR $\delta_H$ (400 MHz, DMSO) 3.60(2H, q, J 6.0Hz), 3.67(2H, m), 7.29(1H, d, J 5.5 Hz), 7.34(1H, dd, J 4.0, 5.0Hz), 7.44(2H, m), 7.51(1H, m), 7.63(1H, m), 7.85(2H, m), 8.20(1H, dd, J 1.0, 5.0Hz), 8.39(1H, d, J 5.5Hz) and 8.58(2H, m); Retention time: 4.45 min (8:2). |
| 153 | U | 63 | NMR $\delta_H$ (400 MHz, DMSO) 3.59(2H, q, J 6.0Hz), 3.68(2H, m), 7.29(1H, d, J 5.5 Hz), 7.35(1H, dd, J 4.0, 5.0Hz), 7.52(2H, m), 7.58(1H, m), 7.87(2H, m), 8.20(1H, dd, J 1.0, 5.0Hz), 8.39(1H, d, J 5.5Hz) and 8.66(2H, m); Retention time: 6.24 min (8:2). |
| 154 | U | 44 | NMR $\delta_H$ (400 MHz, DMSO) 3.56(2H, q, J 6.0Hz), 3.66(2H, m), 7.14(1H, dd, J 4.0, 5.0Hz), 7.30(1H, d, J 5.5Hz), 7.35(1H, dd, J 4.0, 5.0Hz), 7.64(1H, m), 7.74(2H, m), 8.21(1H, dd, J 1.0, 5.0Hz), 8.40(1H, d, J 5.5Hz) and 8.60(2H, m); Retention time: 4.30 min (8:2). |
| 155 | U | 55 | NMR $\delta_H$ (400 MHz, DMSO) 3.30(2H, m), 3.50(5H, m), 7.23(1H, m), 7.29(1H, d, J 5.5Hz), 7.35(1H, dd, J 4.0, 5.0Hz), 7.56(1H, m), 8.20(1H, br d, J 5.0Hz), 8.38(1H, d, J 5.5Hz) and 8.59(1H, br s); Retention time: 3.45 min (8:2). |
| 156 | U | 57 | NMR $\delta_H$ (400 MHz, DMSO) 0.85(6H, d, J 6.7Hz), 1.82(1H, m), 3.29(2H, m), 3.55 (2H, m), 3.71(2H, d, J 6.4Hz), 7.20(1H, m), 7.29(1H, d, J 5.5Hz), 7.35(1H, dd, J 4.0, 5.0Hz), 7.50(1H, m), 8.20(1H, br d, J 5.0Hz), 8.39(1H, d, J 5.5Hz) and 8.59 (1H, br s); Retention time: 4.80 min (8:2). |
| 157 | U | 49 | NMR $\delta_H$ (400 MHz, DMSO) 3.34(2H, m), 3.57(2H, m), 5.02(2H, s), 7.30–7.36(8H, m), 7.52(1H, m), 8.20(1H, br d, J 5.0Hz), 8.39(1H, d, J 5.5Hz) and 8.60(1H, br s); Retention time: 5.01 min (8:2). |
| 158 | U | 41 | NMR $\delta_H$ (400 MHz, DMSO) 3.32(2H, q, J 6.0Hz), 3.56(2H, m), 3.76(2H, t, J 5.2 Hz), 4.20(2H, t, J 5.2Hz), 7.30(1H, d, J 5.5Hz), 7.36(1H, dd, J 4.0, 5.0Hz), 7.43 (1H, m), 7.52(1H, m), 8.21(1H, dd, J 1.0, 5.0Hz), 8.39(1H, d, J 5.5Hz) and 8.59(1H, br s); Retention time: 3.90 min (8:2). |
| 159 | V | 86 | NMR $\delta_H$ (400 MHz, DMSO) 3.33(2H, q, J 6.0Hz), 3.52(2H, m), 3.63(2H, t, J 5.5 Hz), 4.99(1H, dd, J 2.0, 10.2Hz), 5.09(1H, dd, J 2.0, 17.0Hz), 5.79(1H, m), 6.06 (2H, t, J 5.5Hz), 7.30(1H, d, J 5.5Hz), 7.36(1H, dd, J 4.0, 5.0Hz), 7.53(1H, m), 8.21 (1H, br d, J 5.0Hz), 8.39(1H, d, J 5.5Hz) and 8.60(1H, br s); Retention time: 3.41 min (8:2). |
| 160 | V | 84 | NMR $\delta_H$ (400 MHz, DMSO) 1.03–1.25(5H, m), 1.49(1H, m), 1.61(2H, m), 1.71(2H, m), 3.32(3H, m), 3.50(2H, m), 5.79(1H, d, J 7.9Hz), 5.88(1H, t, J 5.7Hz), 7.30(1H, d, J 5.5Hz), 7.35(1H, dd, J 4.0, 5.0Hz), 7.53(1H, m), 8.21(1H, br d, J 5.0Hz), 8.39 (1H, d, J 5.5Hz) and 8.59(1H, br s); Retention time: 4.76 min (8:2). |
| 161 | V | 89 | NMR $\delta_H$ (400 MHz, DMSO) 3.35(2H, q, J 6.1Hz), 3.53(2H, m), 4.20(2H, d, J 5.9 Hz), 6.10(1H, t, J 5.7Hz), 6.42(1H, t, J 6.0Hz), 7.17–7.30(6H, m), 7.34(1H, dd, J 4.0, 5.0Hz), 7.53(1H, m), 8.19(1H, br d, J 5.0Hz), 8.39(1H, d, J 5.5Hz) and 8.59 (1H, br s); Retention time: 4.25 min (8:2). |
| 162 | V | 99 | NMR $\delta_H$ (400 MHz, DMSO) 3.43(2H, q, J 5.9Hz), 3.59(2H, m), 6.30(1H, t, J 5.7 Hz), 6.99(1H, m), 7.19–7.46(6H, m), 7.60(1H, m), 8.20(1H, br d, J 5.0Hz), 8.39 (1H, d, J 5.5Hz), 8.50(1H, s) and 8.62(1H, br s); Retention time: 5.12 min (8:2). |
| 163 | V | 96 | NMR $\delta_H$ (400 MHz, DMSO) 3.42(2H, q, J 5.8Hz), 3.59(2H, m), 6.34(1H, t, J 5.7 Hz), 7.23–7.40(6H, m), 7.59(1H, m), 8.20(1H, br d, J 5.0Hz), 8.39(1H, d, J 5.5Hz), 8.58(1H, br s) and 8.66(1H, s); Retention time: 7.72 min (8:2). |
| 164 | W | 61 | NMR $\delta_H$ (400 MHz, DMSO) 3.70(2H, m), 3.83(2H, m), 7.08(1H, t, J 7.2Hz), 7.24–7.37(6H, m), 7.69(1H, br s), 7.85(1H, br s), 8.23(1H, br d, J 5.0Hz), 8.40(1H, d, J 5.5Hz), 8.62(1H, br s) and 9.62(1H, br s); Retention time: 4.47 min (8:2). |

TABLE 2-continued

| Example | Method | Yield (%) | Physical Data |
|---|---|---|---|
| 165 | W | 19 | NMR $\delta_H$ (400 MHz, DMSO) 3.71(2H, m), 3.82(2H, m), 7.26–7.43(6H, m), 7.63(1H, m), 7.93(1H, m), 8.22(1H, br d, J 5.0Hz), 8.40(1H, d, J 5.5Hz), 8.59(1H, br s) and 9.63(1H, br s); Retention time: 6.82 min (8:2). |
| 166 | W | 41 | NMR $\delta_H$ (400 MHz, DMSO) 1.09–1.22(5H, m), 1.52(1H, m), 1.62(2H, m), 1.80(2H, m), 3.63(2H, m), 3.71(2H, m), 3.94(1H, m), 7.27–7.38(4H, m), 7.59(1H, m), 8.21 (1H, br d, J 5.0Hz), 8.40(1H, d, J 5.5Hz) and 8.63(1H, br s); Retention time: 5.98 min (8:2). |
| 167 | U | 16 | m/z 383 MH$^+$; Retention time: 2.96 min (8:2). |
| 168 | U | 23 | NMR $\delta_H$ (400 MHz, CDCl$_3$) 0.88(3H, t, J 7.2Hz), 1.40(2H, sextet, J 7.6Hz), 1.75 (2H, m), 3.02(2H, m), 3.49(2H, q, J 5.9Hz), 3.84(2H, q, J 5.7Hz), 5.02(1H, br s), 5.61(1H, t, J 6.0Hz), 7.23(1H, dd, J 4.0, 5.0Hz), 7.25(1H, d, J 5.5Hz), 7.82(1H, d, J 1.0, 5.0Hz), 8.04(1H, d, J 5.5Hz) and 8.48(1H, dd, J 1.0, 4.0Hz); Retention time: 3.91 min (8:2). |
| 169 | X | 11 | Mp 151° C.; NMR $\delta_H$ (400 MHz, DMSO) 2.92(3H, s), 2.93(3H, s), 4.46(2H, br s), 7.39(1H, dd, J 4.0, 5.0Hz), 7.63(1H, d, J 5.5Hz), 8.28(1H, dd, J 1.0, 5.0Hz), 8.71 (1H, d, J 5.5Hz), 9.31(1H, br d, J 3.0Hz), 10.05(1H, br s) and 11.73(1H, s); Retention time: 3.37 min (8:2). |
| 170 | Y | 31 | IR $\nu_{max}$ (Nujol)/cm$^{-1}$ 3323, 1637, 1616, 1597, 1570, 1525, 1505, 1407, 1353, 1332, 1245, 1199, 1080 and 1051; NMR $\delta_H$ (400 MHz, DMSO) 3.33(4H, q, J 6.0Hz), 3.51(4H, m), 6.15(2H, t, J 5.9Hz), 7.27(2H, d, J 5.5Hz), 7.31(2H, dd, J 4.0, 5.0Hz), 7.52(2H, m), 8.17 (2H, dd, J 1.0, 5.0Hz), 8.37(2H, d, J 5.5Hz) and 8.57(2H, br s); m/z 635 MH$^+$. |

Adenosine Receptor Binding

Binding Affinities at hA$_{2A}$ Receptors

The compounds were examined in an assay measuring in vitro binding to human adenosine A$_{2A}$ receptors expressed in HEK-293 cells by determining the displacement of the adenosine A$_{2A}$ receptor selective radioligand [$^3$H]-CGS 21680 using standard techniques. The results are summarised in Table 3.

TABLE 3

| Example | K$_i$ (nM) |
|---|---|
| 1 | 104 |
| 2 | 10 |
| 3 | 74 |
| 4 | 40 |
| 5 | 30 |
| 6 | 108 |
| 8 | 586 |
| 11 | 330 |
| 12 | 31 |
| 13 | 153 |
| 14 | 329 |
| 17 | 895 |
| 18 | 346 |
| 25 | 435 |
| 28 | 865 |
| 29 | 539 |
| 34 | 245 |
| 35 | 19 |
| 37 | 361 |
| 39 | 575 |
| 40 | 295 |
| 42 | 26 |
| 43 | 22 |
| 44 | 91 |
| 45 | 26 |
| 46 | 101 |
| 47 | 46 |
| 48 | 151 |
| 49 | 18 |
| 50 | 33 |
| 51 | 8 |
| 52 | 32 |
| 54 | 36 |
| 55 | 78 |
| 56 | 309 |
| 57 | 800 |
| 58 | 15 |

TABLE 3-continued

| Example | K$_i$ (nM) |
|---|---|
| 59 | 18 |
| 60 | 237 |
| 61 | 21 |
| 63 | 37 |
| 64 | 529 |
| 65 | 21 |
| 66 | 218 |
| 67 | 469 |
| 68 | 105 |
| 72 | 126 |
| 73 | 48 |
| 74 | 90 |
| 76 | 8 |
| 77 | 97 |
| 78 | 46 |
| 79 | 858 |
| 81 | 63 |
| 82 | 29 |
| 83 | 863 |
| 84 | 392 |
| 89 | 3 |
| 93 | 7 |
| 95 | 8 |
| 100 | 4 |
| 101 | 7 |
| 102 | 2 |
| 103 | 6 |
| 104 | 2 |
| 118 | 7 |
| 144 | 5 |
| 150 | 4 |
| 151 | 7 |
| 155 | 4 |
| 158 | 6 |
| 159 | 8 |

Evaluation of Potential Anti-Parkinsonian Activity In Vivo

Haloperidol-induced Hypolocomotion Model

It has previously been demonstrated that adenosine antagonists, such as theophylline, can reverse the behavioural depressant effects of dopamine antagonists, such as haloperidol, in rodents (Mandhane S. N. et al., Adenosine A$_2$ receptors modulate haloperidol-induced catalepsy in rats. *Eur. J. Pharmacol.* 1997, 328, 135–141). This approach is also considered a valid method for screening drugs with potential antiparkinsonian effects. Thus, the ability of novel adenosine antagonists to block haloperidol-induced deficits in locomotor activity in mice can be used to assess both in vivo and potential antiparkinsonian efficacy.

Method

Female TO mice (25–30 g) obtained from TUCK, UK, are used for all experiments. Animals are housed in groups of 8 [cage size—40 (width)×40 (length)×20 (height)cm] under 12 hr light/dark cycle (lights on 08:00 hr), in a temperature (20±2° C.) and humidity (55±15%) controlled environment. Animals have free access to food and water, and are allowed at least 7 days to acclimatize after delivery before experimental use.

Drugs

Liquid injectable haloperidol (1 ml Serenance ampoules from Baker Norton, Harlow, Essex, each containing haloperidol BP 5 mg, batch # P424) are diluted to a final concentration of 0.02 mg/ml using saline. Test compounds are typically prepared as aqueous suspensions in 8% Tween. All compounds are administered intraperitoneally in a volume of 10 ml/kg.

Procedure 1.5 hours before testing, mice are administered 0.2 mg/kg haloperidol, a dose that reduces baseline locomotor activity by at least 50%. Test substances are typically administered 5–60 minutes prior to testing. The animals are then placed individually into clean, clear polycarbonate cages [20 (width)×40 (length)×20 (height) cm, with a flat perforated, Perspex lid]. Horizontal locomotor activity is determined by placing the cages within a frame containing a 3×6 array of photocells linked to a computer, which tabulates beam breaks. Mice are left undisturbed to explore for 1 hour, and the number of beams breaks made during this period serves as a record of locomotor activity which is compared with data for control animals for statistically significant differences. In this model, Example 86, administered intraperitoneally at a dose of 10 mg/kg, significantly reversed haloperidol-induced hypolocomotion.

6-OHDA Model

Parkinson's disease is a progressive neurodegenerative disorder characterised by symptoms of muscle rigidity, tremor, paucity of movement (hypokinesia), and postural instability. It has been established for some time that the primary deficit in PD is a loss of dopaminergic neurones in the substantia nigra which project to the striatum, and indeed a substantial proportion of striatal dopamine is lost (ca 80–85%) before symptoms are observed. The loss of striatal dopamine results in abnormal activity of the basal ganglia, a series of nuclei which regulate smooth and well coordinated movement (Blandini F. et al., Glutamate and Parkinson's Disease. *Mol. Neurobiol.* 1996, 12, 73–94). The neurochemical deficits seen in Parkinson's disease can be reproduced by local injection of the dopaminergic neurotoxin 6-hydroxydopamine into brain regions containing either the cell bodies or axonal fibres of the nigrostriatal neurones.

By unilaterally lesioning the nigrostriatal pathway on only one-side of the brain, a behavioural asymmetry in movement inhibition is observed. Although unilaterally-lesioned animals are still mobile and capable of self maintenance, the remaining dopamine-sensitive neurones on the lesioned side become supersenstive to stimulation. This is demonstrated by the observation that following systemic administration of dopamine agonists, such as apomorphine, animals show a pronounced rotation in a direction contralateral to the side of lesioning. The ability of compounds to induce contralateral rotations in 6-OHDA lesioned rats has proven to be a sensitive model to predict drug efficacy in the treatment of Parkinson's Disease.

Animals

Male Sprague-Dawley rats, obtained from Charles River, are used for all experiments. Animals are housed in groups of 5 under 12 hr light/dark cycle (lights on 08:00 hr), in a temperature (20±2° C.) and humidity (55±15%) controlled environment. Animals have free access to food and water, and are allowed at least 7 days to acclimatize after delivery before experimental use.

Drugs

Ascorbic acid, desipramine, 6-OHDA and apomorphine (Sigma-Aldrich, Poole, UK). 6-OHDA is freshly prepared as a solution in 0.2% ascorbate at a concentration of 4 mg/mL prior to surgery. Desipramine is dissolved in warm saline, and administered in a volume of 1 ml/kg. Apomorphine is dissolved in 0.02% ascorbate and administered in a volume of 2 mL/kg. Test compounds are suspended in 8% Tween and injected in a volume of 2 mL/kg.

Surgery 15 minutes prior to surgery, animals are given an intraperitoneal injection of the noradrenergic uptake inhibitor desipramine (25 mg/kg) to prevent damage to non-dopamine neurones. Animals are then placed in an anaesthetic chamber and anaesthetised using a mixture of oxygen and isoflurane. Once unconscious, the animals are transferred to a stereotaxic frame, where anaesthesia is maintained through a mask. The top of the animal's head is shaved and sterilised using an iodine solution. Once dry, a 2 cm long incision is made along the midline of the scalp and the skin retracted and clipped back to expose the skull. A small hole is then drilled through the skill above the injection site. In order to lesion the nigrostriatal pathway, the injection cannula is slowly lowered to position above the right medial forebrain bundle at −3.2 mm anterior posterior, −1.5 mm medial lateral from bregma, and to a depth of 7.2 mm below the duramater. 2 minutes after lowing the cannula, 2 $\mu$L of 6-OHDA is infused at a rate of 0.5 $\mu$L/min over 4 minutes, yeilding a final dose of 8 $\mu$L. The cannula is then left in place for a further 5 minutes to facilitate diffusion before being slowly withdrawn. The skin is then sutured shut using Ethicon W501 Mersilk, and the animal removed from the strereotaxic frame and returned to its homecage. The rats are allowed 2 weeks to recover from surgery before behavioural testing.

Apparatus

Rotational behaviour is measured using an eight station rotameter system provided by Med Associates, San Diego, USA. Each station is comprised of a stainless steel bowl (45 cm diameter×15 cm high) enclosed in a transparent Plexiglas cover running around the edge of the bowl, and extending to a height of 29 cm. To assess rotation, rats are placed in cloth jacket attached to a spring tether connected to optical rotameter positioned above the bowl, which assesses movement to the left or right either as partial (45°) or full (360°) rotations. All eight stations are interfaced to a computer that tabulated data.

Procedure

To reduce stress during drug testing, rats are initially habituated to the apparatus for 15 minutes on four consecutive days. On the test day, rats are given an intraperitoneal injection of test compound 30 minutes prior to testing. Immediately prior to testing, animals are given a subcutaneous injection of a subthreshold dose of apomorphine, then placed in the harness and the number of rotations recorded for one hour. The total number of full contralatral rotations during the hour test period serves as an index of antiparkinsonian drug efficacy.

What is claimed is:

1. A compound of formula (I):

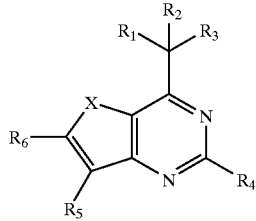

wherein:

X is S;

$R_1$ and $R_2$ are independently selected from hydrogen, alkyl, aryl, hydroxy, alkoxy, aryloxy, cyano, nitro, $CO_2R_7$, $COR_7$, $OCOR_7$, $CONR_7R_8$, $CONR_7NR_8R_9$, $OCONR_7R_8$, $NR_7R_8$, $NR_7COR_8$, $NR_7CONR_8R_9$, $NR_7CO_2R_8$, $NR_7SO_2R_8$, $NR_7CONR_8NR_9R_{10}$, $NR_7NR_8CO_2R_9$, $NR_7NR_8CONR_9R_{10}$, $NR_7SO_2NR_8R_9$, $SO_2R_7$, $SOR_7$, $SR_7$ and $SO_2NR_7R_8$, or $R_1$ and $R_2$ together form a carbonyl group (C=O), an oxime group (C=NOR$_{11}$), an imine group (C=NR$_{11}$) or a hydrazone group (C=NNR$_{11}R_{12}$), or $R_1$ and $R_2$ together form a 5, 6 or 7 membered carbocyclic ring;

$R_3$ is alkyl or aryl;

$R_4$, $R_5$ and $R_6$ are independently selected from hydrogen, alkyl, aryl, halogen, hydroxy, nitro, cyano, alkoxy, aryloxy, $COR_7$, $OCOR_7$, $CO_2R_7$, $SR_7$, $SOR_7$, $SO_2R_7$, $SO_2NR_7R_8$, $CONR_7R_8$, $CONR_7NR_8R_9$, $OCONR_7R_8$, $NR_7R_8$, $NR_7COR_8$, $NR_7CONR_8R_9$, $NR_7CO_2R_8$, $NR_7SO_2R_8$, $CR_7=NOR_8$, $NR_7CONR_8NR_9R_{10}$, $NR_7NR_8CO_2R_9$, $NR_7NR_8CONR_9R_{10}$, $SO_2NR_7NR_8R_9$, $NR_7SO_2NR_8R_9$, $NR_7NR_8SO_2R_9$, $NR_7NR_8COR_9$, $NR_7NR_8R_9$ and $NR_7CSNR_8R_9$; and $R_7$, $R_8$, $R_9$, $R_{10}$, $R_{11}$ and $R_{12}$ are independently selected from hydrogen, alkyl and aryl, or a pharmaceutically acceptable salt thereof.

2. A compound according to claim 1 wherein $R_1$ and $R_2$ are independently selected from hydrogen, hydroxy, cyano, alkyl and $CO_2R_7$.

3. A compound according to claim 2 wherein said alkyl group is a hydroxy-substituted alkyl.

4. A compound according to claim 2 wherein $R_7$ of said $CO_2R_7$ group is alkyl.

5. A compound according to claim 2 wherein one of $R_1$ and $R_2$ is hydrogen.

6. A compound according to claim 2 wherein $R_1$ is hydrogen and $R_2$ is cyano.

7. A compound according to claim 1 wherein $R_1$ or $R_2$ together form a carbonyl group.

8. A compound according to claim 1 wherein $R_1$ and $R_2$ together form an oxime group, an imine group or a hydrazone group.

9. A compound according to claim 1 wherein $R_3$ is aryl.

10. A compound according to claim 1 wherein $R_3$ is selected from thienyl, furyl, pyrrolyl, thiazolyl, phenyl and pyridyl.

11. A compound according to claim 10 wherein $R_3$ is selected from 2-thienyl and 2-pyridyl.

12. A compound according to claim 1 wherein $R_5$ is selected from hydrogen, alkyl and halogen.

13. A compound according to claim 1 wherein $R_6$ is selected from hydrogen, alkyl, aryl and halogen.

14. A compound according to claim 1 wherein both $R_5$ and $R_6$ are hydrogen.

15. A compound according to claim 1 wherein $R_4$ is selected from alkyl, halogen, alkoxy, alkylthio, monoalkylamino and dialkylamino.

16. A compound according to claim 1 wherein $R_4$ is selected from $NR_7R_8$.

17. A compound according to claim 16 wherein $R_4$ is $NR_7R_8$ and $R_7$ is hydrogen.

18. A compound according to claim 17 wherein $R_4$ is $NR_7R_8$ and $R_8$ is hydrogen.

19. A compound according to claim 16 wherein $R_4$ is $NR_7R_8$ and $R_8$ is substituted or unsubstituted alkyl.

20. A compound according to claim 1 wherein $R_4$ is selected from $NR_7R_8$, $NR_7NR_8COR_9$, $NR_7NR_8CO_2R_9$, $NR_7CO_2R_8$, $NR_7NR_8CONR_9R_{10}$, $NR_7NR_8SO_2R_9$, $NR_7NR_8CSNR_9R_{10}$, $NR_7NR_8R_9$ and $NR_7COR_8$.

21. A compound according to claim 20 wherein the $R_7$ substituent of the $R_4$ group is hydrogen.

22. A compound according to claim 1 wherein $R_4$ is an $NR_7R_8$ group and the $R_7$ and $R_8$ groups together form a ring to produce a saturated or partially unsaturated, substituted or unsubstituted 5-, 6- or 7-membered cyclic amino group optionally containing one or more additional heteroatoms.

23. A compound according to claim 22 wherein the heteroatoms of said cyclic amino group are selected from N and O.

24. A compound according to claim 22 wherein the cyclic amino group is selected from pyrrolidinyl, pyrrolidinonyl, piperidinyl, piperazinyl and morpholinyl groups.

25. A compound according to claim 1 which is selected from (2R)-2-(1-Hydroxy-2-propylamino)thieno[3,2-d]pyrimidin-4-yl 2-thienylmethanone, 2-(3-(1H-Imidazol-1-yl)propylamino)thieno[3,2-d]pyrimidin-4-yl 2-thienylmethanone, (2RS)-2-(1-Hydroxy-2-propylamino)thieno[3,2-d]pyrimidin-4-yl 2-thienylmethanone, 2-(3-Hydroxypropylamino)thieno[3,2-d]pyrimidin-4-yl 2-thienylmethanone, 3-Methyl-N-(2-(4-(2-thienylcarbonyl)thieno[3,2-d]pyrimidin-2-yl)aminoethyl)butanamide, Methyl (2-(4-(2-thienylcarbonyl)thieno[3,2-d]pyrimidin-2-yl)aminoethyl)carbamate, 2-(2-(1H-Imidazol-4-yl)ethylamino)thieno[3,2-d]pyrimidin-4-yl 2-thienylmethanone,(2RS)-2-(2,3-Dihydroxypropylamino)thieno[3,2-d]pyrimidin-4-yl 2-thienylmethanone, (2R)-2-(2-Hydroxypropylamino)thieno[3,2-d]pyrimidin-4-yl 2-thienylmethanone, 2-(2-Hydroxyethylamino)thieno[3,2-d]pyrimidin-4-yl 3-methyl-2-thienylmethanone, 2-Chloroethyl (2-(4-(2-thienylcarbonyl)thieno[3,2-d]pyrimidin-2-yl)aminoethyl)carbamate, 20 (2S)-2-(1-Hydroxy-2-propylamino)thieno[3,2-d]pyrimidin-4-yl 2-thienylmethanone, 2-(3-(1H-Imidazol-1-yl)propylamino)thieno[3,2-d]pyrimidin-4-yl 3-methyl-2-thienylmethanone, N-(2-(4-(2-Thienylcarbonyl)thieno[3,2-d]pyrimidin-2-yl)aminoethyl)cyclohexylcarboxamide, Ethyl 4-(4-(2-thienylcarbonyl)thieno[3,2-d]pyrimidin-2-ylamino)butanoate, 2-(2-Pyridylmethylamino)thieno[3,2-d]pyrimidin-4-yl 2-thienylmethanone,(2S)-2-(2-Hydroxypropylamino)thieno[3,2-d]pyrimidin-4-yl 2-thienylethanone,N-Allyl-N'-(2-(4-(2-thienylcarbonyl)thieno[3,2-d]pyrimidin-2-yl)aminoethyl)urea, N-(2-(4-(2-Thienylcarbonyl)thieno[3,2-d]pyrimidin-2-yl)aminoethyl)acetamide, 2-(Tetrahydrofuran-2-ylmethylamino)thieno[3,2-d]pyrimidin-4-yl 2-thienylmethanone, N-Benzyl-N'-(2-(4-(2-thienylcarbonyl)thieno[3,2-d]pyrimidin-2-yl)

aminoethyl)urea, 2-(2-Hydroxyethylamino)thieno[3,2-d]pyrimidin-4-yl 2-thienylmethanone,Benzyl (2-(4-(2-thienylcarbonyl)thieno[3,2-d]pyrimidin-2-yl)aminoethyl)carbamate and 2-Aminothieno[3,2-d]pyrimidin-4-yl 2-thienylmethanone.

26. A pharmaceutical composition comprising a compound according to claim 1 and a pharmaceutically acceptable carrier or excipient.

27. A method of treating a disorder in which the blocking of $A_{2A}$ receptors is beneficial comprising administering to a subject in need of such treatment an effective dose of a compound as set out in claim 1 or a pharmaceutically acceptable salt thereof wherein said disorder is selected from movement disorders; acute and chronic pain; affective disorders; central and peripheral nervous system degenerative disorders; cognitive disorders; central nervous system injury; cerebral ischaemia; myocardial ischaemia; muscle ischaemia; sleep disorders selected from hypersomnia; eye disorders selected from retinal ischaemia-reperfusion injury and diabetic neuropathy; cardiovascular disorders; and diabetes.

28. A method of treating movement disorders comprising administration to a subject in need of such treatment an effective dose of a compound as set out in any one of claim 1, or a pharmaceutically acceptable salt thereof.

29. A method according to claim 28 wherein the movement disorder is Parkinson's disease.

30. A method according to claim 29 for treatment of drug-induced Parkinsonism, post-encephalitic Parkinsonism, Parkinsonism induced by poisoning or post-traumatic Parkinson's disease.

31. A method according to claim 28 wherein the movement disorder is progressive supernuclear palsy, Huntingtons disease, multiple system atrophy, corticobasal degeneration, Wilsons disease, Hallerrorden-Spatz disease, progressive pallidal atrophy, Dopa-responsive dystoma-Parkinsonism, spasticity, Alzheimer's disease or other disorders of the basal ganglia which result is dyskinesias.

32. A method according to claim 28 wherein the compound of formula (I) is in combination with one or more additional drugs useful in the treatment of movement disorders, the components being in the same formulation or in separate formulations for administration simultaneously or sequentially.

33. A method according to claim 32 wherein said additional drug(s) useful in the treatment of movement disorders is/are a drug useful in the treatment of Parkinson's disease.

34. A method according to claim 32 wherein one of the additional drugs is L-DOPA.

35. A method according to claim 27 wherein said disorder is depression, acute or chronic pain or a cognitive disorder.

36. A method of neuroprotection comprising administration to a subject in need of such treatment an effective dose of a compound as set out in claim 1, or a pharmaceutically acceptable salt thereof.

37. A method according to claim 27 wherein said method is for neuroprotection in a subject suffering from or at risk from a neurodegenerative disorder.

38. A method according to claim 37 wherein said neurodegenerative disorder is a movement disorder.

39. A method according to claim 38 wherein said movement disorder is drug-induced Parkinsonism, post-encephalitic Parkinsonism, Parkinsonism induced by poisoning, post-traumatic Parkinson's disease, progressive supernuclear palsy, Huntingtons disease, multiple system atrophy, corticobasal degeneration, Wilsons disease, Hallerrorden-Spatz disease, progressive pallidal atrophy, Dopa-responsive dystoma-Parkinsonism, spasticity, Alzheimer's disease or other disorders of the basal ganglia which result is dyskinesias.

40. A method according to claim 27 wherein the subject is human.

* * * * *